US008133451B2

(12) United States Patent
Yuan

(10) Patent No.: US 8,133,451 B2
(45) Date of Patent: Mar. 13, 2012

(54) SAMPLE PREPARATION APPARATUS

(75) Inventor: Bob Yuan, Belmont, CA (US)

(73) Assignee: MicroFluidic Systems, Inc., Fremont, CA (US)

( * ) Notice: Subject to any disclaimer, the term of this patent is extended or adjusted under 35 U.S.C. 154(b) by 443 days.

(21) Appl. No.: 12/290,283

(22) Filed: Oct. 28, 2008

(65) Prior Publication Data

US 2010/0050749 A1 Mar. 4, 2010

Related U.S. Application Data

(63) Continuation-in-part of application No. 12/231,171, filed on Aug. 28, 2008.

(51) Int. Cl.
*G01N 31/22* (2006.01)
*C12Q 1/68* (2006.01)
*G05D 9/00* (2006.01)
*B01L 3/00* (2006.01)

(52) U.S. Cl. ............ 422/404; 422/50; 422/430; 422/62; 422/500; 422/501; 422/502; 422/509; 422/521; 422/546; 422/547; 422/554; 422/106; 436/180

(58) Field of Classification Search .................... 422/67, 422/500–505, 509, 547, 554; 436/180
See application file for complete search history.

(56) References Cited

U.S. PATENT DOCUMENTS

| | | | |
|---|---|---|---|
| 4,275,166 A | 6/1981 | McCollough et al. | 435/227 |
| 4,610,961 A | 9/1986 | Guardino et al. | 435/34 |
| 4,666,595 A | 5/1987 | Graham | 210/222 |
| 4,806,313 A | 2/1989 | Ebersole et al. | |
| 5,048,520 A | 9/1991 | Vago | 128/24 A |
| 5,234,809 A | 8/1993 | Boom et al. | 435/91 |
| 5,475,203 A | 12/1995 | McGaffigan | 219/548 |
| 5,681,752 A | 10/1997 | Prather | 436/173 |
| 5,707,799 A | 1/1998 | Hansmann et al. | 435/6 |

(Continued)

FOREIGN PATENT DOCUMENTS

WO   WO 99/33559   7/1999

(Continued)

OTHER PUBLICATIONS

International Search Report for PCT Application No: PCT/US2009/62067, date of mailing Dec. 18, 2009, filed Oct. 26, 2009, authorized officer Lee W. Young, 9 pages.

(Continued)

*Primary Examiner* — Jill Warden
*Assistant Examiner* — Dean Kwak
(74) *Attorney, Agent, or Firm* — Haverstock & Owens LLP

(57) ABSTRACT

A capture and purification apparatus is configured as a stand-alone apparatus or as part of a larger system. The capture and purification apparatus can be configured as a microfluidic cartridge that includes microfluidic circuitry and individually controlled valves. The microfluidic cartridge can be configured to function independently, or can be configured to be coupled to a separate instrument that provides the actuation to perform the capture and purification process. The capture and purification apparatus is configured as a volume-driven system that applies single-direction valves, a single fluid driving device, and fluid lines to control and discretely direct fluid flow within a full-loaded fluidic system. Such control enables various fluid sample processing techniques to be performed including, but not limited to, lysis, thermal cycling, and/or target analyte capture and purification, for example using a combination of ion-exchange chromatography and size-exclusion chromatography (SEC).

19 Claims, 29 Drawing Sheets

U.S. PATENT DOCUMENTS

| | | | |
|---|---|---|---|
| 5,952,173 A | 9/1999 | Hansmann et al. | 435/6 |
| 5,968,731 A | 10/1999 | Layne et al. | 435/5 |
| 6,033,880 A | 3/2000 | Haff et al. | 435/91.1 |
| 6,100,084 A | 8/2000 | Miles et al. | 435/306.1 |
| 6,134,944 A | 10/2000 | Yu et al. | 73/23.35 |
| 6,146,591 A | 11/2000 | Miller | 422/65 |
| 6,228,634 B1 | 5/2001 | Blumenfeld et al. | 435/286.1 |
| 6,318,158 B1 | 11/2001 | Breen et al. | 73/64.56 |
| 6,374,684 B1 | 4/2002 | Dority | 73/864.81 |
| 6,391,541 B1 | 5/2002 | Peterson et al. | 435/5 |
| 6,440,725 B1 | 8/2002 | Pourahmadi et al. | 435/288.5 |
| 6,481,290 B1 | 11/2002 | MacInnis et al. | 73/644 |
| 6,540,895 B1 | 4/2003 | Spence et al. | 204/450 |
| 6,562,209 B1 | 5/2003 | Sullivan et al. | 204/403.01 |
| 6,565,815 B1 | 5/2003 | Chang et al. | 422/198 |
| 6,741,174 B2 | 5/2004 | Rhoades et al. | 340/540 |
| 6,746,864 B1 | 6/2004 | McNeil et al. | 435/288.7 |
| 6,766,277 B2 | 7/2004 | Siegel | 702/187 |
| 6,787,104 B1 | 9/2004 | Mariella, Jr. | 422/4 |
| 6,800,452 B1 | 10/2004 | McNeil et al. | 435/29 |
| 6,878,540 B2 | 4/2005 | Pourahmadi et al. | 435/287.2 |
| 6,887,693 B2 | 5/2005 | McMillan et al. | 435/173.7 |
| 6,905,885 B2 | 6/2005 | Colston et al. | 436/518 |
| 6,951,147 B2 | 10/2005 | Call et al. | 73/836.22 |
| 6,979,543 B2 | 12/2005 | Chen et al. | 435/6 |
| 7,005,982 B1 | 2/2006 | Frank | 340/539.26 |
| 7,006,923 B1 | 2/2006 | Rubin | 702/19 |
| 7,070,935 B2 | 7/2006 | Schaudies et al. | 435/6 |
| 7,082,369 B1 | 7/2006 | Rubin | 702/19 |
| 7,106,442 B2 | 9/2006 | Silcott et al. | 356/338 |
| 2001/0032666 A1 | 10/2001 | Jensen et al. | 136/256 |
| 2001/0036630 A1 | 11/2001 | Ibrahim | 435/6 |
| 2002/0022261 A1 | 2/2002 | Anderson et al. | 435/287.2 |
| 2002/0039783 A1 | 4/2002 | McMillan et al. | 435/287.2 |
| 2003/0003441 A1 | 1/2003 | Colston et al. | 435/5 |
| 2003/0038087 A1 | 2/2003 | Garvin | 210/767 |
| 2003/0153021 A1 | 8/2003 | Lu et al. | 435/7.32 |
| 2003/0215845 A1 | 11/2003 | Bille | 435/6 |
| 2004/0038385 A1 | 2/2004 | Langlois et al. | 435/287.1 |
| 2004/0197793 A1 | 10/2004 | Hassibi et al. | 435/6 |
| 2004/0259234 A1 | 12/2004 | Chou et al. | 435/287.1 |
| 2005/0019902 A1 | 1/2005 | Mathies et al. | |
| 2005/0026276 A1 | 2/2005 | Chou | 435/287.2 |
| 2005/0056785 A1 | 3/2005 | Chou et al. | 250/338.1 |
| 2005/0064598 A1 | 3/2005 | Yuan et al. | 436/63 |
| 2005/0142565 A1 | 6/2005 | Samper et al. | 435/6 |
| 2005/0157301 A1 | 7/2005 | Chediak et al. | 356/417 |
| 2005/0190058 A1 | 9/2005 | Call | 340/539.26 |
| 2005/0227275 A1 | 10/2005 | Jung et al. | 435/6 |
| 2005/0239192 A1 | 10/2005 | Nasarabadi et al. | 435/287.1 |
| 2006/0006327 A1 | 1/2006 | Donaldson et al. | 250/288 |
| 2006/0057599 A1 | 3/2006 | Dzenitis et al. | 435/6 |
| 2006/0063160 A1 | 3/2006 | West et al. | 435/6 |
| 2006/0073484 A1 | 4/2006 | Mathies et al. | 435/6 |
| 2006/0073585 A1 | 4/2006 | McDevitt et al. | 435/288.7 |
| 2006/0197033 A1 | 9/2006 | Hairston et al. | 250/458.1 |
| 2006/0219939 A1 | 10/2006 | Satyanarayana et al. | 250/458.1 |
| 2006/0257853 A1 | 11/2006 | Herman | 435/288.7 |
| 2007/0026439 A1 | 2/2007 | Faulstich et al. | |
| 2007/0116607 A1 | 5/2007 | Wang et al. | 422/83 |
| 2007/0248958 A1* | 10/2007 | Jovanovich et al. | 435/6 |
| 2008/0050803 A1 | 2/2008 | Northrup et al. | 435/287.2 |
| 2008/0069733 A1* | 3/2008 | Maltezos et al. | 422/82.05 |
| 2008/0110458 A1* | 5/2008 | Srinivasan et al. | 128/203.26 |
| 2008/0125330 A1 | 5/2008 | Cady et al. | 506/17 |
| 2009/0036668 A1* | 2/2009 | Elizarov et al. | 536/122 |
| 2009/0142198 A1* | 6/2009 | Votaw et al. | 417/53 |

FOREIGN PATENT DOCUMENTS

| | | |
|---|---|---|
| WO | WO 03/070898 A2 | 8/2003 |
| WO | WO 2005/078674 A2 | 8/2005 |

OTHER PUBLICATIONS

Office Action, mail date May 10, 2010, U.S. Appl. No. 11/509,868, filed Aug. 24, 2006, first named inventor: Amy J. Devitt, 21 pages.

* cited by examiner

```
540 → Intake Ambient Air
         ↓
545 → Measure Optical Characteristics
         ↓
550   Compare to Known Optical Characteristics  — No →  (loop back to 540)
         ↓ Yes
555 → Generate Trigger Signal
         ↓
560 → Output Fluid Sample
         ↓
565 → Confirm Presence of Biological Particles
```

Fig. 11

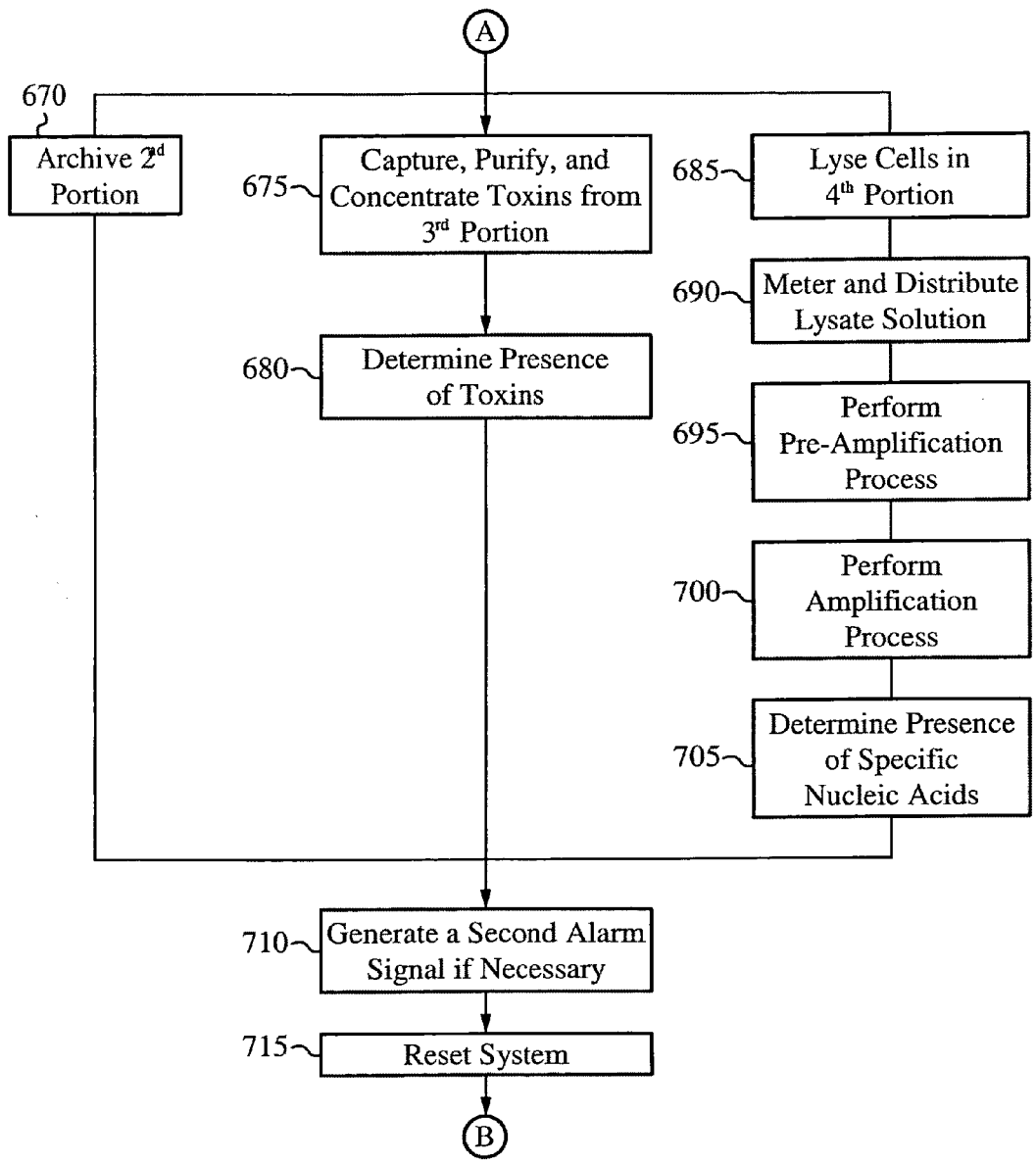
Fig. 13 (con't)

SAMPLE PREPARATION APPARATUS

RELATED APPLICATIONS

This patent application is a continuation-in-part of U.S. patent application Ser. No. 12/231,171, filed on Aug. 28, 2008, and entitled "Method and Apparatus for Purifying and Collecting Analytes." This application incorporates U.S. patent application Ser. No. 12/231,171, filed on Aug. 28, 2008, entitled "Method and Apparatus for Purifying and Collecting Analytes", in its entirety by reference.

GOVERNMENT LICENSE RIGHTS

This invention was made with Government support under Agreement No. W81XWH-04-9-0010 awarded by the Government. The Government has certain rights in this invention.

FIELD OF THE INVENTION

The invention relates to a method of and apparatus for preparing one or more target analytes for analysis. More particularly, the invention relates to preparing one or more target analytes including capturing and purifying one or more target analytes from a sample.

BACKGROUND OF THE INVENTION

Bio-threat detectors are used to monitor the ambient air to detect the presence of potentially harmful pathogens. In general, air is drawn into a collection and detection apparatus where the particulates in the air are evaluated. Airflow into the collection and detection apparatus is typically generated by a fan within the apparatus. The apparatus continuously monitors the air and the individual molecules within a given airflow. Some detectors use lasers or LEDs to scan the air path to interrogate the particles passing through. A harmless particle, such as a dust particle, can be discriminated from a harmful particle, for example an anthrax spore, because each different type of particle reflects a different wavelength of light. Light reflected off the passing particles is matched to a database of known wavelengths, a match indicating a biological entity is present. When a matching wavelength is detected, a triggering mechanism within the detection apparatus is activated. When the triggering mechanism is activated, a trigger signal is generated which indicates that a potential pathogen is present. However, the specific type of particle is not identified by such a collection and detection apparatus.

A confirmation process is initiated once the triggering mechanism signals the presence of a possible pathogen. During the confirmation process, the particles that triggered the detection apparatus are identified. Conventionally, when the trigger signal is generated, the potential pathogen is collected and taken to a lab where an analysis is performed. Multiple techniques are performed to identify the potential pathogen, each technique is designed to identify a different type of pathogen, typically performed under the supervision of a lab operator. This is a time-consuming process requiring various pieces of test equipment, which is impractical for real-time threat assessment. Such processes also require the interaction of a human operator, which is costly and often inefficient. Continuous monitoring and processing of potential pathogens, over a 24 hour a day period, requires multiple such human operators to cover the desired time frame.

A step in the identification process includes capturing and purifying potential pathogens from within a fluid sample. For large volume fluid samples, such as 1 ml or greater, extraction of the potential pathogens is problematic due to the relatively lengthy time frame required. In one method, the fluid sample is exposed to a binding surface area, yet for a large volume, the amount of time for the pathogens within the fluid sample to diffuse to the binding surface is unacceptably long, or the flow rate past the binding surfaces is too slow in some applications. In another method, the fluid sample is cultured to enable the pathogen to grow, if present. However, the time period for culturing is also unacceptably long in some applications.

SUMMARY OF THE INVENTION

A capture and purification apparatus utilizes a combination of ion-exchange chromatography and size-exclusion chromatography (SEC). A fluid sample including one or more targeted analytes is processed through a first column configured for ion-exchange chromatography. Targeted analytes collected within the first column are eluted using a high concentration buffer solution. The targeted analytes are subsequently separated from the eluted solution using a second column configured for SEC. An output fraction including the targeted analytes is collected as output from the second column.

The capture and purification apparatus is configured as a stand-alone apparatus or as part of a larger system. In some embodiments, the capture and purification apparatus is configured as a microfluidic cartridge that includes microfluidic circuitry and individually controlled valves. The microfluidic cartridge can be configured to function independently, or can be configured to be coupled to a separate instrument that provides the actuation to perform the capture and purification process.

In one aspect, an apparatus to process an input fluid sample including one or more targeted analytes is disclosed. The apparatus includes a master fluid driver, a plurality of individually actuated fluid valves, a plurality of slave fluid drivers, and fluid lines coupled to the master fluid driver, the plurality of fluid valves, and the plurality of slave fluid drivers. The master fluid driver is configured to be actuated in discrete increments. The plurality of individually actuated fluid valves are configured to regulate fluid flow, wherein each fluid valve is configured to be actuated no more than once. The plurality of slave fluid drivers are coupled to the master fluid driver, wherein actuation of the master fluid driver selectively actuates the plurality of slave fluid drivers according to a number of increments the master slave fluid driver is incremented and according to a number of fluid valves that are actuated. The apparatus is fully loaded with a plurality of processing fluids and the fluid sample, further wherein the selective actuation of the plurality of slave fluid drivers functions to selectively displace the one or more targeted analytes between a plurality of processing areas and to selectively provide one or more of the plurality of processing fluids to the processing areas.

In another aspect, another apparatus to process an input fluid sample including one or more targeted analytes is disclosed. The apparatus includes an actuation mechanism, a cartridge, and a control module. The actuation instrument includes a drive motor configured to provide discrete increments of actuation, and a plurality of valve actuation mechanisms. The cartridge includes a driving syringe coupled to the drive motor, a plurality of reagent syringes, wherein a fluid input port of each reagent syringe is commonly coupled to the driving syringe, further wherein each reagent syringe is configured to displace a reagent fluid in response to an actuation of the driving syringe, each reagent fluid is used to process the one of more target analytes, a plurality of processing vessels, each processing vessel configured to process the one or more target analytes, and microfluidic circuitry including a plurality of valves and fluid lines configured to couple the driving syringe, the plurality of reagent syringes, and the plurality of processing vessels, wherein each valve is coupled to one valve actuation mechanism and each valve is configured to actuate no more than once, further wherein a position of the one or more target analytes within the cartridge is determined according to a cumulative amount of actuation increments of the drive motor. The control module is configured to provide control signals to independently actuate the drive motor and each of the plurality of valve actuation mechanisms.

BRIEF DESCRIPTION OF THE DRAWINGS

The accompanying drawings, which are incorporated in and form a part of this specification, illustrate embodiments of the invention and, together with the description, serve to explain the principles of the invention but not limit the invention to the disclosed examples.

FIG. 11 illustrates an exemplary automated process performed by the second embodiment of the particle collection and detection system.

Embodiments of the capture and purification apparatus are described relative to the several views of the drawings. Where appropriate and only where identical elements are disclosed and shown in more than one drawing, the same reference numeral will be used to represent such identical elements.

DETAILED DESCRIPTION OF THE PRESENT INVENTION

Reference will now be made in detail to the embodiments of the capture and purification apparatus and process of the invention, examples of which are illustrated in the accompanying drawings. While the invention will be described in conjunction with the embodiments below, it will be understood that they are not intended to limit the invention to these embodiments and examples. On the contrary, the invention is intended to cover alternatives, modifications and equivalents, which may be included within the spirit and scope of the invention as defined by the appended claims. Furthermore, in the following detailed description of the present invention, numerous specific details are set forth in order to more fully illustrate the present invention. However, it will be apparent to one of ordinary skill in the prior art that the present invention may be practiced without these specific details. In other instances, well-known methods and procedures, components and processes haven not been described in detail so as not to unnecessarily obscure aspects of the present invention.

Embodiments of the present invention are directed to a capture and purification apparatus configured to process an input fluid solution including one or more targeted analytes, such as pathogens, and to output a concentrated fluid sample including the targeted analytes. In some embodiments, the capture and purification apparatus is configured within a fully integrated and autonomous, collection and detection system configured to monitor the ambient air for specific particles, such as the pathogens. In some embodiments, the collection and detection system is configured as an integrated cartridge. In some embodiments, the collection and detection system is configured as a fully autonomous system. An air collector captures airborne particles and outputs a fluid sample including the captured particles in a fluid solution. The collection and detection system includes a control module configured to control the processing of the fluid sample such that detection of one or more types of particles is fully automated within the integrated cartridge. The types of particles to be processed and detected include, but are not limited to, cells, bacteria, viruses, nucleic acids, toxins, and other pathogens. If one or more specific types of particles are detected, a system alarm is triggered. In some embodiments, the system alarm is an alarm signal which is transmitted over a communications network to either a local or central monitoring location. More than one collection and detection system can be coupled to the network and monitored by the central monitoring location. In other embodiments, the system alarm is an audio and/or visual signal generated by the collection and detection system itself.

Figure 1:
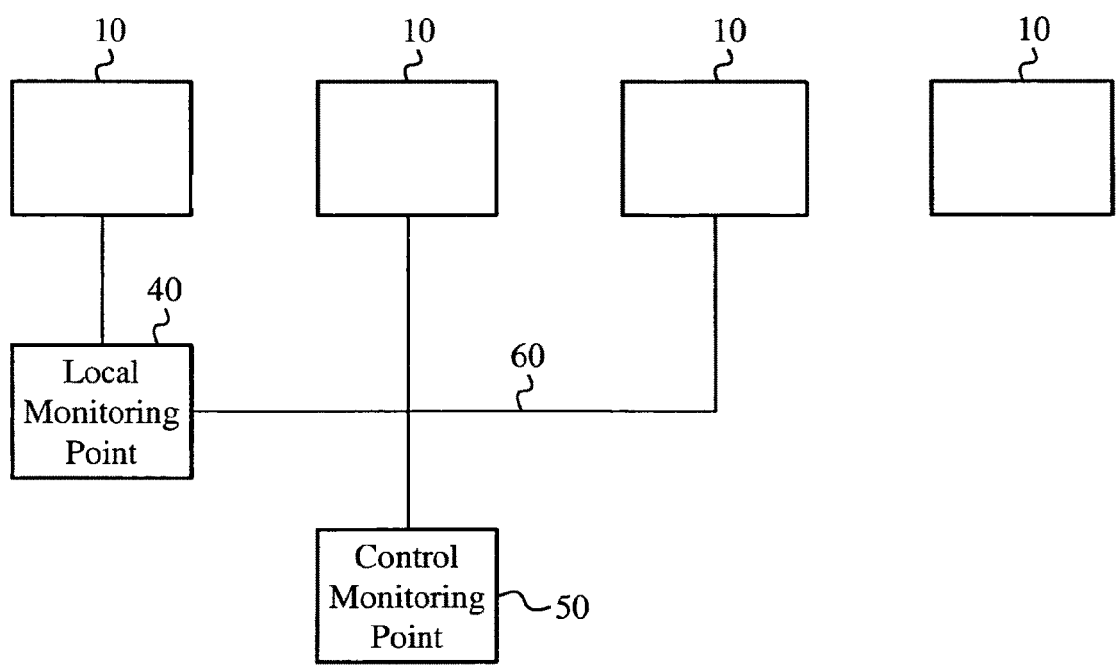
FIG. 1 illustrates an exemplary network configuration including multiple collection and detection systems.

FIG. 1 illustrates an exemplary network configuration including multiple collection and detection systems 10. Each collection and detection system 10 can be operated independently, or networked to a remote monitoring location, as is illustrated in FIG. 1. The monitoring location can be local, as in the local monitoring point 40, or centralized, such as the central monitoring point 50. As shown in FIG. 1, each collection and detection system can operate independently, can be coupled to a local monitoring point, which in turn can be coupled to a central monitoring point, or can be coupled to the central monitoring point. The collection and detection system 10 is coupled to the local monitoring point 40 or the central monitoring point 50 via any conventional network 60. Network connectivity also enables remote control signal to be provided to the collection and detection system 10.

Figure 2:
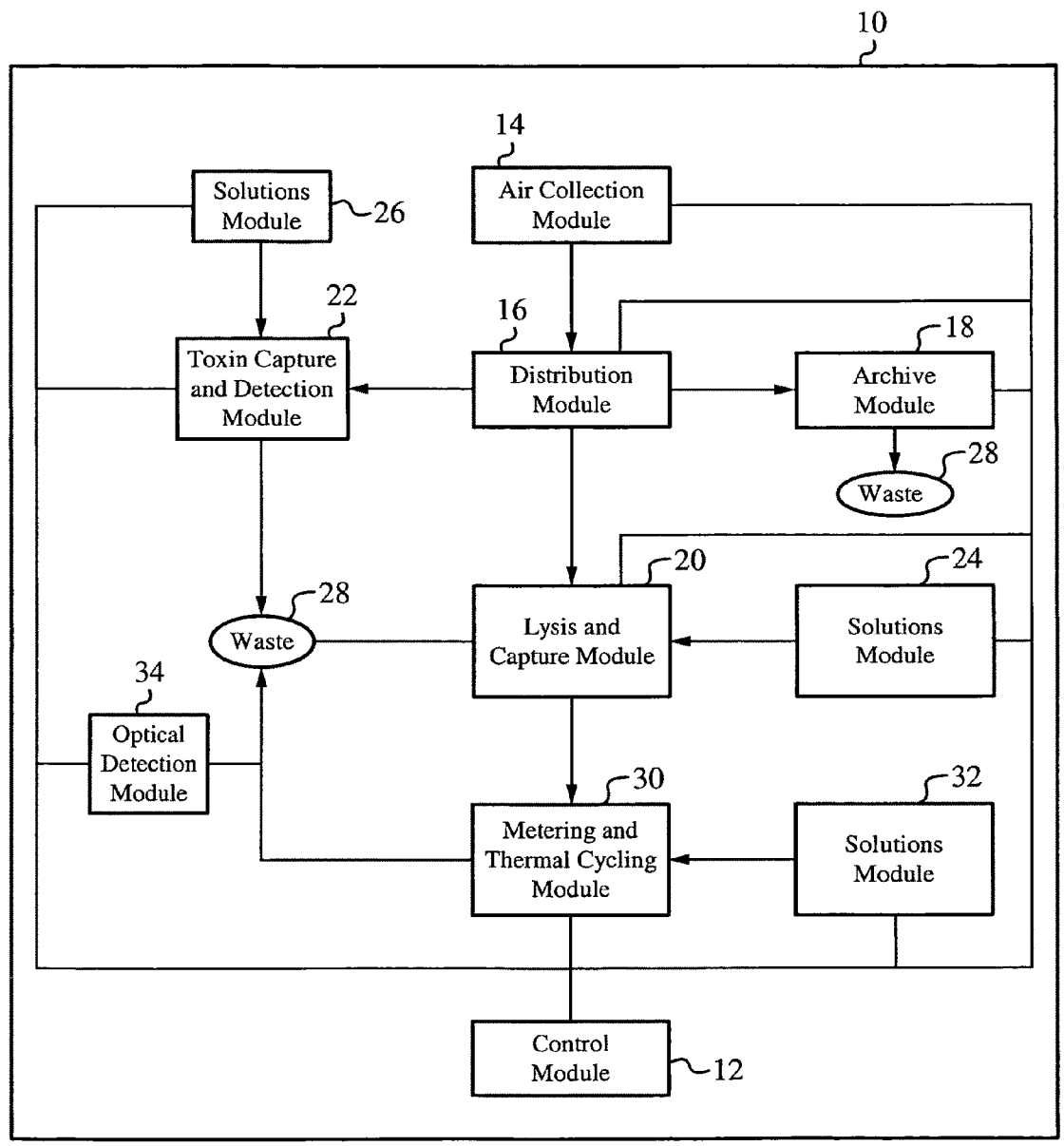
FIG. 2 illustrates an exemplary functional block diagram of a first embodiment of the integrated collection and detection system.

A first embodiment of the integrated collection and detection system is directed to a detect to treat system in which specific particles are identified. FIG. 2 illustrates an exemplary functional block diagram of the first embodiment of the integrated collection and detection system. The integrated collection and detection system 10 includes a control module 12, an air collection module 14, a distribution module 16, an archive module 18, a lysis and capture module 20, a toxin capture and detection module 22, a solutions module 24, a solutions module 26, a waste module 28, a metering and thermal cycling module 30, a solutions module 32, and an optical detection module 34. Fluid is directed between modules and within each module using microfluidic pathways and valves, also referred to as microfluidic circuitry.

The air collection module 14 is configured to intake ambient air and collect airborne particles within the air. Air is collected for a predetermined time frame, after which the collected particles are eluted into a liquid sample which is output from the air collection module 14. The fluid sample output from the air collection module 14 includes a fluid and particle solution.

The distribution module 16 meters and distributes the fluid sample output from the air collection module 14. The fluid sample is metered and distributed according to predetermined ratios. A first portion of the fluid sample is directed to the archive module 18, a second portion to the lysis and capture module 20, and a third portion to the toxin capture and detection module 22. In one embodiment, a syringe pump is used as part of the microfluidic circuitry to meter the fluid sample. A syringe pump is adaptable for changing applications, such as changing the distribution ratio from one application to the next. In another embodiment, a reservoir with drain holes is included as part of the microfluidic circuitry. The location of each drain hole corresponds to a desired distribution ratio. A valve is coupled to the drain line of each drain hole to control the collection and distribution of the fluid sample between runs. Such a configuration is appropriate where the distribution ratio is fixed, as the location of the drain holes is a fixed specification. In yet another embodiment, aspects of a fixed ratio configuration, such as the reservoir with drain holes, is combined with aspects of the adjustable ratio configuration, such as the syringe pump. It is understood that other microfluidic circuit configurations can be used to meter and distribute the fluid samples for both fixed and variable distribution ratios.

The archive module 18 is configured to store one or more fluid samples. The fluid samples are stored for later analysis and/or confirmation, if necessary. The lysis and capture module 20 is configured to perform a lysis, purification, and concentration process on the fluid sample received from the distribution module 16. Lysis is performed on cells within the received fluid sample that are capable of being lysed. Lysis is performed using sonication. Alternatively, any conventional lysis method can be used. Once the cells are lysed, the resulting nucleic acids are purified and concentrated to be sent to the metering and thermal cycling module 30. The solutions module 24 provides solutions used during the lysis, purification, and concentration steps performed in the lysis and capture module 20. For example, the solutions module 24 includes wash solutions and elution buffers.

The metering and thermal cycling module 30 receives the concentrated fluid sample from the lysis and capture module 20. The received fluid sample is metered and distributed into a predetermined number of collection vessels. The metering and thermal cycling module 30 is coupled to the solutions module 32 to receive mixing solution that is metered and distributed to each collection vessel such that a combination of concentrated fluid sample and mixing solution are temporarily stored in each collection vessel. Each collection vessel is coupled to a corresponding thermal cycling chamber to successively heat and cool the combined solution. In this manner, the fluid sample and mixing solution combination within each collection vessel undergoes a thermal cycling process within the thermal cycling chambers to amplify any nucleic acids present in the fluid sample. Any number of thermal cycles can be performed. This amplification process can be repeated, for example a pre-amplification step and an amplification step can be performed.

The amplified fluid sample from each thermal cycling chamber is successively output from the metering and thermal cycling module 30. Each amplified fluid sample output from the metering and thermal cycling module 30 is interrogated by the optical detection module 34. In general, any conventional luminescence detection technology can be applied to perform biological detection. The raw data obtained by the optical detection module 34 is provided to the control module 12, where it is used to determine the presence of one or more types of nucleic acids. If a nucleic acid is detected, the control module 12 generates an alarm signal. Alternatively, the raw data collected by the optical detection module 34 is sent to a remote location, such as the central monitoring point 50 (FIG. 1) for analysis.

The toxin capture and detection module 22 is configured to capture toxins present in the fluid sample received from the distribution module 16. The toxin capture and detection module 22 is also configured to detect the presence of any captured toxins using any conventional luminescence detection technology. The raw data obtained by the toxin capture and detection module 22 is provided to the control module 12, where it is used to determine the presence and identity of one or more specific types of toxins. If a specific toxin is detected, the control module 12 generates an alarm signal. Alternatively, the raw data collected by the toxin capture and detection module 22 is sent to a remote location, such as the central monitoring point 50 (FIG. 1) for analysis. In one embodiment, the toxin capture and detection module 22 includes an optical detection device configured to measure one or more characteristics of any captured toxin. The solutions module 26 provides solutions used during the toxin capture steps performed in the toxin capture and detection module 22. For example, the solutions module 26 includes wash solutions and antibody solutions.

The collection and detection system 10 is configured to be re-used such that successive fluid samples output by the air collection module 14 are processed. As such, the distribution module 16, the lysis and capture module 20, the toxin capture and detection module 22, the metering and thermal cycling module 30, and all interconnecting microfluidic circuitry including the microfluidic circuitry coupling the metering and thermal cycling module 30 and the optical detection module 34 are decontaminated between cycles. Various solutions are used to perform the rinse and wash steps during decontamination, these solutions are included in the solutions module 24 and the solutions module 26.

The control module 12 is coupled to each module to control operation of the collection and detection system 10. Such control enables complete automation of the collection and detection process, without need of human intervention. The control module 12 is also configured to analyze the raw data provided by the toxin capture and detection module 22 and the optical detection module 24, and to generate any appropriate alarm signals. In response to an alarm signal, the control module 12 initiates a localized audio and/or visual alarm and/or transmits a notification signal to a networked local monitoring location or a centralized monitoring location.

The analyzed fluid samples, elution buffers, mixing solutions, rinses, washes, purged archive samples, and other solutions related to the processing of fluid samples and subsequent decontamination of the collection and detection system 10 are directed to the waste module 28. Alternatively, fluid samples analyzed and subsequently output by the toxin capture and detection module 22 and the optical detection module 34 can be archived, either in the archive module 18, or a supplemental archive module (not shown). The embodiments of the particle collection and detection module 10 described above include three solutions modules. Alternatively, one or more of the solutions modules 24, 26, and 32 can be combined, or more than three solutions modules can be used.

The system implementation illustrated in FIG. 2 is for illustrative purposes. The microfluidic circuitry and module nature of the integrated collection and detection system provides flexibility and extensibility to interconnect and configure the modules, and associated sub-modular components, into any desired combination. For example, the fluid sample can be metered into additional portions, and each portion can be further sub-divided into smaller portions. These portions can be distributed to any one of a multitude of fluid processing pathways, including the fluid pathway through the lysis and capture module 20 and the metering and thermal cycling module 30, the fluid pathway through the toxin capture and detection module 22, and any other fluidic pathway configured according to one or more of the modules and/or sub-modules described above. As an additional example, a lysis module similar to the lysis component in the lysis and capture module 20 can be added prior to the toxin capture and detect module 22 to lyse cells prior to delivering the fluid sample to the toxin capture and detect module 22. Similar parallel pathways can also be configured such that a portion of the fluid sample is received un-lysed by the toxin capture and detect module 22, and another portion of the fluid sample is first lysed by a lysis component and then the lysed sample is delivered to another toxin capture and detect module. Additionally, the specific configurations described for each of the modules is for exemplary purposes. The microfluidic circuitry and constituent components of each module can be adapted into any number of configurations to perform the described functionality.

Figure 3:
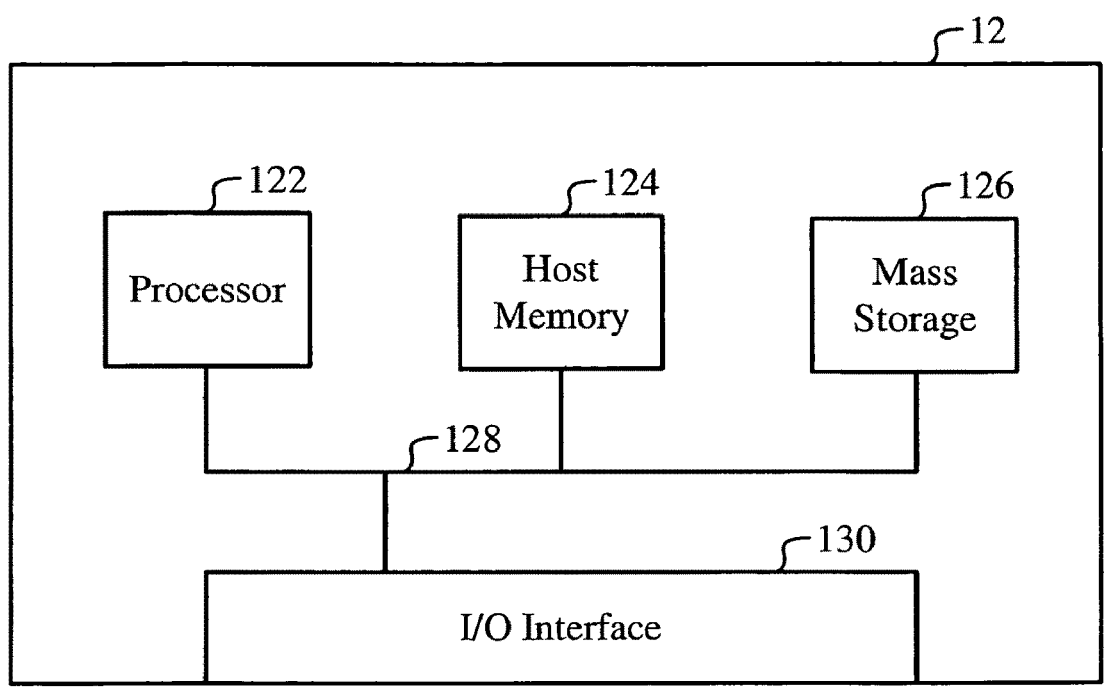
FIG. 3 illustrates an exemplary block diagram of the control module.

FIG. 3 illustrates an exemplary block diagram of the control module 12. The control module 12 includes a processor 122, a host memory 124, a mass storage 126, and an I/O interface 130, all coupled via a system bus 128. The mass storage 126 can include both fixed and removable media using any one or more of magnetic, optical or magneto-optical storage technology or any other available mass storage technology. The host memory 124 is a random access memory (RAM). The processing module 122 is configured to control the operation of the collection and detection system 10. The I/O interface 130 includes a user interface and a network interface. In some embodiments, the user interface includes a display to show user instructions and feedback related to input user commands. The network interface includes a physical interface circuit for sending and receiving data and control communications over a conventional network, such as to a local or centralized monitoring location.

Figure 4:
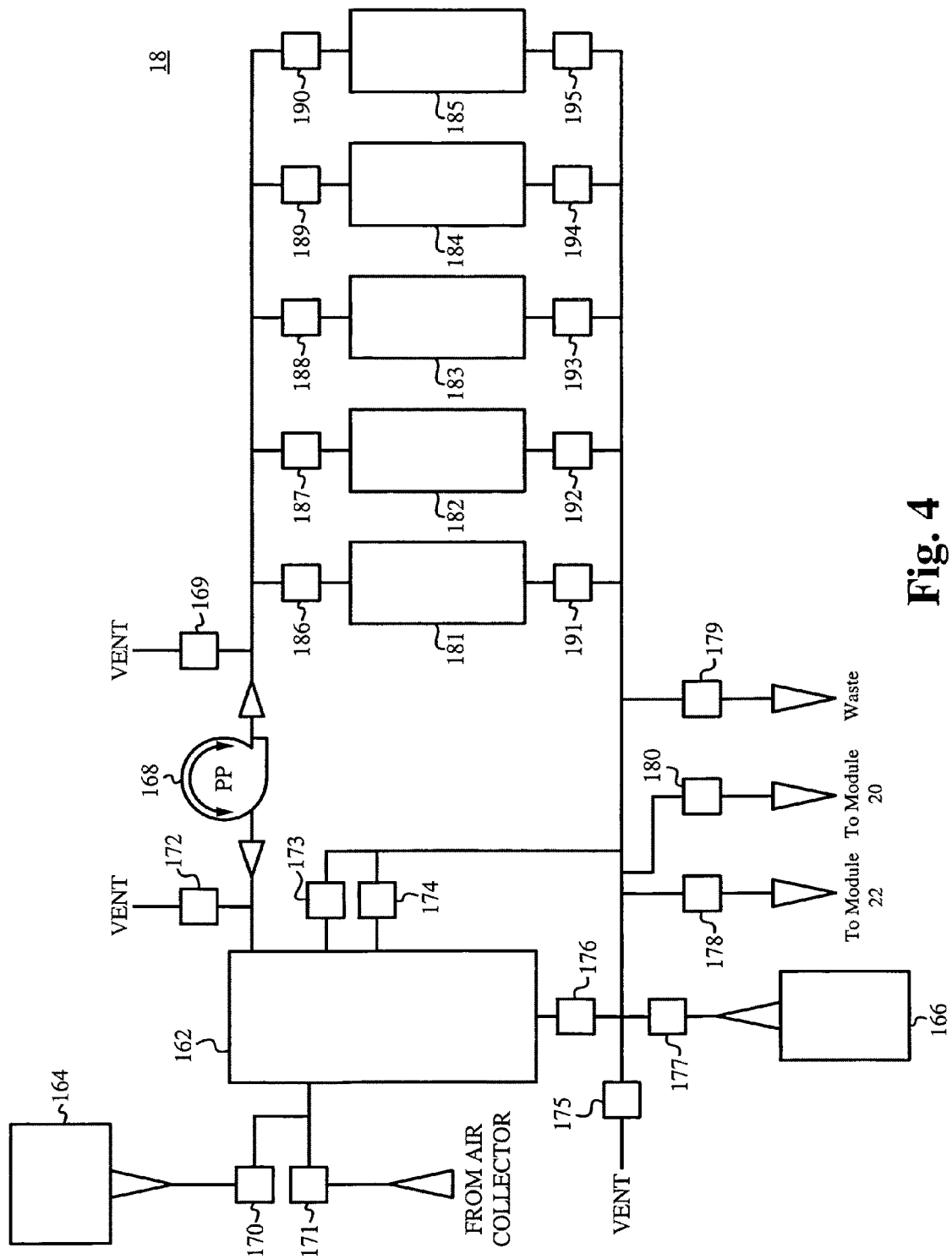
FIG. 4 illustrates an exemplary schematic diagram of the archive module.

FIG. 4 illustrates an exemplary schematic diagram of the distribution module 16 coupled to the archive module 18. In this exemplary configuration, the distribution module 16 includes a metering module 162, a wash syringe 164, a syringe pump 166, and a peristaltic pump 168 coupled together via microfluidic circuitry including valves 169-180. The archive module 18 includes five archive chambers 181-185 coupled to the distribution module 16 via microfluidic circuitry including the valves 186-195.

The fluid sample provided by the air collection module 14 is stored in the metering module 162. In general, the amount of fluid sample provided by the air collection module 14 is an inconsistent amount. In one embodiment, the collection and detection system 10 is configured to process a specific amount of fluid sample, in this case 10 ml. As such, a first step is to remove excess fluid sample from the metering module 162. As applied to the configuration of FIG. 4, any excess fluid sample is removed from the metering module 162 by opening the valve 173 and the valve 179, which enables any excess fluid sample to flow to waste. Remaining is the specific amount of fluid sample in the metering module 162.

Each archive chamber 181-185 is configured to store a predetermined amount of fluid sample. In one embodiment, each archive module 181-185 is configured to store 1 ml. This predetermined amount of fluid sample is metered from the metering module 162 and delivered to one of the archive chambers 181-185 by opening the valves 174 and 169 and the valves corresponding to the archive chamber, such as the valves 186 and 191 for archive chamber 181, turning on the peristaltic pump 168 in a first direction, which forces air from the vent at the valve 169 into the metering module 162. This pressurizes the metering module 162 thereby forcing the fluid sample within through the open valves 174 and 191 and into the archive module 181.

One archive chamber stores the fluid sample for the current cycle, and the remaining four archive chambers store the fluid samples from the previous four cycles. During the next cycle, the oldest fluid sample in the archive is removed and replaced by the next fluid sample. For example, during a first cycle, a first fluid sample is received from the distribution module 16 and stored in the archive chamber 181. During a second cycle, a second fluid sample is received and stored in the archive chamber 182. During a third cycle, a third fluid sample is received and stored in the archive chamber 183. During a fourth cycle, a fourth fluid sample is received and stored in the archive chamber 184. During a fifth cycle, a fifth fluid sample is received and stored in the archive chamber 185. During a sixth cycle, the first fluid sample stored in the archive chamber 181 is first purged to waste. To purge the fluid sample from the archive chamber 181, the valves 172, 186, 191, and 179 are opened and the peristaltic pump 168 is run in a second direction, which forces air from the vent at the valve 172 into the archive chamber 181. This pressurizes the archive chamber 181 thereby forcing the fluid sample within through the open valves 191 and 179 to waste. The valves 172, 186, 191, and 179 are then closed and the archive chamber 181 is then washed using solution provided via the wash syringe 164. The sixth fluid sample is then provided from the distribution module 16 to the empty archive chamber 181. Subsequent fluid samples are stored in a similar manner such that the most recent five fluid samples are archived in the archive module 18.

After the first portion of the fluid sample in the metering module 162 is archived, the remaining fluid sample is metered and distributed to the toxin capture and detection module 22 and the lysis and capture module 20. To meter and distribute a second portion of the fluid sample to the toxin capture and detection module 22, the valves 172, 176, and 177 are opened and the syringe pump 166 is turned on in a first direction to intake the second portion through the open valves 176 and 177 into the syringe pump 166. The valves 172 and 176 are then closed, the valve 177 remains open, and the valve 178 is opened. The syringe pump 166 is turned on in a second direction to force the second portion of the fluid sample from the syringe pump 166 through the open valves 177 and 178 to the toxin capture and detection module 22.

To meter and distribute a third portion of the fluid sample to the lysis and capture module 20, the valves 172, 176, and 177 are opened and the syringe pump 166 is turned on in the first direction to intake the third portion through the open valves 176 and 177 into the syringe pump 166. The valves 172 and 176 are then closed, the valve 177 remains open, and the valve 180 is opened. The syringe pump 166 is turned on in the second direction to force the third portion of the fluid sample from the syringe pump 166 through the open valves 177 and 180 to the lysis and capture module 20. The syringe pump 166 is programmable to withdraw any amount of fluid sample as is required by the application. This adds flexibility in determining how much fluid sample is provided to the toxin capture and detection module 22 and the lysis and capture module 20. In one embodiment, the second portion of fluid sample is 3 ml and the third portion of fluid sample is 6 ml.

Although the archive module is shown in FIG. 4 as including five archive chambers, the archive module can be configured to include more or less than five archive modules. Further, the archiving methodology described above is for exemplary purposes only and any conventional methodology can be used to purge and store subsequent fluid samples. Still further, the metering and distribution configuration and methodology described above in relation to FIG. 4 is but one embodiment. It is understood that other configurations and methodologies are contemplated for metering and distributing any number of fluid sample portions in any denomination.

Figure 5:
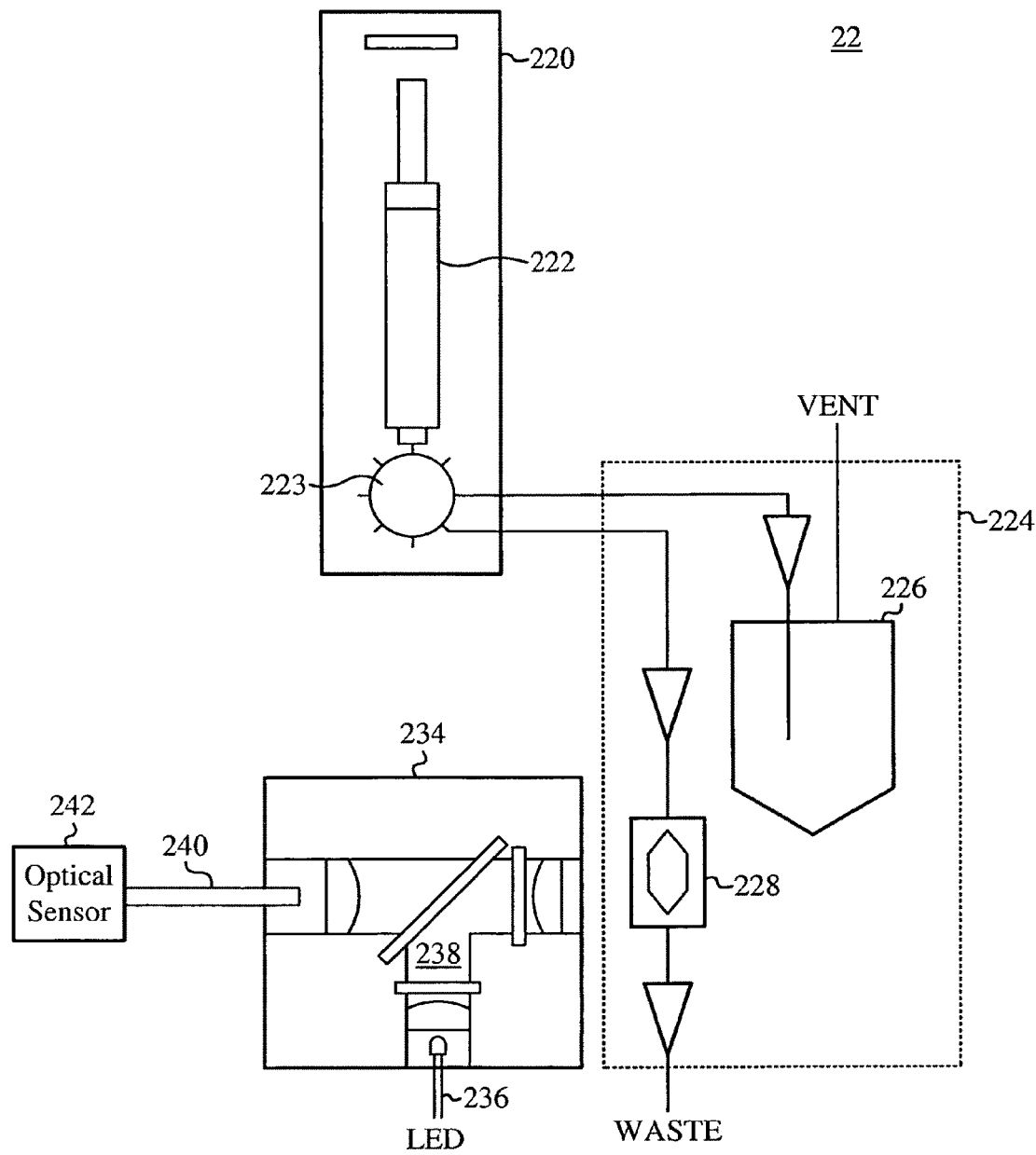
FIG. 5 illustrates an exemplary schematic diagram of the toxin capture and detection module.

FIG. 5 illustrates an exemplary schematic diagram of the toxin capture and detection module 22. The toxin capture and detection module 22 includes a pump assembly including a syringe pump 222 and a distribution valve 223, a capture module 224, and an optical detection module 234. The capture module 224 includes a capture device 228 and a reservoir 226. The fluid sample provided by the distribution module 16 is received by the distribution valve 223 and directed to the capture module 224, where the fluid sample flows through the capture device 228. The distribution valve 223 is also connected to one or more reagent vessels within the solutions module 26.

In one embodiment, the capture device 228 is a capture chip including a plurality of pillars configured such that fluid flows around the pillars making contact therewith. The pillars are prepared such that specific toxins within the fluid sample adhere to the surface of the pillars as the fluid flows past. The fluid sample flows through the capture chip 228 and outputs the capture module 224 to waste, while any of the specific toxins present in the fluid sample remain in the capture chip 228. In one embodiment, each pillar is pre-coated with a particular antibody. Each antibody adheres to a particular type of toxin. When the fluid sample flows past the pillars, the specific toxin present within the fluid sample adheres to the antibody on the pillars. An example of the capture chip 228 is described in U.S. Pat. Nos. 5,707,799 and 5,952,173, which are both hereby incorporated by reference.

In alternative embodiments, the pillars are pre-coated with more than one type of antibody such that each capture chip captures more than one different type of toxin. More than one capture chip can be coupled in series or in parallel to further diversify and expand the different types of toxins collected. For example, a first capture chip in a sequence is pre-coated with a first antibody, a second capture chip in the sequence is pre-coated with a second antibody, and so on for as many capture chips in the series. Additionally, one, some, or all of the capture chips in the series can be pre-coated with more than one antibody. For example, a capture chip can be pre-coated with multiple antibodies. Each antibody to adhere to a specific type of toxin. The different captured toxins can then be distinguished according to a distinguishing characteristic, such as different optical wavelengths. In a series configuration, the fluid sample flows in series from the first capture chip to the second capture chip and so on. Although the capture device 228 is described above as a capture chip, the capture device 228 can be any conventional device capable of capturing one or more toxins.

The toxin capture and detection module 22 includes the optical detector 234 coupled to the capture device 228. The capture device 228 is configured such that the toxin captured within is optically accessible to the optical detector 234. In one embodiment, the capture device 228 includes an optically transparent lid. Alternatively, the captured toxin is eluted from the capture device 228 and collected in a separate collection means, such as a vessel or reservoir. Optical detection can then be performed on the eluted toxin in the collection means.

In this embodiment, the optical detector 234 includes a light source 236, such as an LED or a laser, an optical pathway 238, such as one or more lenses, filters and beam splitters, a fiber optics 240, and an optical sensor 242. The optical detector 234 is configured to direct light onto the capture device 228, and to collect and measure characteristics of the light reflected back. The characteristics of the reflected light are used to identify the toxin(s) captured in the capture device 228. The configuration of the optical detector 234 shown in FIG. 5 is for exemplary purposes only. In some embodiments, the optical detector 234 is configured to include a light source, an optical pathway to direct the light onto a specific location of the capture device 228 and to direct the reflected light from the capture device 228 to an optical detector, and the optical detector. In other embodiments, a light source is not included. In such cases, light is emitted from the captured toxins, such as by chemi-luminescence. The emitted light is detected by the optical sensor. In one embodiment, the optical detector is any conventional optical detection device capable of measuring one or more disparate wavelengths. The measured characteristics are provided from the optical detector 234 to the control module 12 for analysis.

In some embodiments, a toxin captured in the capture device 228 is identified by forming a sandwich assay, including a flourescent marker, and then detecting the flourescent marker. The flourescent marker is optically detectable using the optical detector 234. Each type of toxin is associated with a specific type of flourescent marker. It is understood that other conventional means for marking and identifying the toxin can be used.

Once the captured toxins are interrogated by the optical detector 234, the capture device 228 is washed using washing solutions provided from the solutions module 26 and directed to the capture device 228. The washing solutions are received from the solutions module 26 by the distribution valve 223.

Where the capture device 228 comprises multiple capture devices coupled in series, each device in series is coupled to a corresponding optical detector of the type described above.

Figure 6:
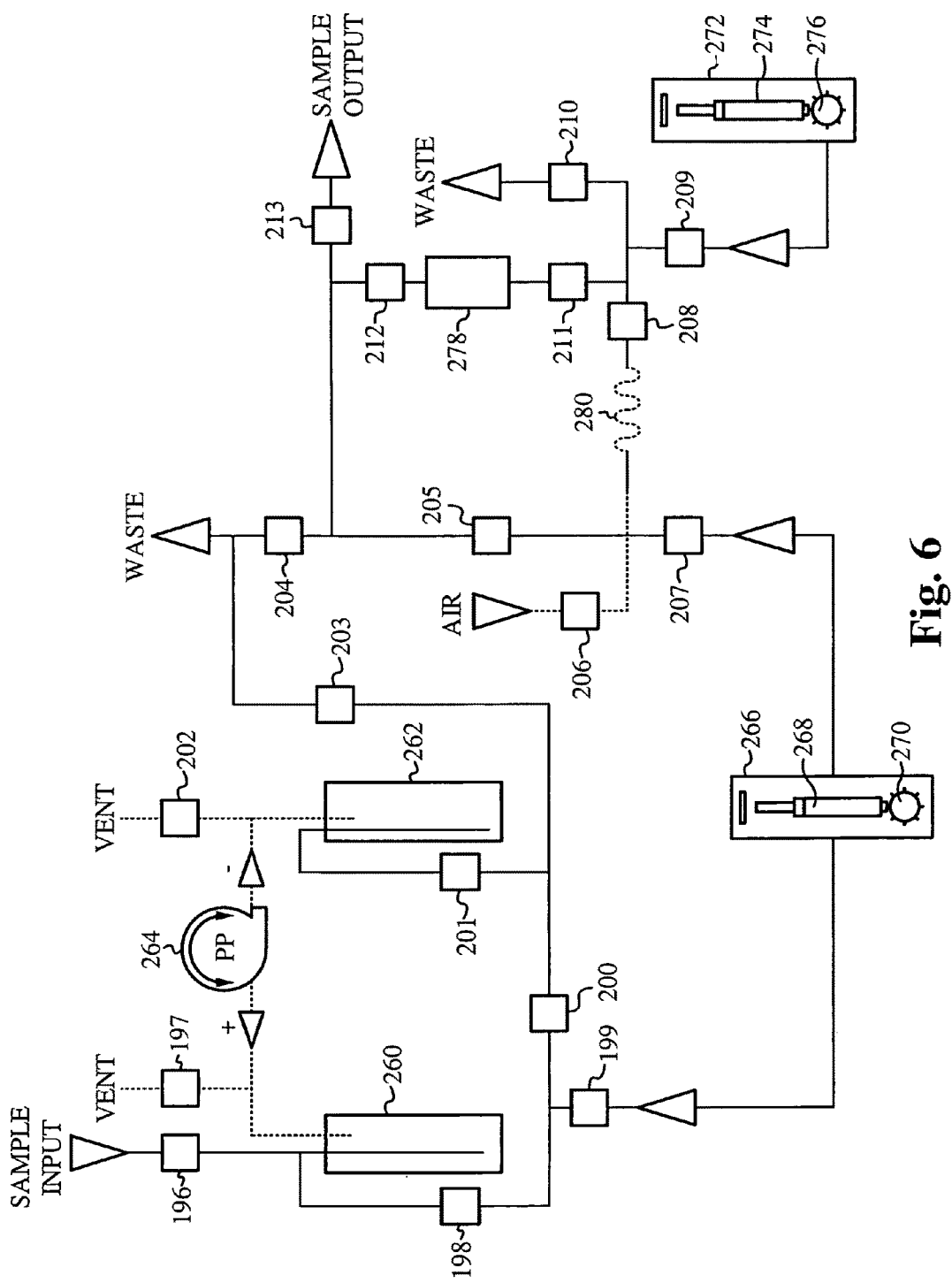
FIG. 6 illustrates an exemplary schematic diagram of the lysis and capture module.

FIG. 6 illustrates an exemplary schematic diagram of the lysis and capture module 20. The lysis and capture module 20 is configured to lyse cells present in the fluid sample, and to capture the nucleic acids of the lysed cells. The lysis and capture module 20 includes a lysis chamber 260, a mixing chamber 262, a peristaltic pump 264, a pump assembly 266 including a syringe pump 268 and a distribution valve 270, a pump assembly 272 including a syringe pump 274 and a distribution valve 276, a purification device 278, a cooling element 280, such as a thermal electric cooler, and valves 196-213. The microfluidic circuitry including the peristaltic pump 264, the pump assembly 266, the pump assembly 272, and the valves 196-213 are configured to direct the fluid sample through the lysis and capture module 20, as well as to direct the various solutions used in processing and decontamination. The mixing chamber 262 is configured for mixing and holding solutions. For example, in some applications, one or more additional solutions are added to the fluid sample prior to lysing, and/or one or more additional solutions are added after lysing.

The peristaltic pump 264 is configured to pressurize either the lysis chamber 260, which forces fluid from the lysis chamber 260 to the mixing chamber 262, or to pressurize the mixing chamber 262, which forces fluid from the mixing chamber 262 to the lysis chamber 260. During either operation, the appropriate valves are opened to enable such fluid flow.

The fluid sample provided by the distribution module 16 is directed to the lysis chamber 260. In one embodiment, lysis is performed using sonication. In some embodiments, selective lysis is performed where specific types of cells are lysed at different sonication energies. In this embodiment, the lysis and capture module 20 is configured to selectively lyse a specific type of cell at a corresponding sonication energy. The lysed cells are then separated from the fluid sample. Additional sonication steps can be performed on the remaining fluid sample to selectively lyse one or more additional cell types. An exemplary apparatus and method for performing such a selective lysis process is described in the co-pending and co-owned U.S. patent application Ser. No. 10/943,601, filed on Sep. 17, 2004, and entitled "Microfluidic Differential Extraction Cartridge," which is hereby incorporated in its entirety by reference. Alternatively, other conventional lysis methods are utilized, such as heating and/or chemical treatment.

The pump assembly 266 is configured to direct the lysed fluid sample through the cooling element 280 and the purification device 278 to waste via the valve 204. Nucleic acid within the lysate is purified and concentrated as the lysate flows through the purification device 278.

In one embodiment, the purification device 278 is a purification chip including a plurality of pillars configured such that fluid flows around the pillars making contact therewith. Nucleic acid is known to be attracted to silicon. In one embodiment, the pillars within the purification chip are comprised of silicon such that as the fluid flows past the pillars, nucleic acid within the fluid adheres to the pillars. Alternatively, the pillars are comprised of a material other than silicon and are coated with silicon. Still alternatively, the pillars are comprised of or coated with a material to which nucleic acid adheres. The fluid sample flows through the purification chip 278 and outputs the lysis and capture module 20 to waste, while nucleic acid present in the fluid sample remains in the purification chip 278. An example of the purification chip 278 is also described in U.S. Pat. Nos. 5,707,799 and 5,952,173. More than one purification chip 278 can be coupled in series or in parallel. In a series configuration for example, the fluid sample flows through a first purification chip in the series to a second purification chip and so on. Although the purification device 278 is described above as a purification chip, the purification device 278 can be any conventional device capable of capturing nucleic acid.

The pump assembly 266 is also configured to direct a wash solution through the purification device 278 to remove residual fluid sample solution. The wash solution is provided from the solutions module 24 via the distribution valve 270 and is directed to waste via the valve 84. Air is then blown through the purification device 228 to remove residual wash solution. The captured nucleic acids are removed from the purification device 278 using an elution buffer. The pump assembly 272 is configured to direct the elution buffer from the solutions module 24 through the purification device 278 to elute the nucleic acid. A purified and concentrated nucleic acid solution is output from the purification device 278 and output from the lysis and capture module 20 via the valve 213. In one embodiment, a heating element (not shown) is coupled to the purification device 278. Prior to eluting the nucleic acid from the purification device 278, the heating element heats the purification device 278, which facilitates the elution process.

The lysis and capture module 20 is also configured to back-flush the purification device 278, either to un-block the device or as part of wash and decontamination process. The microfluidic circuitry is configured to direct wash solution backwards through the purification device 278 and out to waste via the valve 210.

Figure 7:
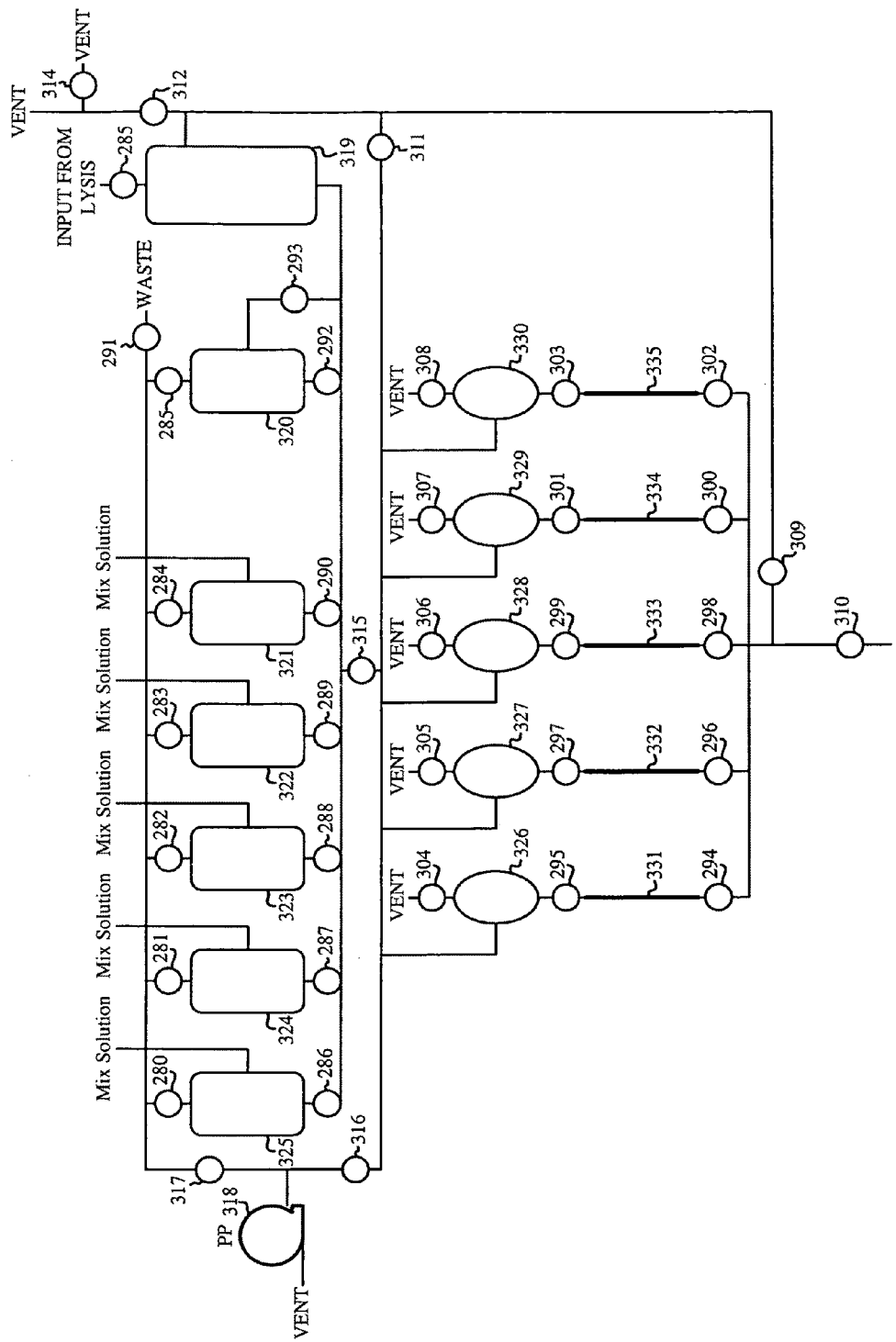
FIG. 7 illustrates an exemplary schematic diagram of the metering and thermal cycling module.

FIG. 7 illustrates an exemplary schematic diagram of the metering and thermal cycling module 30. The metering and thermal cycling module 30 is configured to pre-amplify and amplify any nucleic acid present in the nucleic acid solution provided by the lysis and capture module 20. The metering and thermal cycling module 30 is also configured to tag one or more specific types of nucleic acids if present within the amplified nucleic acid solution. The one or more specific acids are tagged using a conjugated antibody solution including a different flourescent marker for each specific nucleic acid. The metering and thermal cycling module 30 includes a plurality of solution reservoirs 321-325, a holding reservoir 319, a metering reservoir 320, a plurality of valves 280-317, a peristaltic pump 318, a plurality of thermal cycling chambers 331-335, and a plurality of mixing reservoirs 326-330.

Each of the plurality of solution reservoirs 321-325 are coupled to the solutions module 32 and are configured to store a specific amount of master mix solution received from the solutions module 32. The holding reservoir 319 is configured to store the nucleic acid solution output from the lysis and capture module 20. The metering reservoir 320 is configured to meter and to store a specific amount of the nucleic acid solution from the holding reservoir 319. In one embodiment, each of the solution reservoirs 321-325 are configured to store 15 ul, and the metering reservoir is configured to store 10 ul. A first metered portion of the nucleic acid solution is directed from the fluid metering reservoir 320 to the mixing reservoir 326, and the specific amount of mixing solution from the holding reservoir 325 is directed to the mixing reservoir 326. A second portion of the nucleic acid solution is then metered and stored in the metering reservoir 320. The second metered portion is directed from the metering reservoir 320 to the mixing reservoir 327, and the specific amount of mixing solution from the holding reservoir 324 is directed to the mixing reservoir 327. A metered portion of the nucleic acid solution and a specified amount of the mixing solution is provided to each of the remaining mixing reservoirs 328-330 in a similar manner.

The mixed solution in the mixing reservoir 326 is directed to the thermal cycling chamber 331, the mixed solution in the mixing reservoir 327 is directed to the thermal cycling chamber 332, the mixed solution in the mixing reservoir 328 is directed to the thermal cycling chamber 333, the mixed solution in the mixing reservoir 329 is directed to the thermal cycling chamber 334, and the mixed solution in the mixing reservoir 330 is directed to the thermal cycling chamber 335. A heating element (not shown) is coupled to each of the thermal cycling chambers to perform a thermal cycling process. In one embodiment, the thermal cycling chambers 331-335 are configured as elongated tubes capped at a each end by a valve, and the tubes are coupled to a heating mesh to form a heating and tube assembly. An example of such a heating and tube assembly is described in the co-owned and co-pending U.S. patent application Ser. No. 11/201,615, filed on Aug. 10, 2005, and entitled "Disposable Integrated Heater and Tube Assembly for Thermally-driven Chemical Reactions," which is hereby incorporated by reference.

The microfluidic circuitry within the metering and thermal cycling module 30 is configured such that multiple different thermal cycling processes can be performed. After a first thermal cycling process is performed on a first mixed solution, as described above, the resulting solutions in the thermal cycling chambers 331-335 are back-flushed into the corresponding mixing reservoirs 326-330. Alternatively, additional microfluidic circuitry is provided which directs solutions from the thermal cycling chambers 331-335 to their respective mixing reservoirs 326-330. Additional mixing solutions can be provided to the mixing reservoirs 326-330 from the solution reservoirs 321-325. The mixing solutions provided during this step can be the same or different than the mixing solutions provided during the first thermal cycling process. The mixed solutions are then directed back to the thermal cycling chambers 331-335 for a second thermal cycling process. Additional thermal cycling processes can be performed in this manner. In one application, a pre-amplification process is performed during the first thermal cycling process and an amplification process is performed during the second thermal cycling process. An example of one such pre-amplification and amplification process is described in the co-pending, co-owned U.S. patent application Ser. No. 11/509,868, filed Aug. 24, 2006, and entitled "A Method for Detecting Multiple Limited Copy Targets", which is hereby incorporated by reference. The amplification process results in an amplified nucleic acid solution. The amplified nucleic acid solution is output from the metering and thermal cycling module 30.

One or more additional processing steps can be performed on the amplified nucleic acid solution prior to being output from the metering and thermal cycling module 30. Such additional processing steps prepare the amplified nucleic acid solution for interrogation by the optical detection module 34. The amplified nucleic acid solution is back-flushed from the thermal cycling chambers 331-335 to the corresponding mixing reservoirs 326-330. An additional solution is added to each of the mixing reservoirs. The additional solution is configured to adhere to one or more specific types of nucleic acids if present within the amplified nucleic acid solution. The resulting product includes a different flourescent marker for each specific nucleic acid. This product is then output from the metering and thermal cycling module 30. It is understood that alternative chemistries can be used to detect the presence of the specific types of nucleic acids.

Although the metering and thermal cycling module 30 shown in FIG. 7 is configured with five thermal cycling chambers, five mixing reservoirs, and five solution reservoirs, the metering and thermal cycling module 30 can be configured with more or less than five thermal cycling chambers, five mixing reservoirs, and five solution reservoirs. Still alternatively, an alternative mixing method eliminates the mixing reservoirs and relies on mixing within the fluid lines themselves during transport of the fluids from the solutions reservoirs to the thermal cycling chambers.

Figure 8:
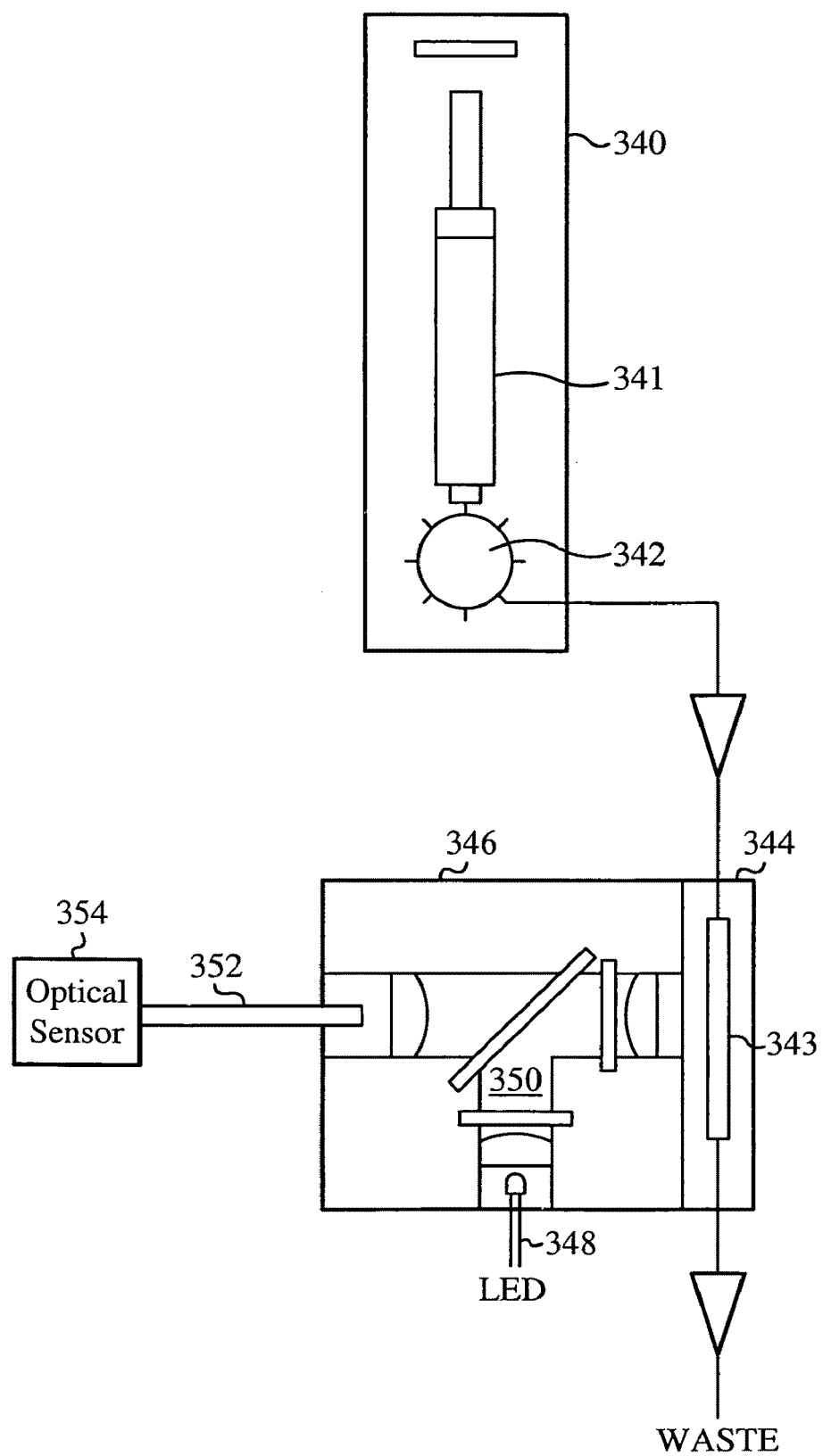
FIG. 8 illustrates an exemplary schematic diagram of the optical detection module.

FIG. 8 illustrates an exemplary schematic diagram of the optical detection module 34. The optical detection module 34 includes a pump assembly 340 including a syringe pump 341 and a distribution valve 342, a fluid line 344 including an interrogation channel 343, and an optical detector 346. The fluid line 344 receives the amplified nucleic acid solution output from the metering and thermal cycling module 30. The interrogation channel 343 is an optically transparent portion of the fluid line 344 that enables optical analysis to be performed by the optical detector 346 as the amplified nucleic acid solution passes through the optically transparent portion. In one embodiment, the interrogation channel 343 is integrated within the microfluidic circuitry connecting the metering and thermal cycling module 30 to the waste module 28 (FIG. 2). In this configuration, optical measurements are taken of the amplified nucleic acid solution as the solution is directed to waste. Alternatively, a collection vessel is coupled to the fluid line 344, and the amplified nucleic acid solution is colleted in the collection vessel, where optical measurements are taken.

The optical detector 346 includes a light source 348, such as a white-light LED or a laser, an optical pathway 350, such as one or more lenses, filters and beam splitters, a fiber optics 352, and an optical sensor 354. The optical detector 346 is functionally equivalent to the optical detector 234 (FIG. 5) in the toxin capture and detect module 22. The optical detector 346 is configured to direct light into the interrogation channel 343, and to collect and measure characteristics of the light reflected back. The characteristics of the reflected light are used to determine if specific types of nucleic acids are present in the amplified nucleic acid solution. The configuration of the optical detector 346 shown in FIG. 8 is for exemplary purposes only. In some embodiments, the optical detector 346 is configured to include a light source, an optical pathway to direct the light onto the interrogation channel 343 and to direct the reflected light from the interrogation channel 343 to an optical detector, and the optical detector. In other embodiments, a light source is not included. In such cases, light is emitted from the captured toxins, such as by chemi-luminescence. The emitted light is detected by the optical sensor. In one embodiment, the optical detector is any conventional optical detection device capable of measuring one or more disparate wavelengths. The measured characteristics are provided from the optical detector 346 to the control module 12 for analysis.

Figure 9:
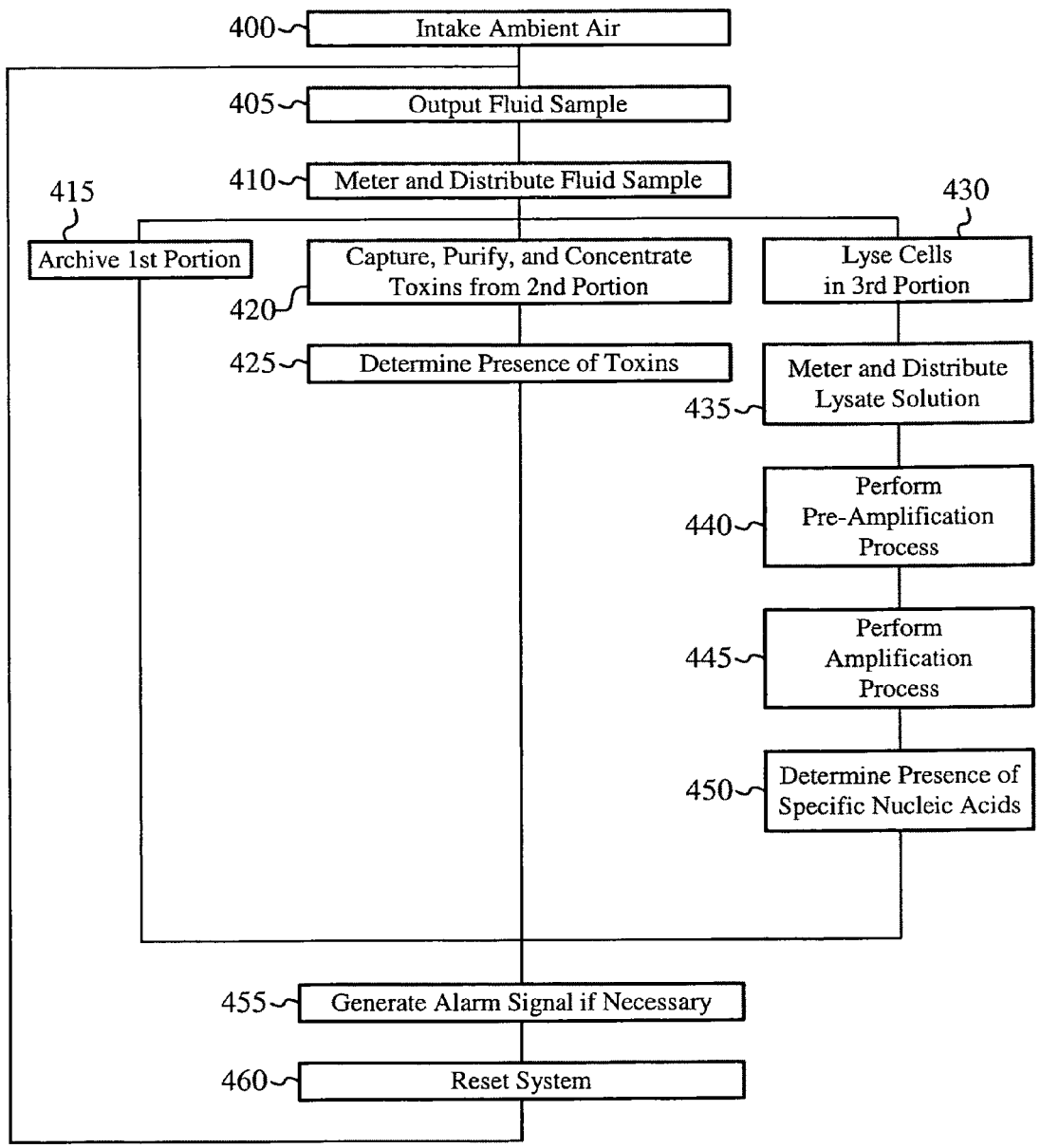
FIG. 9 illustrates an exemplary automated process performed by the first embodiment of the particle collection and detection system.

The particle collection and detection system 10 is a fully integrated and automated system configured to detect the presence of specific airborne particles. FIG. 9 illustrates an exemplary automated process performed by the particle collection and detection system 10. At the step 400, intake ambient air into the air collection module 14. Air is continuously taking in by the air collection module 14 throughout the entire process. At the step 405, periodically output a fluid sample from the air collection module 14 according to a defined schedule. The output fluid sample includes airborne particles collected from the ambient air. At the step 410, meter and distribute the fluid sample. At the step 415, archive a first portion of the fluid sample. At the step 420, capture, purify and concentrate toxins from within a second portion of the fluid sample. At the step 425, determine the presence of toxins captured in the step 420. In one embodiment, optical detection is used to detect the presence of toxins.

At the step 430, lyse cells in a third portion of the fluid sample. This generates a lysate solution. At the step 435, meter and distribute the lysate solution. At the step 440, perform a pre-amplification process on each metered portion of the first lysate. At the step 445, perform an amplification process on each metered portion of the first lysate to generate an amplified nucleic acid solution. The pre-amplification process and the amplification process include thermal cycling. At the step 450, determine the presence of one or more specific types of nucleic acids in the amplified nucleic acid solution and identifying the one or more specific types of nucleic acids. The steps 430 through 450 are performed in parallel with the steps 420 through 425, thereby simultaneously processing the fluid sample.

At the step 455, generate an alarm signal if one or more toxins are determined at the step 425 or one or more specific nucleic acids are determined at the step 450. At the step 460, reset the system to process the next fluid sample to be output by the air collection module 14. The system is reset by decontaminating the microfluidic circuitry through which the fluid sample passed, any fluid sample collection vessels, the capture devices used to capture the toxins, the purification devices used to purify the nucleic acids, any purged archive chambers, and the thermal cycling chambers. Decontamination is performed using any conventional rinsing and washing steps. After the system is reset, and at the next scheduled interval, the next fluid sample is output from the air collection module 14 and processed as described above. This process is continuously repeated for successive fluid samples. The particle collection and detection system functions independently, or is networked to a remote monitoring and/or control location to which measured characteristics and/or post-analysis results are transmitted and/or from which control signals are received.

In an exemplary application, the collection and detection system 10 operates continuously 24 hours a day, 7 days a week. Every three hours the air collection module outputs a 10 ml fluid sample to the distribution module 16. 1 ml of the 10 ml fluid sample is metered and distributed to the archive module 18, 3 ml to the toxin capture and detection module 22, and 6 ml to the lysis and capture module 20. The lysis and capture module 20 outputs a 50 ul sample for each 6 ml input sample. The metering and thermal cycling module 30 receives as input the 50 ul sample from the lysis and capture module 20 and 15 ul aliquots from the solutions module 32. The metering and thermal cycling module 30 outputs five, 25 ul samples for each 50 ul input sample received from the lysis and capture module 20. Each of the five, 25 ul samples are analyzed by the optical detection module 34. The above timing, sample sizes, and distribution ratios are for exemplary purposes only. The specific timing, sample sizes, and distribution ratios are application specific and the collection and detection system 10 is configured accordingly. Positive and negative control samples can be substituted for one or more of the 25 ul fluid samples processed by the metering and thermal cycling module 30, thereby verifying the accuracy of the analysis performed on any given input fluid sample.

Figure 10:
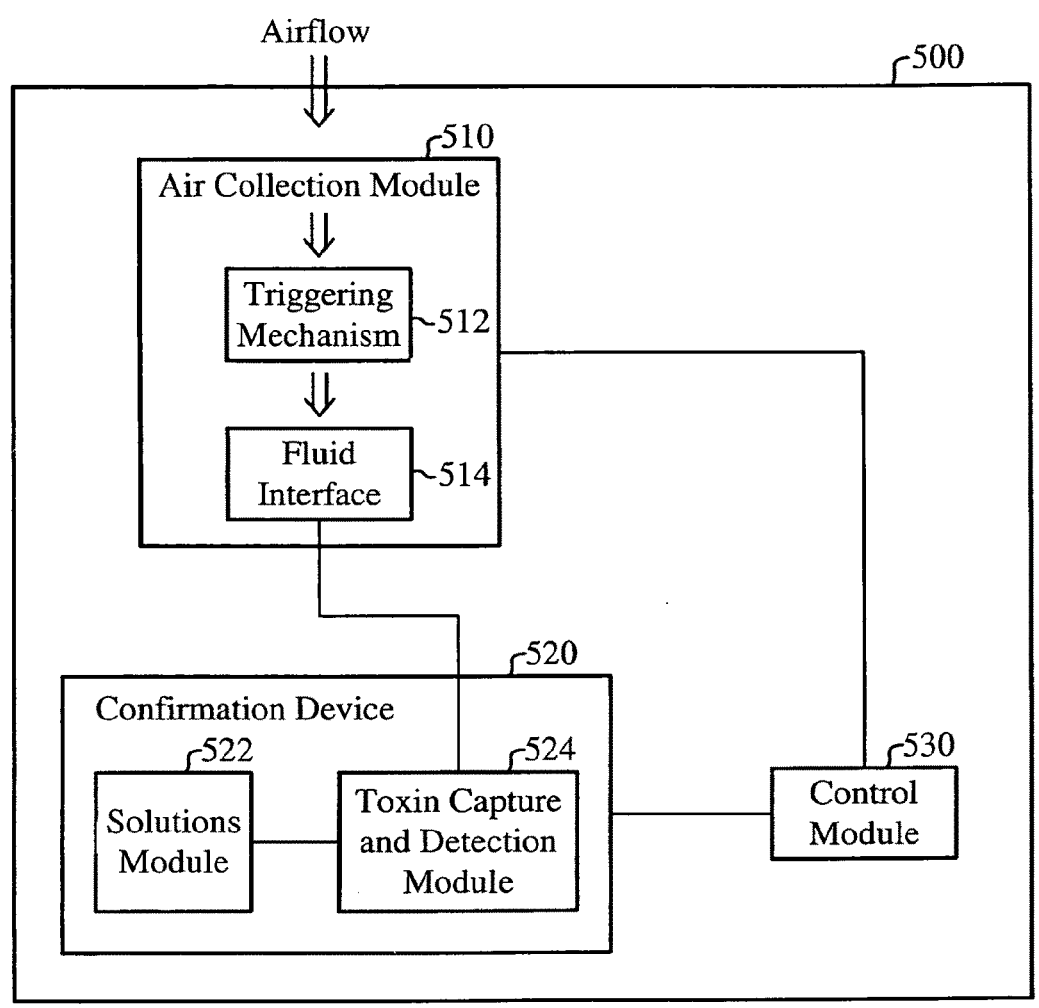
FIG. 10 illustrates an exemplary functional block diagram of the second embodiment of the integrated collection and detection system.

A second embodiment of a collection and detection system is directed to a detect to warn system in which the presence of specific types of particles are detected, and may or may not be identified. FIG. 10 illustrates an exemplary functional block diagram of the second embodiment of the integrated collection and detection system. The integrated collection and detection system 500 includes an air collection module 510, a confirmation device 520, and a control module 530. Fluid is directed between the fluid interface 514 and the confirmation device 520, and within the confirmation device 520, using microfluidic circuitry.

The air collection module 510 is configured to intake ambient air, detect the presence of one or more different types of airborne particles within the ambient air, and collect the airborne particles, such as within a fluid. The air collection module 510 includes a triggering mechanism 512 and a fluid interface 514. The fluid interface 514 is configured to receive ambient air, including airborne particles present therein, that is drawn into the collection and detection system 500 and to collect the airborne particles into a fluid solution, also referred to as a fluid sample. The fluid interface 500 includes a fan to generate airflow into the collection and detection system 500. In some embodiments, the airborne particles are collected by eluting particles collected on the fan and then collecting the resulting fluid solution including the eluted particles. One such method of collecting the airborne particles into a fluid solution is described in the co-owned, co-pending U.S. patent application Ser. No. 11/509,878, filed Aug. 24, 2006, and entitled "Automated Particle Collection Off of Fan Blades into a Liquid Buffer," which is hereby incorporated by reference. The fluid solution can be stored in a collection vessel within the fluid interface 514, or in a collection vessel external to the fluid interface 514 and/or the air collection module 510.

The triggering mechanism 514 is positioned to continuously monitor the airflow, and the airborne particles within the airflow, directed to the fluid interface 514. The triggering mechanism 512 includes a light source, such as a laser or a white-light LED, to generate a light beam that is directed at the airflow. The light beam impinges the airborne particles within the airflow. The triggering mechanism 512 also includes a light collector, such as an optical sensor, to measure one or more optical characteristics associated with the light after impinging the airborne particles. In some embodiments, the wavelength of the light reflected off the airborne particles is measured. The triggering mechanism 512 is non-destructive in relation to the airborne particles.

The optical characteristics measured by the triggering mechanism 512 are provided to the control module 530. The optical characteristics are compared to known optical characteristics by the control module 530 to determine if one or more different types of specific biological particles are present in the airflow. If it is determined that one or more different types of specific biological particles are present, than a trigger signal is generated by the control module 530. Alternatively, the triggering mechanism 512 includes logic circuitry to determine if one or more different types of specific biological particles are present and to generate the trigger signal, if necessary. Still alternatively, the triggering mechanism 512 includes logic circuitry to determine if one or more different types of specific biological particles are present, and the control module 530 generates the trigger signal, if necessary.

In response to the trigger signal, the fluid sample, or a portion thereof, is directed to the confirmation device 520 to confirm the presence of the one or more different types of specific biological particles. The confirmation device 520 includes a solutions module 522 and a toxin capture and detection module 524.

The toxin capture and detection module 524 of the second embodiment is physically and operationally equivalent to the toxin capture and detection module 22 of the first embodiment with the exception that the one or more capture devices and the optical detection module within the toxin capture and detection module 524 are configured to capture and detect specific pathogens in addition to specific toxins. Some pathogens are detectable using immuno assay. In some embodiments, the one or more capture devices within the toxin capture and detection module 524 are pre-coated with one or more specific antibodies known to adhere to specific pathogens, in addition to the one or more specific antibodies known to adhere to specific toxins as described in relation to the toxin capture and detection module 22. In these embodiments, the optical detection module within the toxin capture and detection module 524 is configured to measure one or more optical characteristics of any captured toxin or pathogen, which are used to determine the presence of each of the specific antibodies.

The raw data obtained by the toxin capture and detection module 524, such as the measured optical characteristics, is provided to the control module 530, where it is used to determine the presence and identity of one or more specific types of toxins and/or pathogens. If a specific toxin or pathogen is detected, the control module 530 generates an alarm signal. Alternatively, the raw data collected by the toxin capture and detection module 524 is sent to a remote location, such as the central monitoring point 50 (FIG. 1) for analysis.

The solutions module 522 is similar to the solutions module 26 (FIG. 2) in that it provides solutions used during the capture steps performed in the toxin capture and detection module 524. For example, the solutions module 522 includes wash solutions and antibody solutions.

The collection and detection system 500 is configured to be re-used such that ambient air is continuously interrogated and successive fluid samples output by the air collection module 510 are processed. As such, the toxins capture and detection module 524 and all interconnecting microfluidic circuitry are decontaminated between cycles. Various solutions are used to perform the rinse and wash steps during decontamination, these solutions are included in the solutions module 522.

The control module 530 is coupled to each module to control operation of the collection and detection system 500. Such control enables complete automation of the collection and detection process, without need of human intervention. The control module 530 is also configured to analyze the raw data provided by the toxin capture and detection module 524 and to generate any appropriate alarm or trigger signals. In response to an alarm signal, the control module 530 initiates a localized audio and/or visual alarm and/or transmits a notification signal to a networked local monitoring location or a centralized monitoring location.

The analyzed fluid samples, elution buffers, mixing solutions, rinses, washes, purged archive samples, and other solutions related to the processing of fluid samples and subsequent decontamination of the collection and detection system 500 are directed to a waste module (not shown). Alternatively, fluid samples analyzed and subsequently output by the toxin capture and detection module 524 can be archived, either in a local or a remote storage vessel.

FIG. 11 illustrates an exemplary automated process performed by the particle collection and detection system 500. At the step 540, intake ambient air into the air collection module 510. Air is continuously taken in by the air collection module 510 throughout the entire process. At the step 545, airborne particles within the ambient air are interrogated to measure one or more optical characteristics associated with the airborne particles. In some embodiments, a laser beam is used to interrogate the airborne particles such that the wavelengths of light reflected from the laser beam impinging the airborne particles is measured. At the step 550, the measured optical characteristics are compared to known optical characteristics associated with one or more different types of biological particles. If it is determined that there is not a match at the step 550, then the method repeats the step 540 and 545. If however it is determined that there is a match at the step 550, then at the step 555 a trigger signal is generated. Generation of the trigger signal indicates that at least one type of biological particle is present within the ambient air.

At the step 560, a fluid sample is generated that includes the particles from the ambient air. In response to the trigger signal, the fluid sample, or a portion thereof, is directed to the confirmation device 520. The step 560 can be performed after the step 545 such that the fluid sample is always generated, regardless of a match made between the measured optical characteristics and known optical characteristics. The step 560 can also be performed concurrently with the step 550, and if necessary the step 555. At the step 565, the confirmation device 520 confirms that one or more specific types of biological particles are present. The biological particles are either specific types of toxins or specific types of pathogens. In some embodiments, the confirmation device 520 confirms the presence of one or more different types of toxins and/or pathogens using immuno assays. In some embodiments, the confirmation device 520 identifies one or more of the different types of toxins and/or pathogens. In some embodiments, the confirmation device 520 generates an alarm signal if the presence of one or more different types of toxins and/or pathogens is confirmed.

A third embodiment of a collection and detection system combines the functionality of the collection and detection system 10 of FIG. 1 and the collection and detection system 500 of FIG. 10. In this third embodiment, the collection and detection system 500 is adapted to perform a first level of detection in which the presence of one or more toxins and/or pathogens are detected, and upon such detection, the collection and detection system 500 is adapted to perform a second level of detection in which the one or more toxins and/or pathogens are identified.

Figure 12:
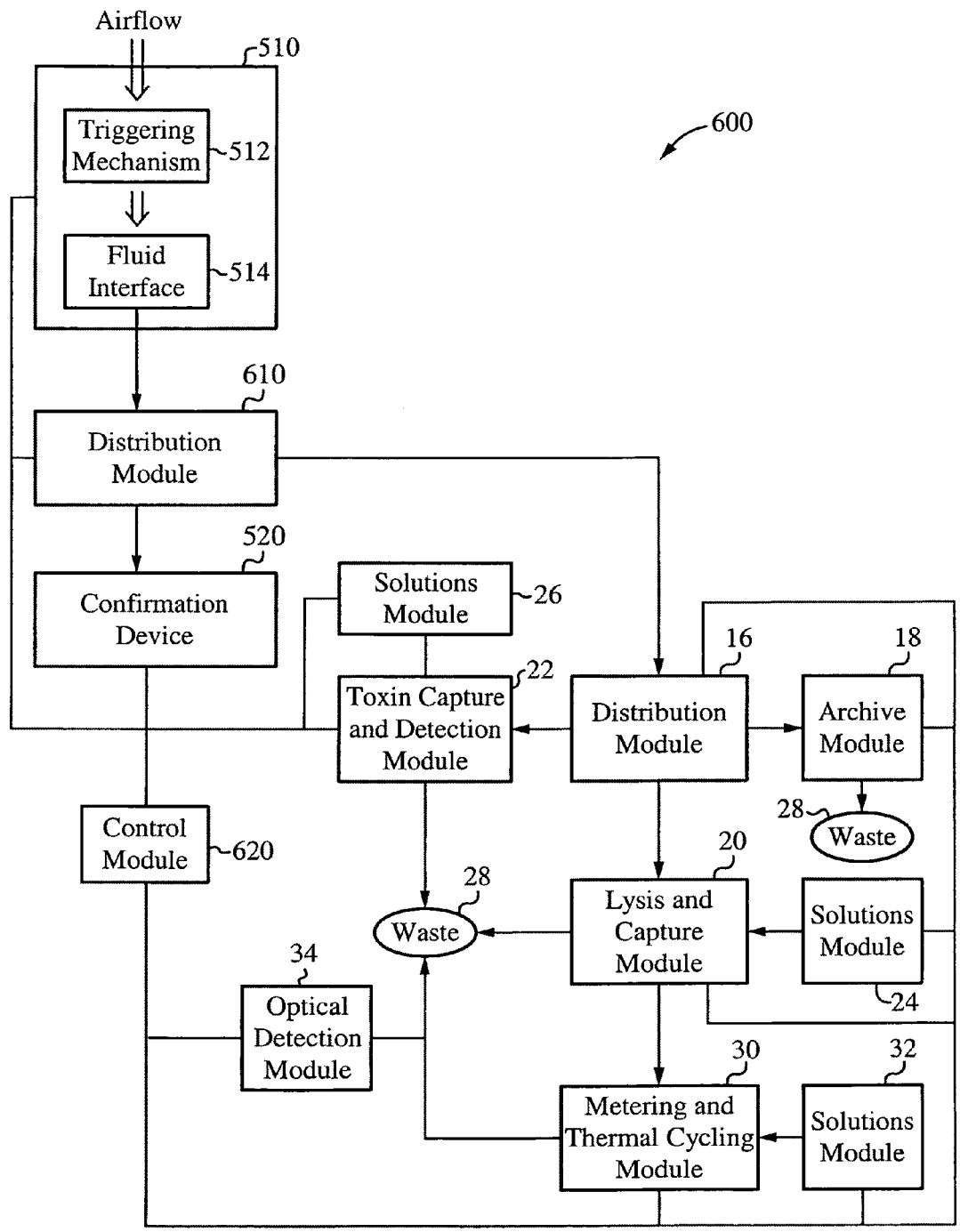
FIG. 12 illustrates an exemplary functional block diagram of the third embodiment of the integrated collection and detection system.

FIG. 12 illustrates an exemplary functional block diagram of the third embodiment of the integrated collection and detection system. The integrated collection and detection system 600 includes the air collection module 510 and the confirmation device 520 of the collection and detection system 500, and the distribution module 16, the archive module 18, the lysis and capture module 20, the toxin capture and detection module 22, the solutions module 24, the solutions module 26, the waste module 28, the metering and thermal cycling module 30, the solutions module 32, and the optical detection module 34 of the collection and detection system 10. The collection and detection system 600 also includes a distribution module 610 and a control module 620. Each of the modules are fluidically coupled as appropriate to direct fluid sample and solutions within the collection and detection system 600.

Control of the collection and detection system 600 is maintained by the control module 620, which includes the functionality of the control module 12 of the collection and detection system 10 and the control module 530 of the collection and detection system 500. Alternatively, control is distributed locally, such as by adding the control module 530 to control the first level of detection and by adding the control module 12 to control the second level of detection. Such local control modules communicate with each other to coordinate their respective functions. Still alternatively, control is distributed locally, such as by adding the control module 530 and the control module 12, and maintaining high-level control over the collection and detection system 600 by a global control module coupled to the local control modules. The control module 620 is coupled to each of the modules in the collection and detection system 600.

The distribution module 610 is configured to receive the fluid sample output from the fluid interface 514. The distribution module 610 includes microfluidic circuitry and storage vessels. The fluid sample received from the fluid interface 514 is metered and distributed according to predetermined ratios. A first portion of the fluid sample is metered and distributed to the confirmation device 520 in response to the trigger signal. The remaining portion of the fluid sample remains stored in the distribution module 610. If the confirmation device 520 confirms the presence of one or more specific types of biological particles, then the alarm signal is generated. In response to the alarm signal, the remaining portion of the fluid sample is distributed from the distribution module 610 to the distribution module 16. The fluid sample is then processed by the toxin capture and detection module 22, the lysis and capture module 20, the metering and thermal cycling module 20, and the optical detection module 34 to identify particles within the fluid sample. In some embodiments, a single distribution module can be configured to combine the functionality of the distribution module 610 and the distribution module 16.

If the triggering mechanism 512 does not generate a trigger signal, the fluid sample is stored in the distribution module 610 until the next scheduled interval for providing the fluid sample to the distribution module 16 to process. If the triggering mechanism 512 does generate a trigger signal but the confirmation device 520 does not generate an alarm signal, the remaining fluid sample is stored in the distribution module 610 until the next scheduled interval. Alternatively, if the triggering mechanism 512 does generate a trigger signal, the remaining fluid sample is distributed to the distribution module 16 to process whether or not the confirmation device 520 generates an alarm signal. The fluid interface 514 continues to output fluid sample to be stored in the distribution module 610 regardless of whether or not the trigger signal or alarm signal are generated.

In operation of the collection and detection system 600, the triggering mechanism 512 and the confirmation device 520 perform a first level of detection that determines if specific types of biological particles are present in the ambient air. If the first level of detection confirms the presence of one or more specific types of biological particles, a second level of detection is performed by the toxin capture and detection module 22, the lysis and capture module 20, the metering and thermal cycling module 20, and the optical detection module 34. The second level of detection identifies one or more specific toxins and/or one or more specific types of pathogens.

Figure 13:
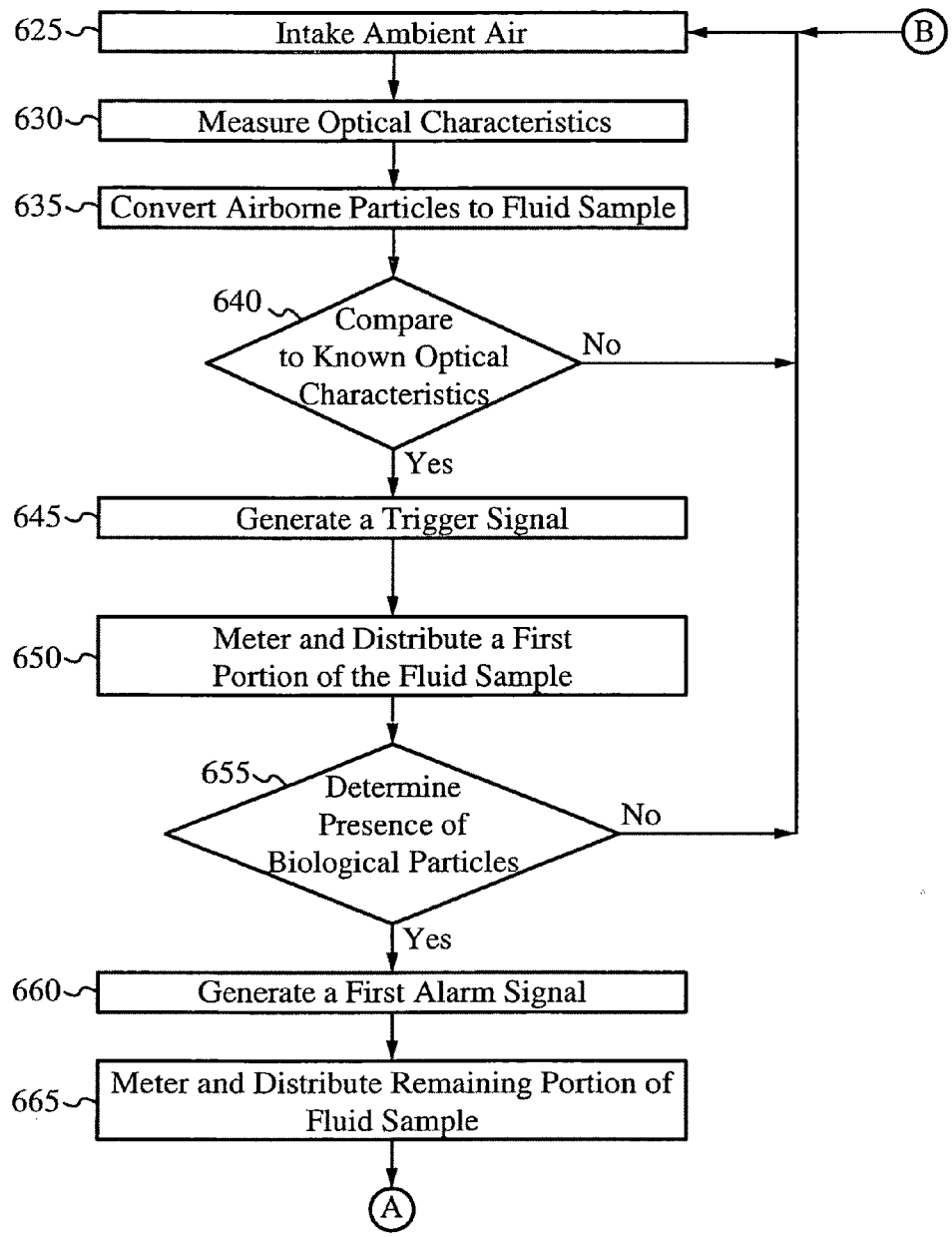
FIG. 13 illustrates an exemplary automated process performed by the third embodiment of the particle collection and detection system.

FIG. 13 illustrates an exemplary automated process performed by the third embodiment of the particle collection and detection system. At the step 625, intake ambient air into the air collection module 510. Air is continuously taken in by the air collection module 510 throughout the entire process. At the step 630, airborne particles within the ambient air are interrogated to measure one or more optical characteristics associated with the airborne particles. In some embodiments, a laser beam is used to interrogate the airborne particles such that the wavelengths of light reflected from the laser beam impinging the airborne particles is measured. At the step 635, a fluid sample is generated that includes the particles from the ambient air. At the step 640, the measured optical characteristics are compared to known optical characteristics associated with one or more different types of biological particles. If it is determined that there is not a match at the step 640, then the method returns to the step 625. If however it is determined that there is a match at the step 640, then at the step 645 a trigger signal is generated. Generation of the trigger signal indicates that at least one type of biological particle is detected within the ambient air.

In response to the trigger signal, at the step 650 a first portion of the fluid sample is metered and distributed to the confirmation device 520. At the step 655, the confirmation device 520 confirms that one or more specific types of biological particles are present in the first portion of the fluid sample. The biological particles are either specific types of toxins or specific types of pathogens. In some embodiments, the confirmation device 520 confirms the presence of one or more different types of toxins and/or pathogens using immuno assays. In some embodiments, the confirmation device 520 identifies one or more of the different types of toxins and/or pathogens. If it is determined at the step 655 that the one or more specific types of biological particles are not present in the first portion of the fluid sample, then the method returns to the step 625. If however it is determined at the step 655 that the one or more specific types of biological particles are present in the first portion of the fluid sample, then at the step 660 a first alarm signal is generated. Generation of the first alarm signal indicates that at least one type of biological particle is detected within the first portion of the fluid sample.

At the step 665, a remaining portion of the fluid sample is metered and distributed to the archive module 18, the toxin capture and detection module 22, and the lysis and capture module 20. At the step 670, second portion of the fluid sample is archived. At the step 675, toxins from within a third portion of the fluid sample are captured, purified and concentrated. At the step 680, the presence of toxins captured in the step 675 is determined and the toxins are identified. In one embodiment, optical detection is used to detect and identify the toxins.

At the step 685, cells in a fourth portion of the fluid sample are lysed. This generates a lysate solution. At the step 690, the lysate solution is metered and distributed. At the step 695, a pre-amplification process is performed on each metered portion of the first lysate. At the step 700, an amplification process is performed on each metered portion of the first lysate to generate an amplified nucleic acid solution. The pre-amplification process and the amplification process include thermal cycling. At the step 705, the presence of one or more specific types of nucleic acids in the amplified nucleic acid solution is determined and the one or more specific types of nucleic acids are identified. The steps 685 through 705 are performed in parallel with the steps 675 through 680, thereby simultaneously processing the fluid sample.

At the step 710, a second alarm signal is generated if one or more toxins are determined at the step 680 or one or more specific nucleic acids are determined at the step 705. At the step 715, the system is reset in order to process the next fluid sample to be output by the air collection module 14. The system is reset by decontaminating the microfluidic circuitry through which the fluid sample passed, any fluid sample collection vessels, the capture devices used to capture the toxins, the purification devices used to purify the nucleic acids, any purged archive chambers, and the thermal cycling chambers. Decontamination is performed using any conventional rinsing and washing steps.

Embodiments of the integrated particle collection and detection system are described above in relation to a biothreat application. It is understood that the integrated particle collection and detection system can also be used to collect non-harmful air particles and in general the integrated particle collection and detection system can be used to collect and analyze any airborne particles.

The network configuration described in relation to FIG. 1 includes the first embodiment of the collection and detection system, the collection and detection system 10. It is understood that one, some, or all of the embodiments of the collection and detection system, for example the collection and detection system 10, the detection and collection system 500, and the collection and detection system 600, can be networked in a similar manner and in any combination.

The embodiments of the collection and detection system described above are for exemplary purposes. The microfluidic circuitry and module nature of the integrated collection and detection system provides flexibility and extensibility to interconnect and configure the modules, and associated submodular components, into any desired combination. Additionally, the specific configurations described for each of the modules is for exemplary purposes. The microfluidic circuitry and constituent components of each module can be adapted into any number of configurations to perform the described functionality.

In one such adaptation, the purification device 278 used in the lysis and capture module 20 and the capture device 228 used in the toxin capture and detection module 22 are replaced by an alternative apparatus to capture and purify desired analytes, such as the toxins and nucleic acids described above. The purification device 278 and the capture device 228 are described above as including a plurality of pillars configured to capture analytes within the fluid sample passing through the device. In some applications, the concentration of the analytes within the fluid sample and/or the fluid sample flow rate through the purification device and the capture device is inadequate to capture sufficient amounts of the analytes. For example, to process a relatively large amount of fluid sample, such as processing 6 ml of fluid sample in a one hour period, the flow rate necessary to process the entire fluid sample in the allotted time period does not allow sufficient time for the analytes within the fluid sample to diffuse to the pillars within the purification device and the capture device.

An alternative capture and purification apparatus utilizes a combination of ion-exchange chromatography and size-exclusion chromatography (SEC). Ion-exchange chromatography is a process that allows the separation of analytes based on the charge properties of the analytes. This process is applied to charged analytes including, but not limited to, large proteins, small nucleotides, and amino acids. A buffered solution carries the fluid sample into a column that includes some form of stationary material. The stationary material is typically a resin or gel matrix including agarose or cellulose beads with covalently bonded charged functional groups. The target analytes adhere to the stationary material, but can be eluted by increasing the concentration of a similarly charged species that will displace the analytes from the stationary material. In some embodiments, a di-ethyl amino-ethyl (DEAE) functional group is used in the ion-exchange chromatography column, herein referred to as a DEAE column. It is understood that alternative functional groups can be used. In some embodiments, the elution buffer includes a relatively high concentration of salt. An advantage of capturing analytes using the DEAE column is that a relatively large volume of fluid sample is reduced to a smaller volume including a higher concentration of the eluted analytes.

A disadvantage of using a high concentration elution buffer is that most analytes, desired or otherwise, captured in the DEAE column are removed and present within the output eluted sample. To reduce the number of non-targeted analytes removed during the high concentration elution step, a preliminary washing step can be performed. Such a washing step is effective where the target analyte(s) has a greater charge than the non-targeted analytes, for example where the targeted analyte is DNA or RNA. The DEAE resin is positively charged. DNA is negatively charged and therefore bonds to the DEAE resin. DNA is composed of a relatively long polymer covered with negative charge. Negatively charged molecules that are smaller in size and charge than the DNA, such as proteins, also bond to the positively charged DEAE resin. However, the bond between the DNA and the DEAE resin is stronger than the bond between the DEAE resin and molecules with a smaller relative negative charge than the DNA. Different analytes elute at different concentrations of elution buffer due to this difference in bonding strength with the DEAE resin. The molecules with a smaller relative negative charge elute at smaller elution buffer concentrations than molecules with a larger relative negative charge. As such, a "washing" step is first performed using a low salt concentration elution buffer that is insufficient to elute the targeted analyte, such as DNA, but is sufficient to elute non-targeted analytes. After the washing step, a higher salt concentration elution buffer is passed through the DEAE column to elute the targeted analyte(s).

The elution buffer output from the DEAE column includes the eluted targeted analytes in a smaller fluid sample than the initial fluid sample input into the DEAE column. However, the output elution buffer includes a high salt concentration, which is not conducive to subsequent processing of the targeted analytes. Size-exclusion chromatography is used to separate the targeted analytes from the salt, or alternative elution species, in the output elution buffer. Size-exclusion chromatography (SEC) is a chromatographic method in which particles are separated based on their size. The underlying principle of SEC is that particles of different sizes will elute (filter) through a stationary material at different rates. This results in the separation of a solution of particles based on size. Provided that all the particles are loaded simultaneously or near simultaneously, particles of the same size should elute together.

SEC is typically performed using an apparatus called a column, which includes a hollow tube tightly packed with a stationary medium. In some embodiments, the stationary medium is extremely small porous polymer beads designed to have pores of different sizes. These pores can have depressions on the surface or channels through the bead. The stationary medium is pre-equilibrated with a buffer that fills the pores, depressions, and channels. As the solution (elution buffer output from the DEAE column) travels down the column, some particles enter into the pores. Larger particles cannot enter into as many pores. The larger the particles, the less overall volume to traverse over the length of the column, and the faster the elution. The particles separate by size and the larger particles elute in the pre-equilibration buffer. The filtered solution that is collected at the output of the column is known as the eluent. The eluent is separated by volumes, known as fractions. The more similar the particles are in size, the more likely they will be in the same fraction and not detected separately.

The type of stationary material is selected according to the types of the targeted analytes and the elution buffer to be separated. Examples of the stationary material include, but are not limited to, polyacrylamide, dextran, agarose, and silica.

In the exemplary application where the targeted analyte is DNA and the elution buffer output from the DEAE column includes a high salt concentration, the SEC process step is used to perform a de-salting process using a de-salting column. DNA has a relatively large size, and the salt molecules are relatively small. A SEC resin is selected as a stationary medium such that the DNA is output from the de-salting column in a separate fraction than the salt molecules. The output DNA fraction is collected in a reservoir for further processing and the salt fraction is directed to waste.

The application of separating DNA from a high salt concentration solution is an extreme case of size discrimination. In other less size discriminating applications, alternative stationary mediums can be used to provide relatively intermediate size discriminations, such as separating DNA from proteins.

Figure 14:
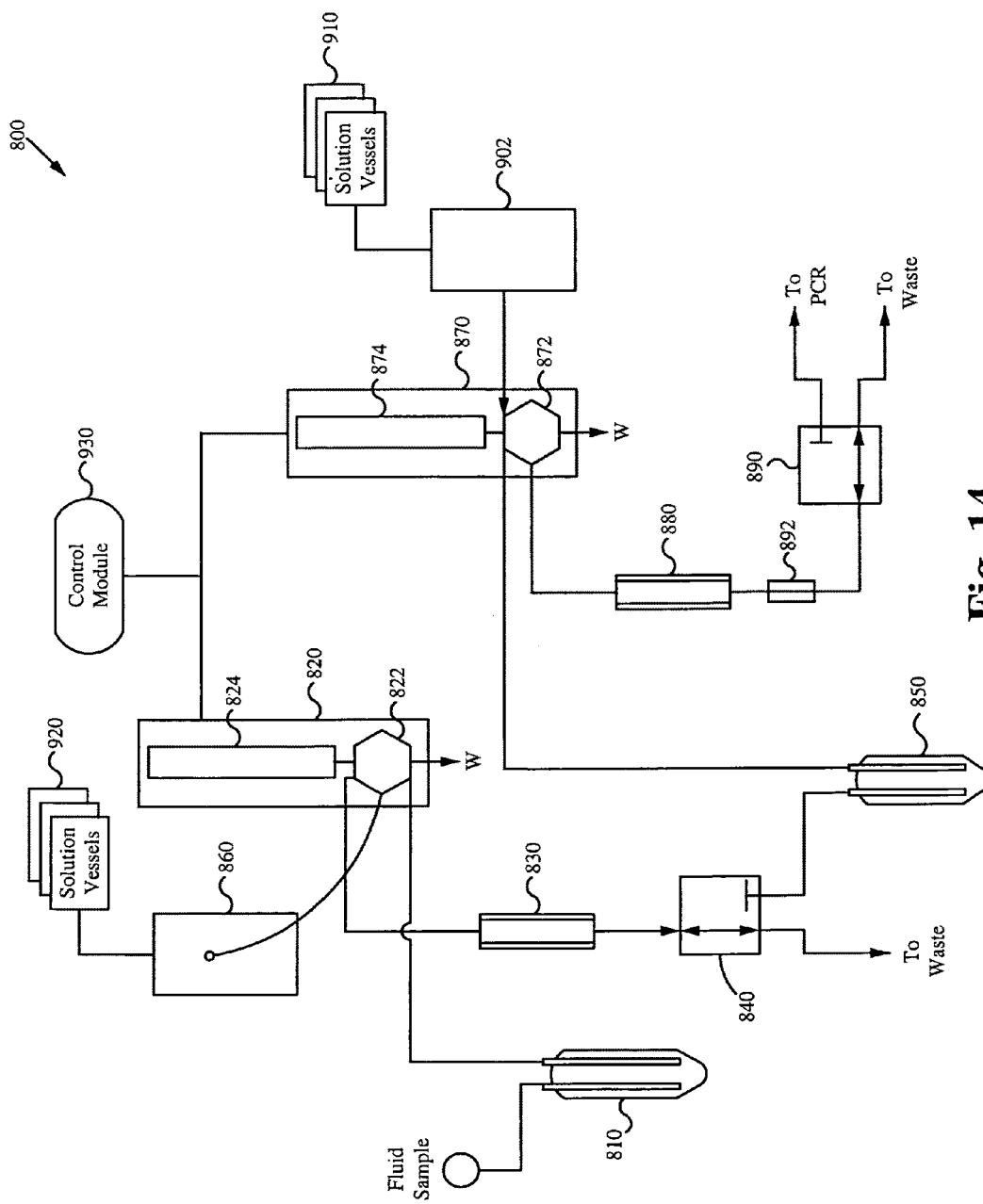
FIG. 14 illustrates an exemplary schematic block diagram of the capture and purification apparatus according to a first embodiment.

FIG. 14 illustrates an exemplary schematic block diagram of a capture and purification apparatus 800 configured to use ion-exchange chromatography and size-exclusion chromatography (SEC). The capture and purification apparatus 800 is configured to receive a fluid sample including one or more targeted analytes. In some embodiments, the capture and purification apparatus 800 is included within the lysis and capture module 20 (FIG. 6). In particular, the capture and purification apparatus 800 is configured to replace the purification device 278 within the lysis and capture module 20. In this configuration, the fluid sample received by the capture and purification apparatus 800 is the lysate output from the lysis chamber 260 (FIG. 6). In this application, the lysate includes nucleic acids which are the targeted analytes. In other embodiments, the capture and purification apparatus 800 is included within the toxin capture and detection module 22 (FIG. 5). In particular, the capture and purification apparatus 800 is configured to replace the capture device 228 within the toxin capture and detection module 22. In this configuration, the fluid sample received by the capture and purification apparatus 800 is the fluid sample output from the reservoir 226 (FIG. 5). In this application, the fluid sample includes one or more different types of toxins which are the targeted analytes. For discussion purposes, the capture and purification apparatus 800 is described below in regard to receiving the lysate including one or more targeted nucleic acids. It is understood that the capture and purification apparatus 800 can be similarly configured to capture and purify one or more targeted toxins, or any other analyte that can be captured and purified using ion-exchange chromatography and size-exclusion chromatography.

The capture and purification apparatus 800 includes a fluid reservoir 810, a fluid pump assembly 820 including a syringe pump 824 and a distribution valve 822, an ion-exchange chromatography column 830, a valve 840, a fluid reservoir 850, a distribution valve 860, a pump assembly 870 including a syringe pump 874 and a distribution valve 872, a size-exclusion chromatography column 880, a valve 890, a sensor 892, a distribution valve 902, and a plurality of solution vessels 910, 920. The syringe pumps 824, 874 are used to pump fluid throughout the capture and purification apparatus 800. The distribution valves 822, 860, 872, 902 are used to regulate flow of the fluid sample, which in this exemplary application is the lysate, and various solutions within the capture and purification apparatus 800. The solutions are stored in one or more solution vessels 910, 920, either internal and/or external to the capture and purification apparatus 800.

Fluid is directed between various components using microfluidic circuitry. For example, microfluidic circuitry is used to couple the fluid reservoir 810 to the pumping assembly 820, the distribution valve 860 to the pumping assembly 820, the pumping assembly 820 to the ion-exchange chromatography column 830, the ion-exchange chromatography column 830 to the valve 840, the valve 840 to the fluid reservoir 850, the fluid reservoir 850 to the pumping assembly 870, the distribution valve 902 to the pumping assembly 870, the pumping assembly 870 to the size-exclusion chromatography column 880, the size-exclusion chromatography column 880 to the flow sensor 892, and the flow sensor 892 to the valve 890. It is understood that additional microfluidic circuitry can be included.

Lysate is received and stored by the fluid reservoir 810. The distribution valve 822 is set to the proper channel such that the lysate is pumped from the fluid reservoir 810, through the distribution valve 822, and loaded into the ion-exchange chromatography column 830. As described above, the ion-exchange chromatography column 830 is configured to capture one or more targeted analytes, which in this exemplary application are one or more targeted nucleic acids. The valve 840 is set to direct the lysate output from the ion-exchange chromatography column 830 to waste.

After the lysate passes through the ion-exchange chromatography column 830, the distribution valve 860 and the distribution valve 822 are set to direct a wash solution through the ion-exchange chromatography column 830. In this exemplary application, the wash solution includes a low salt concentration buffer solution that elutes proteins and other non-targeted analytes from the ion-exchange chromatography column 830. In this first elution step, the low salt concentration wash solution and any eluted non-targeted analytes are directed to waste through the valve 840. The distribution valve 860 is then set to direct a buffer solution through the ion-exchange chromatography column 830. In this exemplary application, the buffer solution includes a high salt concentration buffer solution that elutes the targeted analyte (s), which are the targeted nucleic acids. In this second elution step, the high salt concentration buffer solution and any eluted targeted nucleic acids are directed to the fluid reservoir 850 via the valve 840.

The SEC column 880 is configured to separate the targeted analytes from high concentration elements and other non-targeted analytes within the fluid solution collected in the fluid reservoir 850. The SEC column 880 is first loaded with a buffer solution by setting the distribution valve 872 and the distribution valve 902 to direct the buffer solution from the buffer solution vessels 910 to the SEC column 880. Although the solution vessels 910 are shown in FIG. 14 as being separate from the solution vessels 920, it is understood that the two sets of solution vessels 910, 920, can be combined into a single set of solution vessels, or can be further distributed as three or more sets of solution vessels.

Once the SEC column 880 is loaded with the buffer solution, the fluid solution in the fluid reservoir 850 is pumped to the SEC column 880 via the distribution valve 872. The fluid solution entering the SEC column 880 is a mixture of targeted nucleic acids and the salt molecules from the high salt concentration buffer solution, as well as other trace amounts of non-targeted elements. As the fluid solution flows through the SEC column 880, elements in the fluid solution become separated into fractions, one fraction including the targeted nucleic acids and another fraction including the salt molecules. In this exemplary application, the fraction including the targeted nucleic acids outputs the SEC column 880 prior to the fraction including the salt molecules. The valve 890 is set to direct the fraction including the targeted nucleic acids output from the SEC column 880 to a next processing module, such as a PCR module, while the remaining fractions are directed by the valve 890 to waste.

A number of different techniques can be used to properly set the valve 890. A first method uses a timing technique. By experimentation, it is determined how much time is required for the targeted nucleic acids to pass through the SEC column 880, referred to as time T1, and it is determined how much time is required for the salt molecules to pass through the SEC column 880, referred to as time T2. Prior to time T1, the valve 890 is set to direct all fluid to waste. At time T1, or slightly before, the valve 890 is set to direct all fluid flow to the next processing module so that the fraction including the targeted nucleic acids is directed to the next processing module. At time T2, or slightly before, the valve is set to direct all fluid flow to waste. Configuring the capture and purification apparatus 800 within a microfluidic cartridge is particularly effective in implementing this first method. Such an implementation is described in greater detail below.

A second method uses a flow sensor 892, which senses the ionic strength in the fluid. In other words, the flow sensor 892 functions as a conductivity meter. In this manner, the sensor 892 determines fluid with high salt concentration from fluid with lower salt concentration. The sensor 892 triggers the valve 890 such that when a high salt concentration is detected, the valve 890 is set to direct fluid to waste. In some embodiments, a similar sensor is configured at the output of the ion-exchange chromatography column 830 so that when the sensor detects a high salt concentration within the fluid solution output from the ion-exchange chromatography column 830, the valve 840 is set to direct fluid to the fluid reservoir 850.

In an alternative embodiment, the capture and purification apparatus 800 of FIG. 14 is re-configured such that the fluid solution output from the valve 840 is directed to the SEC column 880, instead of to the fluid reservoir 850. Elimination of the fluid reservoir between the ion-exchange chromatography column and the SEC column results in less hardware being used, all sample from the lysate is applied to the SEC column, and there is less chance of pulling air into the SEC column.

Figure 15:
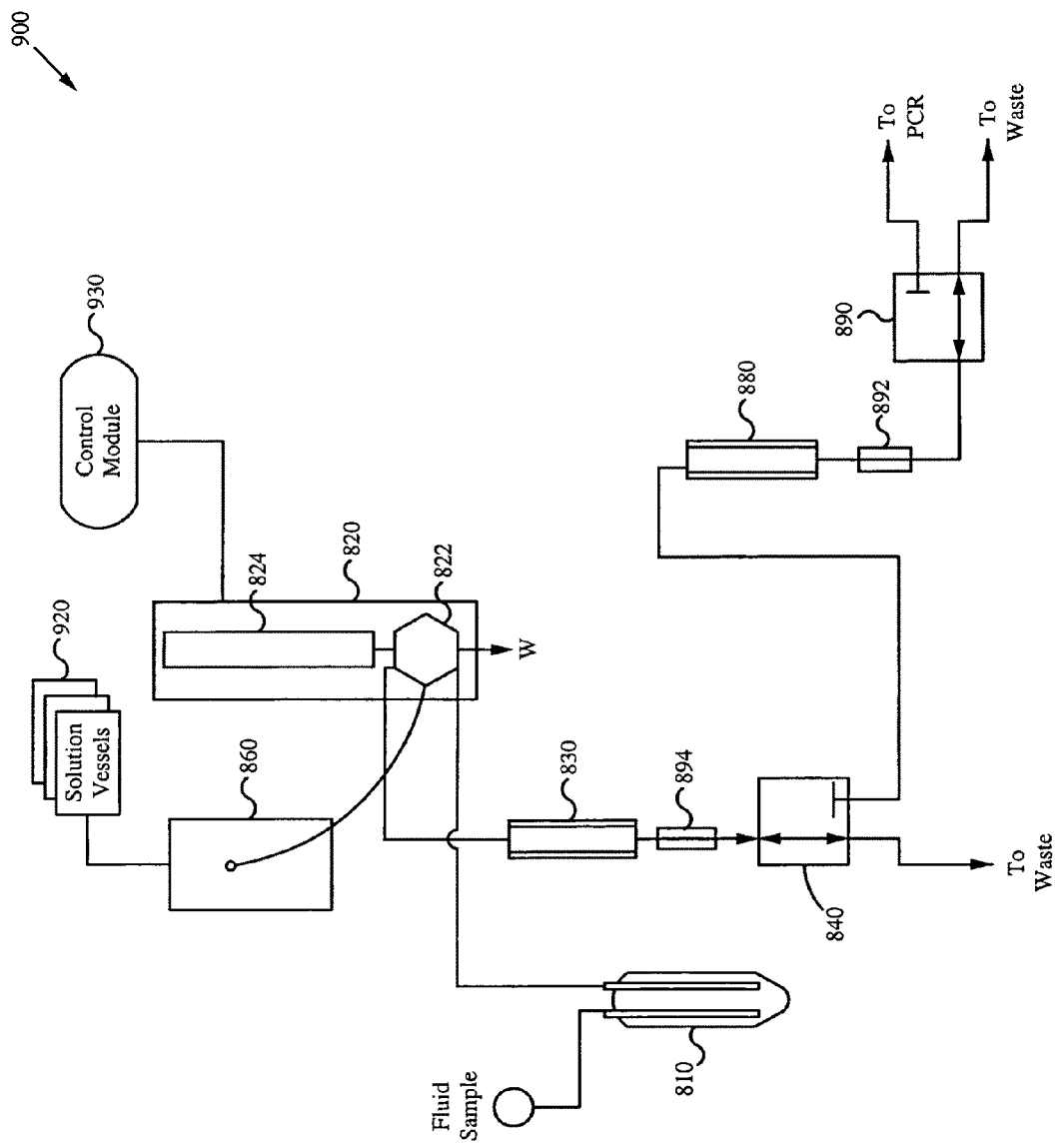
FIG. 15 illustrates an exemplary schematic block diagram of the capture and purification apparatus according to a second embodiment.

FIG. 15 illustrates an exemplary schematic block diagram of a capture and purification apparatus configured according to a second embodiment. A capture and purification apparatus 900 is configured similarly as the capture and purification apparatus 800 (FIG. 14) except that the fluid reservoir 850 (FIG. 14) is removed so that the fluid solution previously output from the valve 840 to the fluid reservoir 850 is instead provided directly to the SEC column 880 via microfluidic circuitry. Also, the capture and purification apparatus 900 includes a sensor 894. In the exemplary application where the buffer solution used to elute the targeted analytes captured in the ion-exchange chromatography column 830 is a high salt concentration buffer solution, the sensor 894 is a salt detector.

Operation of the capture and purification apparatus 900 is now described in terms of the exemplary application where the targeted analytes are nucleic acids and the wash steps are performed using various concentrations of salt buffer solutions. The valve 840 is set to direct fluid to the SEC column 880. The ion-exchange chromatography column 830 and the SEC column 880 are each equilibrated with a low salt concentration buffer solution provided via the distribution valve 822. Once the columns 830, 880 are equilibrated, the valve 840 is set to direct fluid output from the ion-exchange chromatography column 830 to waste. Lysate stored in the fluid reservoir 810 is then directed to the ion-exchange chromatography column 830.

After the lysate passes through the ion-exchange chromatography column 830, the distribution valve 860 and the distribution valve 822 are set to direct a wash solution through the ion-exchange chromatography column 830. In this exemplary application, the wash solution includes a medium salt concentration buffer solution that elutes proteins and other non-targeted analytes from the ion-exchange chromatography column 830. In this first elution step, the medium salt concentration wash solution and any eluted non-targeted analytes are directed to waste through the valve 840. The distribution valve 860 is then set to direct a buffer solution through the ion-exchange chromatography column 830 and the valve 840 is set to direct fluid output from the ion-exchange chromatography column 830 to the SEC column 880. In this exemplary application, the buffer solution includes a high salt concentration buffer solution that elutes the targeted analyte (s), which are the targeted nucleic acids. In this second elution step, the high salt concentration buffer solution and any eluted targeted nucleic acids are directed to the SEC column 880 via the valve 840. The fluid solution directed to the SEC column 880 is then separated into fractions as described above.

The sensor 894 is used as a means for setting the valve 840. In this exemplary application, the sensor 894 determines fluid with high salt concentration from fluid with lower salt concentrations. The sensor 894 triggers the valve 840 such that when a high salt concentration is detected, the valve 840 is set to direct fluid to the SEC column 880.

In an alternative configuration, a timing technique is used to set the valve 840. By experimentation, it is determined how much time is required for the high salt concentration buffer solution including the targeted nucleic acids to pass through the ion-exchange chromatography column 830, referred to as time T3. Prior to time T3, the valve 840 is set to direct all fluid to waste. At time T3, or slightly before, the valve 840 is set to direct all fluid flow to the SEC column 880.

In this alternative case, the sensor 894 is not used and can be removed. If the sensor 894 is not used, then an additional washing step can be used to reduce the possibility of contaminating the sample. In an exemplary alternative method, after performing the first elution step using a medium salt concentration buffer solution, the additional washing step is performed using a low salt concentration buffer solution. The second elution step using the high salt concentration buffer solution to elute the target analytes is then performed as described above. The additional washing step using the low salt concentration buffer reduces the possibility that the medium salt concentration buffer solution will contaminate the sample.

In another alternative configuration, the valve 840 is removed as well as the sensor 894. In this alternative case, the additional washing step is used to reduce the possibility of contaminating the sample. Since there is no valve between the ion-exchange chromatography column 830 and the SEC column 880 in this alternative configuration, the first elution step using the medium salt concentration buffer solution, the additional washing step using the low salt concentration buffer solution, and the second elution step using the high salt concentration buffer solution all flow through both the ion-exchange chromatography column 830 and the SEC column 880. This concept can be taken a step further, where the ion-exchange chromatography and the SEC are combined within a single column. In this case, the medium used for ion-exchange chromatography, such as a DEAE resin, is layered above the medium used for SEC, such as a SEC resin, to form a two-layered column where the DEAE resin layer is on top of the SEC resin layer. The first elution step using the medium salt concentration buffer solution, the additional washing step using the low salt concentration buffer solution, and the second elution step using the high salt concentration buffer solution all flow first through the DEAE resin layer and then through the second SEC resin layer within the single column.

The capture and purification apparatuses 800, 900 can also include a control module 930 to control operation of the capture and detection apparatus. Such control enables complete automation of the capture and purification apparatuses 800, 900. The control module can be integrated within the capture and purification apparatuses 800, 900, such as the control module 930, or the control module can be externally coupled to the capture and purification apparatuses 800, 900, such as the control module 12 (FIG. 2).

The capture and purification apparatus 800 shown in FIG. 14 includes two pumping assemblies 820, 870. In some embodiments, a single pumping assembly is used to regulate fluid flow within the capture and purification apparatus. The capture and purification apparatus 900 shown in FIG. 15 includes a single pumping assembly 820. In other embodiments, more than two pumping assemblies are used to regulate fluid flow within any of the previously described capture and purification apparatuses. The one or more pumping assemblies used to regulate fluid flow within the capture and purification apparatus can also be combined with one or more pumping assemblies included in the collection and detection system described above.

The capture and purification apparatus and methods are described above in terms of separating DNA from a high salt concentration solution. It is contemplated that the capture and purification apparatus and method can be configured to capture analytes other than DNA, including, but not limited to, analytes that include a net charge, positive or negative, that can be captured using ion-exchange chromatography. It is also contemplated that the capture and purification apparatus and method can be configured to elute the captured analyte using solutions other than a high salt concentration buffer solution, for example using an alcohol-based buffer solution. In general, any high concentration buffer solution can be used that elutes the targeted analyte(s) from the ion-exchange chromatography column, and where the eluted analyte(s) can be subsequently separated from the high concentration buffer solution using size-exclusion chromatography.

In some embodiments, the capture and purification apparatuses 800, 900 are configured to input a fluid sample and output a concentrated fluid sample at an input-to-output ratio of about 30:1 to about 60:1.

In another application, either of the capture and purification apparatus 800, 900 are included within a microfluidic cartridge. One such exemplary microfluidic cartridge is described in the patent application Ser. No. 10/943,601 previously referenced. The microfluidic cartridge includes microfluidic circuitry to process small liquid volumes for complex reagent metering, mixing, and biochemical analysis. In some embodiments, the microfluidic cartridge provides a closed-loop environment which minimizes environmental contamination and the potential of compromising the integrity of the sample.

Microfluidic circuitry within the microfluidic cartridge can include microfluidic fluid lines and a plurality of independently controlled valves, working systematically to direct the flow of sample and reagents. On or more syringe pumps can be used as a drive mechanism for moving, mixing, aspirating, and dispensing boluses of fluid between locations in the microfluidic cartridge. A syringe driver board controls a stepper motor that moves the syringe plungers, whereby high precision fluid metering can be accomplished. A variety of syringe sizes can be incorporated to accommodate fast, large volume movement and precise small volume metering. Peristaltic pumps can also be used as the drive mechanism. The peristaltic pump can achieve continuous flow and minimizes problems of air in the lines.

Figure 16:
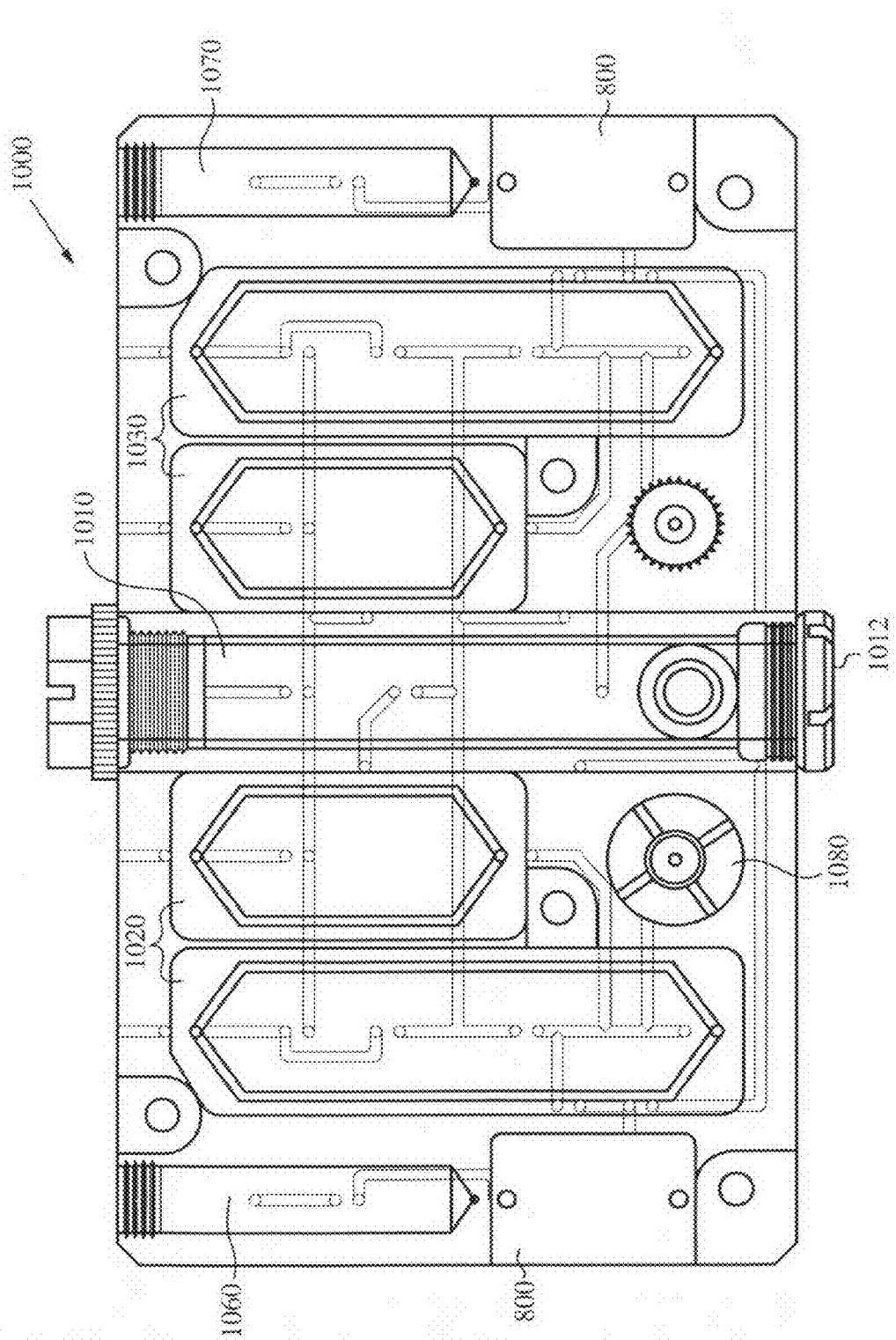
FIG. 16 illustrates an exemplary microfluidic cartridge including a first and second capture and purification apparatus.

FIG. 16 illustrates a first embodiment of an exemplary microfluidic cartridge 1000. The microfluidic cartridge 1000 includes a first and second capture and purification apparatus 800. In some embodiments, the microfluidic cartridge 1000 is configured to differentially lyse two different cell types. The microfluidic cartridge 1000 includes a sample input chamber 1010, which also functions as a sonication chamber, a first set of mixing chambers 1020, a second set of mixing chambers 1030, the first and second capture and purification apparatuses 800, a first output vessel 1060, a second output vessel 1070, and a filter 1080. The first cells are lysed using sonication within the sonication chamber 1010, while the remaining second cells remain intact. In some embodiments, a mounting seat 1012 is coupled to the outer bottom of the sonication chamber 1010. The mounting seat 1012 accepts a sonication horn and provides an interface through which sonication energy is transmitted to the sonication chamber 1010. The mounting seat 1012 is removably coupled to a sonication horn such that the sonication horn can be connected and disconnected from the integrated cartridge 1000. In this manner, the microfluidic cartridge 1000 can be coupled to any number of different sonication horns, or any number of microfluidic cartridges 1000 can be sequentially coupled to a single sonication horn.

Solution including the lysed first cells and the intact second cells is directed to the filter 1080 which passes the first cell lysate and blocks the intact second cells. The first cell lysate is directed to the first set of mixing chambers 1020. The first set of mixing chambers 1020 is used to mix the first cell lysate with any desired solution, such as a bind solution, in preparation for DNA concentration and purification within the first capture and purification apparatus 800. In some embodiments, the first set of mixing chambers 1020 includes two independent chambers connected to each other. It is understood that more, or less, than two chambers can be used. The mixed solution from the first set of mixing chambers 1020 is directed through the first capture and purification apparatus 800 where the first cell DNA is purified and concentrated while the remaining portion of the mixed solution passes through as waste. The first cell DNA is then eluted into the first output vessel 1060.

The intact second cells are back flushed from the filter 1080 to the second set of mixing chambers 1030. The second set of mixing chambers 1030 is used to mix the intact second cells with any desired solution. In some embodiments, the second set of mixing chambers 1030 includes two independent chambers connected to each other. It is understood that more, or less, than two chambers can be used. Within the second set of mixing chambers, the intact second cells are lysed. Lying the second cells can be performed using chemicals, heat, or a combination thereof. In some embodiments, the microfluidic cartridge 1000 is fitted to a heating plate (not shown) such that heat can be applied to all, or a portion of, the second set of mixing chambers 1030.

In an alternative embodiment, the intact second cells are back flushed from the filter 1080 to the sonication chamber 1010. In the sonication chamber 1010, the intact second cells are lysed using sonication. Chemicals and/or other additives, such as glass beads, can be added to the sonication chamber 1010 prior to application of the sonication energy. In this manner, the second cells can be lysed using sonication, or a combination of sonication and other additives.

Second cell lysate is then directed from either the sonication chamber 1010 or the second set of mixing chambers 1030 to the second capture and purification apparatus 800. If the protocol demands, the second cell lysate can be mixed with a desired solution within the second set of mixing chambers 1030 prior to passing through the second capture and purification apparatus 800. Second cell DNA is purified and concentrated within the second capture and purification apparatus 800, while the remaining portion of the second cell lysate solution passes through as waste. The second cell DNA is then eluted into the second output vessel 1070.

In some embodiments, the microfluidic cartridge 1000 is coupled to a mounting plate (not shown). The mounting plate couples to the microfluidic cartridge 1000 at select injection ports to provide mixing reagents and transmission fluid for the microfluidic circuitry.

In an alternative embodiment, a microfluidic cartridge includes a sonication chamber, one set of mixing chambers, one capture and purification apparatus, and one output vessel. In this alternative embodiment, the microfluidic cartridge is used to perform a single lysis step. Protocols can use any combination of sonication, chemical, and heat steps as described above.

In some embodiments, the microfluidic cartridge includes the solution vessels 910, 920 (FIGS. 14 and 15). In other embodiments, the solution vessels 910, 920 are not included in the microfluidic cartridge. Instead, the microfluidic cartridge is coupled to externally located solution vessels.

Figure 17:
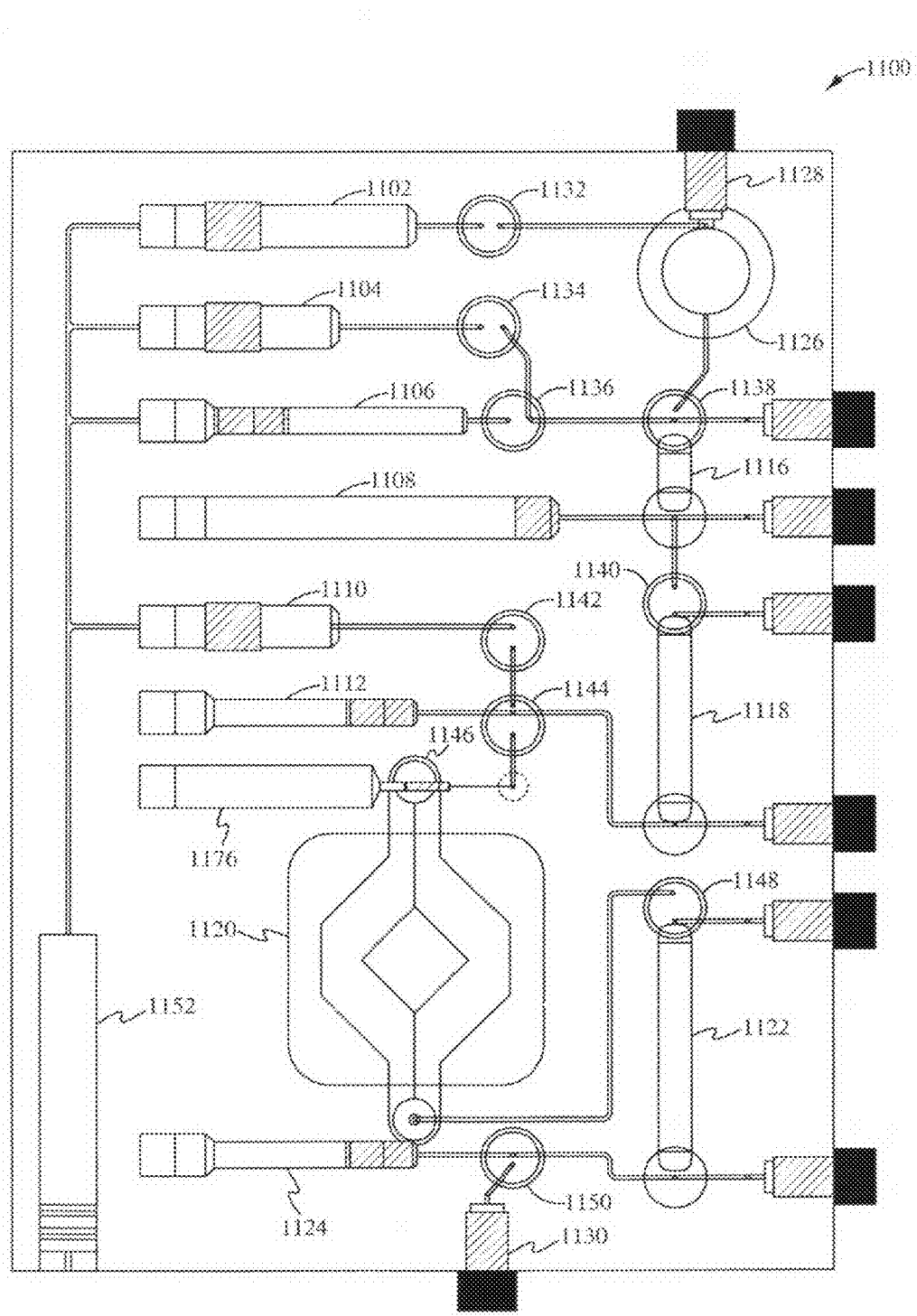
FIG. 17 illustrates a second embodiment of an exemplary microfluidic cartridge.

FIG. 17 illustrates a second embodiment of an exemplary microfluidic cartridge 1100. The microfluidic cartridge 1100 includes a first reagent syringe 1102, a second reagent syringe 1104, a third reagent syringe 1106, a fourth reagent syringe 1110, a first waste syringe 1108, a second waste syringe 1112, a third waste syringe 1124, an input chamber 1126, an ion-exchange chromatography (IEC) column 1116, a first SEC column 1118, a second SEC column 1122, a thermal cycling chamber 1120, a driving syringe 1152, a sample input port 1128, a thermal cycling reagent input port 1176, an output port 1130, and valves 1132-1150. The components within the microfluidic cartridge 1100 are coupled via microfluidic circuitry, as described below.

FIGS. 18-27 illustrate exemplary block diagrams of the microfluidic cartridge 1100 in various stages of operation. In some embodiments, the cartridge 1100 is coupled to an external actuation instrument that includes a sonication horn 1168 coupled to the lysing chamber 1126, a thermo-electric cooler (TEC) 1170 coupled to the thermal cycling chamber 1120, a drive motor 1174 coupled to the driving syringe 1152, and a plurality of valve actuation mechanisms, one valve actuation mechanism coupled to each of the valves 1132-1150. FIG. 28 illustrates the cartridge 1100 coupled to an exemplary actuation instrument 1200. The cartridge 1100 slides in and out of a frame 1220. The actuation instrument 1200 includes the TEC 1170, the sonication horn 1168, and the drive motor 1174. The actuation instrument 1200 also includes a user interface 1210 coupled to a control module (FIG. 18), a plurality of valve actuation mechanisms 1230, and an optional second TEC 1240.

A valve actuation mechanism is a solenoid or alternative mechanical means for switching the valve from a closed position to an open position. In some embodiments, the valve actuation mechanism is configured to be actuated in response to an electrical control signal. In some embodiments, each valve and valve actuation mechanism are configured to actuate once, as a single use application, from an initial closed position to a final open position. Once a valve is opened, the valve remains open. In this configuration, the valve and the valve actuation mechanism are not configured to actuate additional times, and the valve is not configured to be actuated from the open position back to the closed position. A description of one such exemplary valve and valve actuation mechanism is provided in the U.S. patent application Ser. No. 12/290,345, filed on Oct. 8, 2008, and entitled "A Microfluidic Valve Mechanism", which is hereby incorporated in its entirety by reference.

A control module 1180 is coupled to the sonication horn 1168, the TEC 1170, the drive motor 1174, and the plurality of solenoids coupled to each of the valves 1132-1150 to send control signals that actuate the respective device. Each of the sonication horn 1168, the TEC 1170, the drive motor 1174, and the plurality of solenoids can be independently controlled in this manner. In some embodiments, the control module 1180 executes instructions provided in a control algorithm such that the sample preparation process is completely automated. The control module can be integrated within the cartridge 1100, as part of the external actuation instrument, or as a separate component.

Figure 18:
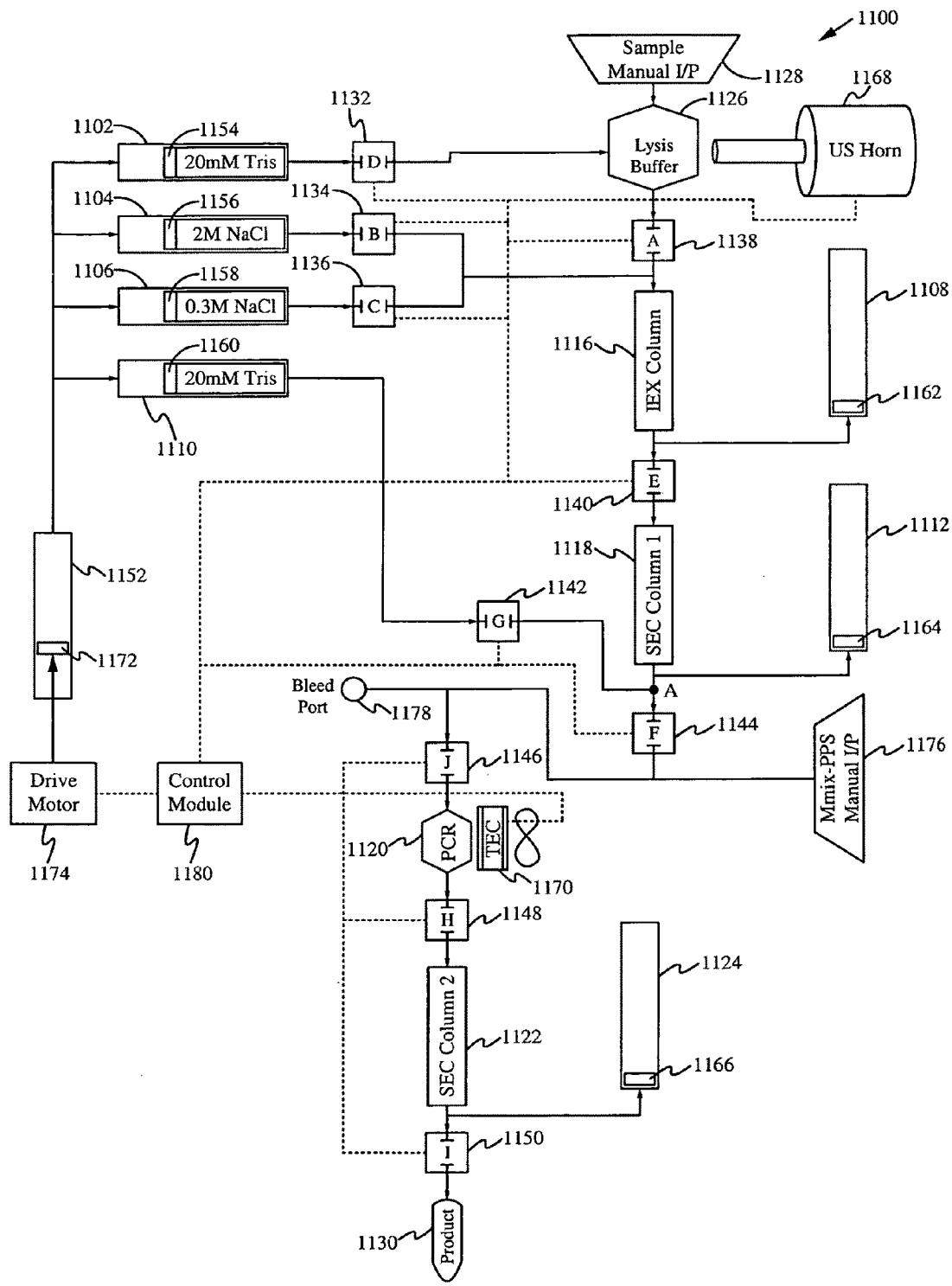
FIGS. 18-27 illustrate exemplary block diagrams of the microfluidic cartridge of FIG. 17 in various stages of operation.

FIG. 18 illustrates the cartridge 1100 in a pre-loaded state where the cartridge is pre-loaded with fluid. All valves 1132-1150 are initially configured in a closed position. Each component within the cartridge 1100, including the microfluidic lines, is loaded with fluid, except for the lysing chamber 1126, the first waste syringe 1108, the second waste syringe 1112, the third waste syringe 1124, and the thermal cycling chamber 1120. The lysing chamber 1126 is left empty or partially filled with fluid to allow for input of a fluid sample to be analyzed. The first reagent syringe 1102 is filled with a first amount of a first reagent, in this exemplary application a 20 mM Tris. The second reagent syringe 1104 is filled with a second amount of a second reagent, in this exemplary application a 2M NaCl high salt concentration buffer solution. The third reagent syringe 1106 is filled with a third amount of a third reagent, in this exemplary application a 0.3M NaCl low salt concentration buffer solution. The fourth reagent syringe 1110 is filled with a fourth amount of a fourth reagent, in this exemplary application a 20 mM Tris. The first reagent syringe 1102, the second reagent syringe 1104, the third reagent syringe 1106, and the fourth reagent syringe 1110 are each fluidically coupled to a common fluid driver, the driving syringe 1152. As such, actuation of the driving syringe 1152 applies fluid pressure to each of the reagent syringes 1102, 1104, 1106, 1110.

A plunger 1154, a plunger 1156, a plunger 1158, and a plunger 1160 are positioned within the first reagent syringe 1102, the second reagent syringe 1104, the third reagent syringe 1106, and the fourth reagent syringe 1110, respectively, such that each reagent syringe is divided into an input portion and an output portion by the plunger. As applied to the exemplary configuration in FIG. 18, the input portion of each reagent syringe is on the driving syringe side (left hand side in FIG. 18) of the plunger, and the output portion of the reagent syringe is on the opposite side (right hand side in FIG. 18) of the plunger. The plunger 1154 is positioned within the first reagent syringe 1102 such that the output portion of the first reagent syringe 1102 has a volume that is equal to the first amount of the first reagent. The plunger 1156 is positioned within the second reagent syringe 1104 such that the output portion of the second reagent syringe 1104 is equal to the second amount of the second reagent. The plunger 1156 is positioned within the third reagent syringe 1106 such that the output portion of the third reagent syringe 1106 has a volume that is equal to the third amount of the third reagent. The plunger 1160 is positioned within the fourth reagent syringe 1110 such that the output portion of the fourth reagent syringe 1108 has a volume that is equal to the fourth amount of the fourth reagent.

A plunger 1172 is positioned within the driving syringe 1152 such that the driving syringe 1152 is divided into an input portion and an output portion by the plunger 1172. As applied to the exemplary configuration in FIG. 18, the output portion of the driving syringe 1152 is the top portion above plunger 1172. The plunger 1172 is positioned within the driving syringe 1152 such that a volume of the output portion of the driving syringe 1152 has a volume that is equal to the sum of the first amount of the first reagent, the second amount of the second reagent, the third amount of the third reagent, and the fourth amount of the fourth reagent. The output portion of the driving syringe 1152, the input portions of the reagent syringes 1102, 1104, 1106, 1110, and the microfluidic lines that connects the driving syringe 1152 and the reagent syringes 1102, 1104, 1106, 1110 are pre-loaded with a fluid solution.

A plunger 1162, a plunger 1164, and a plunger 1166 are positioned at a fluid input side within the first waste syringe 1108, the second waste syringe 1112, and the third waste syringe 1124, respectively. As applied to the exemplary configuration in FIG. 18, the input side of each waste syringe is on the bottom surface. The space within each waste syringe 1108, 1112, 1124 above the plunger is filled with air. The top of each waste syringe 1108, 1112, 1124 has an air vent to output air as the plunger is pushed into the waste syringe. The volume within each waste syringe 1108, 1112, 1124, less the volume of the plunger, is determined by the first amount of the first reagent, the second amount of the second reagent, the third amount of the third reagent, and the fourth amount of the fourth reagent, as will be described in greater detail below.

The IEC column 1116, the SEC column 1118, and the SEC column 1122 are each equilibrated with a buffer solution. In some embodiments, the buffer solution is a low salt concentration buffer solution.

The remaining microfluidic lines are also loaded with a buffer solution. Specifically, the microfluidic lines between the first reagent syringe 1102 and the valve 1132, the valve 132 and the lysing chamber 1126, the lysing chamber 1126 and the valve 1138, the valve 1138 and the IEC column 1116, the second reagent syringe 1104 and the valve 1134, the valve 1134 and the IEC column 1116, the third reagent syringe 1106 and the valve 1136, the valve 1136 and the IEC column 1116, the IEC column 1136 and the first waste syringe 1108, the IEC column 1116 and the valve 1140, the valve 1140 and the SEC column 1118, the SEC column 1118 and the second waste syringe 1112, the SEC column 1118 and the valve 1144, the fourth reagent syringe 1110 and the valve 1142, the valve 1142 and the valve 1144, the valve 144 and the valve 146, the thermal cycling reagent input port 1176 and the bleed port 1178, the valve 146 and the thermal cycling chamber 1120, the thermal cycling chamber 1120 and the valve 1148, the valve 1148 and the SEC column 1122, the SEC column 1122 and the third waste syringe 1124, the SEC column 112 and the valve 1150, and the valve 1150 and the output port 1130.

The driving syringe plunger 1172 is coupled to a drive motor 1174, such as a stepper motor, that pushes the plunger 1172. In the exemplary configuration of FIG. 18, the plunger 1172 is pushed upward. In general, the number of steps actuated by the drive motor 1174 determines the fluid volume that is displaced. A speed by which the steps are actuated is also specified to the drive motor 1174, which corresponds to the flow-rate. The speed is determined by the specific requirements of the assay.

Figure 19:
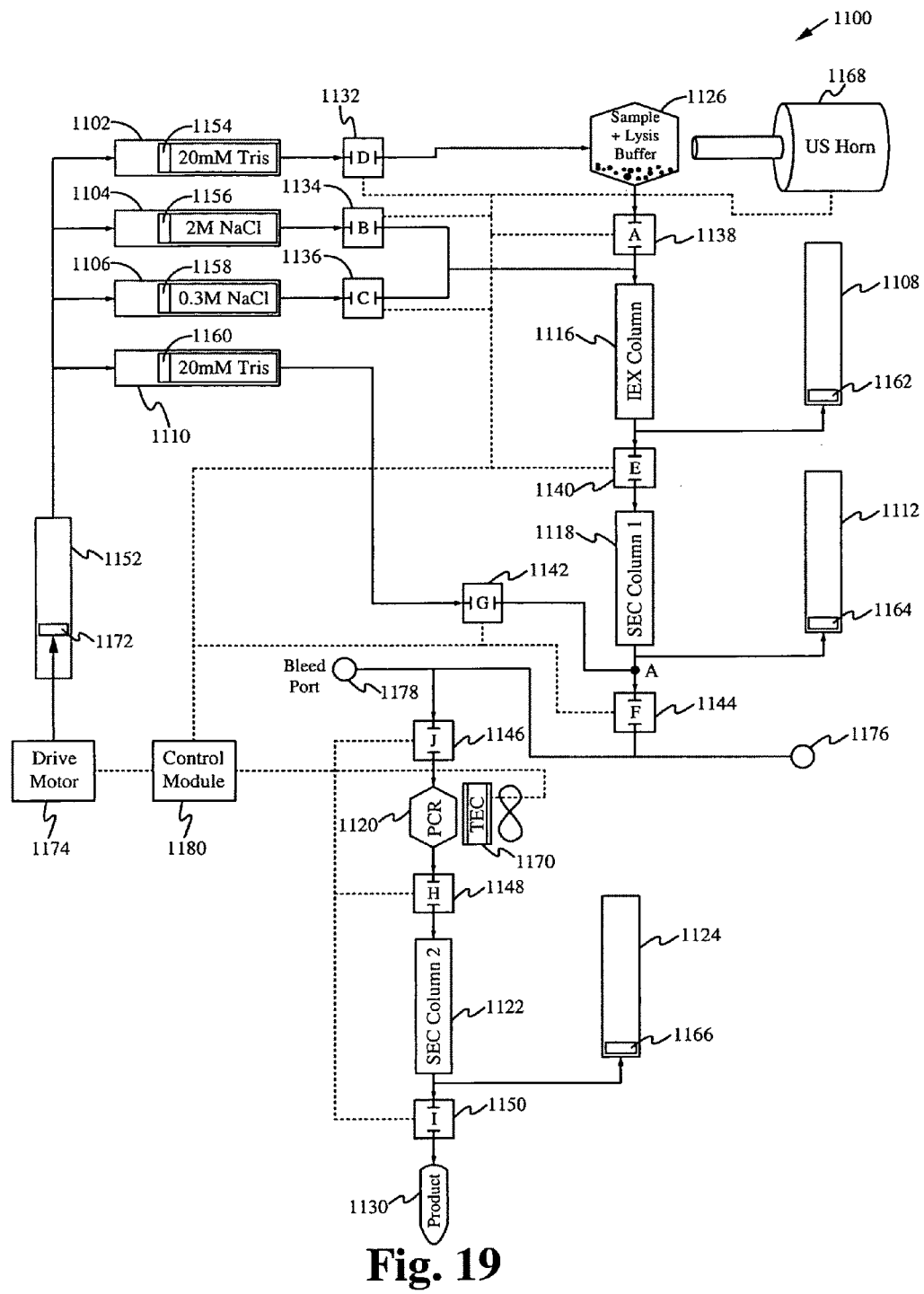

FIG. 19 illustrates the cartridge 1100 in a fully loaded state where a fluid sample and thermal cycling reagents have been added. The fluid sample is input to the lysing chamber 1126 via the fluid sample input port 1128. The lysing chamber 1126 is completely filled with fluid. If the volume of the input fluid sample is insufficient to completely fill the lysing chamber 1126, additional buffer solution is added via the input port 1128. Once the lysing chamber 1126 is filled, the input port 1128 is sealed, such as using a plug. In some embodiments, the buffer and/or fluid sample is directly injected into the lysing chamber 1126 via a needle piercing a septum, such as a self-sealing elastomeric plug.

With the bleed port 1178 open, the thermal cycling reagents are input via the input port 1176. The buffer solution previously loaded into the microfluidic lines between the input port 1176 and the bleed port 1178 is displaced by the input thermal cycling reagents, and output via the bleed port 1178. Once the thermal cycling reagents are added, the input port 1176 and the bleed port 1178 are sealed, such as by using plugs. Once the ports are sealed, the microfluidic line between the input port 1176 and the bleed port 1178 is loaded with thermal cycling reagents.

After sealing the ports 1128, 1176, 1178, lysis is performed on the fluid sample within the lysing chamber 1126, thereby forming a lysate. In some embodiments, lysis is performed by sonication using a sonication horn 1168 is coupled to the lysing chamber 1126. In this exemplary configuration, the sonication horn 1168 is part of an external actuation instrument to which the cartridge 1100 is coupled. Alternatively, the sonication horn is included as part of the cartridge. In other embodiments, lysis is performed using other conventional lysing methods. For example, the lysis buffer loaded into the lysing chamber 1126 can include chemicals specifically used for lysing and a heater can be coupled to the lysing chamber. The heater can be part of the external actuation instrument or can be included as part of the cartridge.

Figure 20:
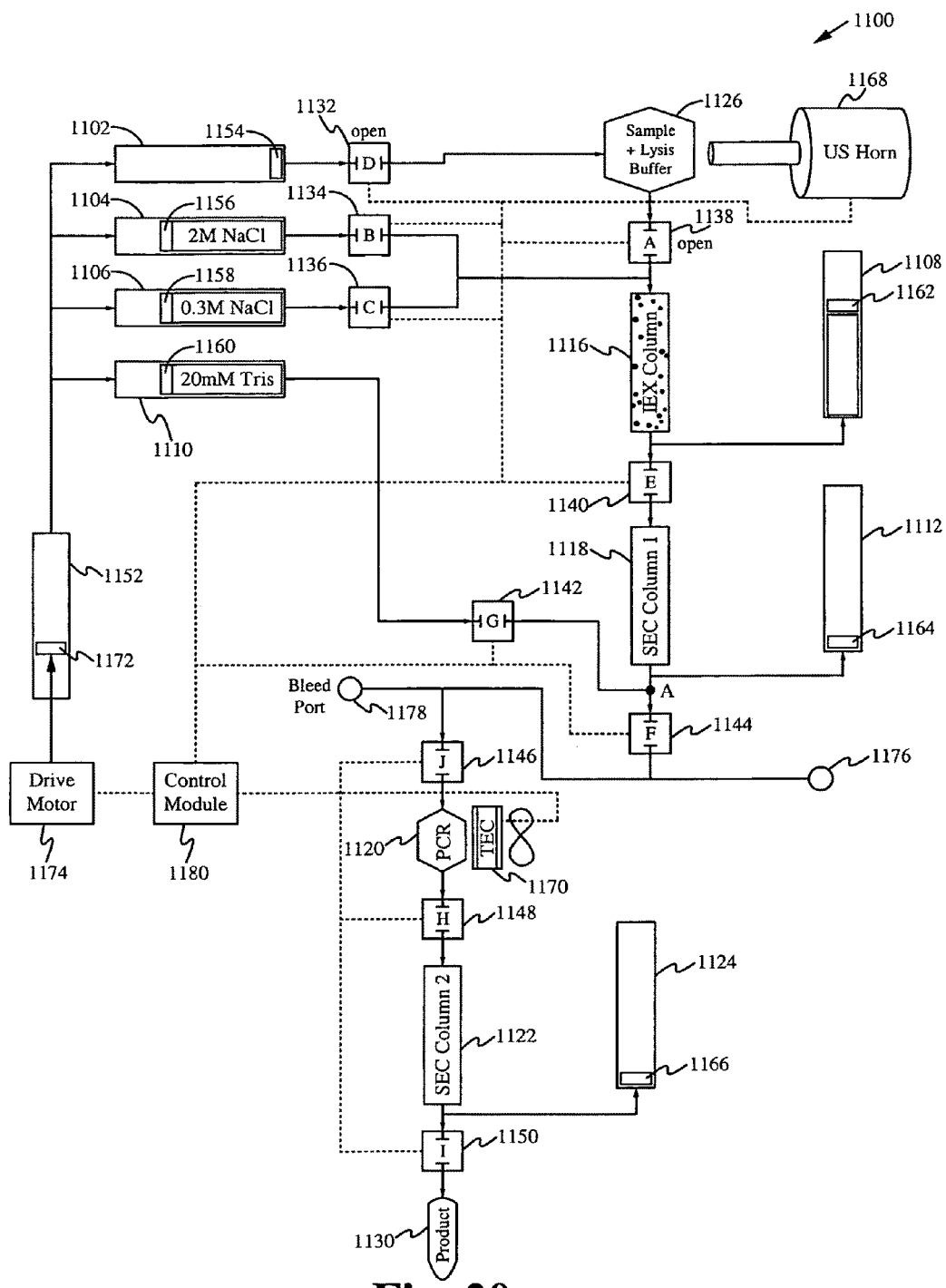

To move the lysate through the IEC column 116, the valves 1132 and 1138 are opened, and the drive motor 1174 is actuated. Actuation of the drive motor 1174 pushes the plunger 1172 up within the driving syringe 1152, thereby forcing fluid against each of the plungers 1154, 1156, 1158, 1160. Since the valves 1134, 1136, 1142 remain closed, the plungers 1156, 1158, 1160 can not be pushed forward, and only the plunger 1154 is pushed forward, as shown in FIG. 20. As the plunger 1154 is pushed forward, the first reagent within the output portion of the first reagent syringe 1102 is forced out of the reagent syringe 1102, forcing fluid through the open valve 1132, and into the lysing chamber 1126. The in-flow of fluid into the lysing chamber 1126 forces the lysate out of the lysing chamber 1126, through the valve 1138 and through the IEC column 1116. As the lysate is flows through the IEC column 116, the equilibrated buffer solution is displaced out of the IEC column 116 and into the first waste syringe 1108, forcing the plunger 1162 upward. The first amount of first reagent in the first reagent syringe 1102 is sufficient to force the entire volume within the lysing chamber, the lysate, through the IEC column 1116. Target analytes present in the lysate are captured within the IEC column 1116.

The plunger 1154 moves from an initial position, as shown in FIG. 18, to an end position, as shown in FIG. 20. The end position is dictated by a stop (not shown) within the first reagent syringe 1102. The plunger 1154 can not be pushed beyond the stop. Once the plunger 1154 reaches the end position, no additional fluid is forced out of the lysing chamber 1126 and through the valve 1138.

The volume specifications within the cartridge 1100 are tightly regulated so as to achieve precise fluid movement from one component to the next. The volume specifications translate to specific actuation specifications of the drive motor 1174 and fluid force applied by the driver syringe 1152. As applied to the plunger 1154, the movement of the plunger 1154 from the initial position to the end position corresponds to a specific amount of movement of the plunger 1172 in the driving syringe 1152, as driven by the drive motor 1174. In the case where the drive motor 1174 is a stepper motor, the movement of the plunger 1154 from the initial position to the end position corresponds to a specific number of steps of the stepper motor.

In some embodiments, once the specific number of steps is reached, a control signal is sent to open the valve 1136. In other embodiments, a sensor (not shown) is positioned at the end position within each of the reagent syringes. The sensor detects when the plunger 1154 reaches the end position, at which point a control signal is sent to open the valve 1136.

To wash the IEC column 116 and to remove non-specific products, the valve 1136 is opened, and the drive motor 1174 is again actuated. Actuation of the drive motor 1174 pushes the plunger 1172 up within the driving syringe 1152, thereby forcing fluid against each of the plungers 1154, 1156, 1158, 1160. Since the valves 1134 and 1142 remain closed, the plungers 1156 and 1160 can not be pushed forward, and although the valve 1132 remains open, the stop in the reagent syringe 1102 prevents the plunger 1154 from being forced forward. Only the plunger 1158 is pushed forward, as shown in FIG. 21.

As the plunger 1158 is pushed forward, the third reagent within the output portion of the third reagent syringe 1106 is forced out of the reagent syringe 1106, forcing fluid through the open valve 1136, and through the IEC column 1116. The third reagent flows into the IEC column 1116 and not back toward the lysing chamber 1126. If the third reagent were to flow toward the lysing chamber 1126, fluid would be forced against the plunger 1154, generating a force toward the initial plunger position. However, this force is negated by the force generated in the opposite direction by the movement of the plunger 1172 in the driving syringe 1152.

As the third reagent flows through the IEC column 1116, the remaining first reagent is displaced out of the IEC column 116 and into the first waste syringe 1108, further forcing the plunger 1162 upward. The third amount of third reagent in the third reagent syringe 1106 is sufficient to force out the entire amount of first reagent remaining in the IEC column 1116. The third reagent is configured to not remove target analytes captured within the IEC column 1116. In some embodiments, the third reagent is a low salt concentration buffer solution, such as 0.3M NaCl buffer solution.

Figure 21:
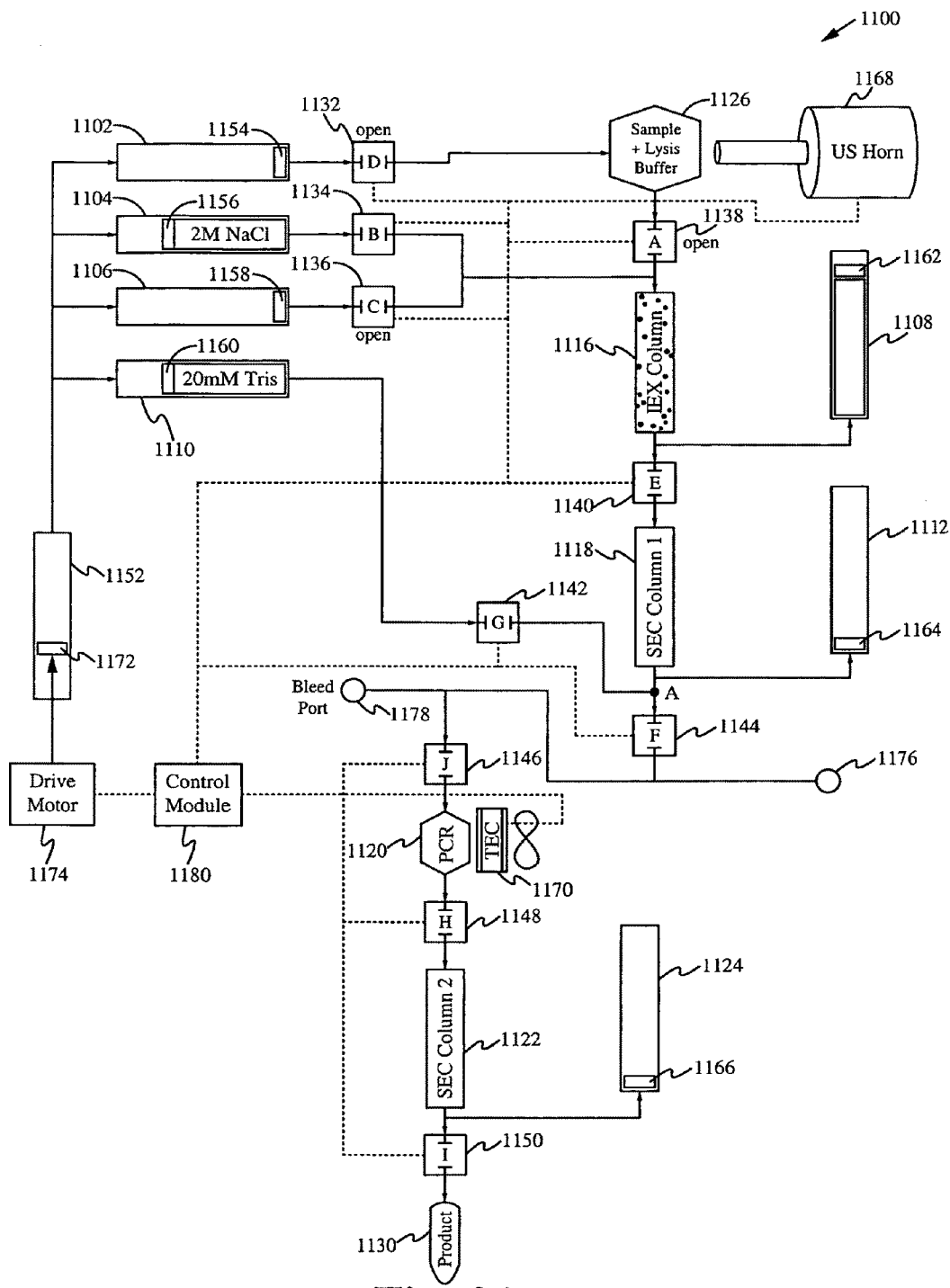

The plunger 1158 moves from an initial position, as shown in FIG. 18, to an end position, as shown in FIG. 21. The end position is dictated by a stop (not shown) within the third reagent syringe 1106. Similarly to the plunger 1154, the movement of the plunger 1158 from the initial position to the end position corresponds to a specific amount of movement of the plunger 1172 in the driving syringe 1152, as driven by the drive motor 1174. In the case where the drive motor 1174 is a stepper motor, the movement of the plunger 1158 from the initial position to the end position corresponds to a specific number of steps of the stepper motor.

In some embodiments, once the specific number of steps corresponding to the movement of the plunger 1158 is reached, a control signal is sent to open the valve 1134. In other embodiments, a sensor (not shown) detects when the plunger 1158 reaches the end position, at which point a control signal is sent to open the valve 1134.

Figure 22:
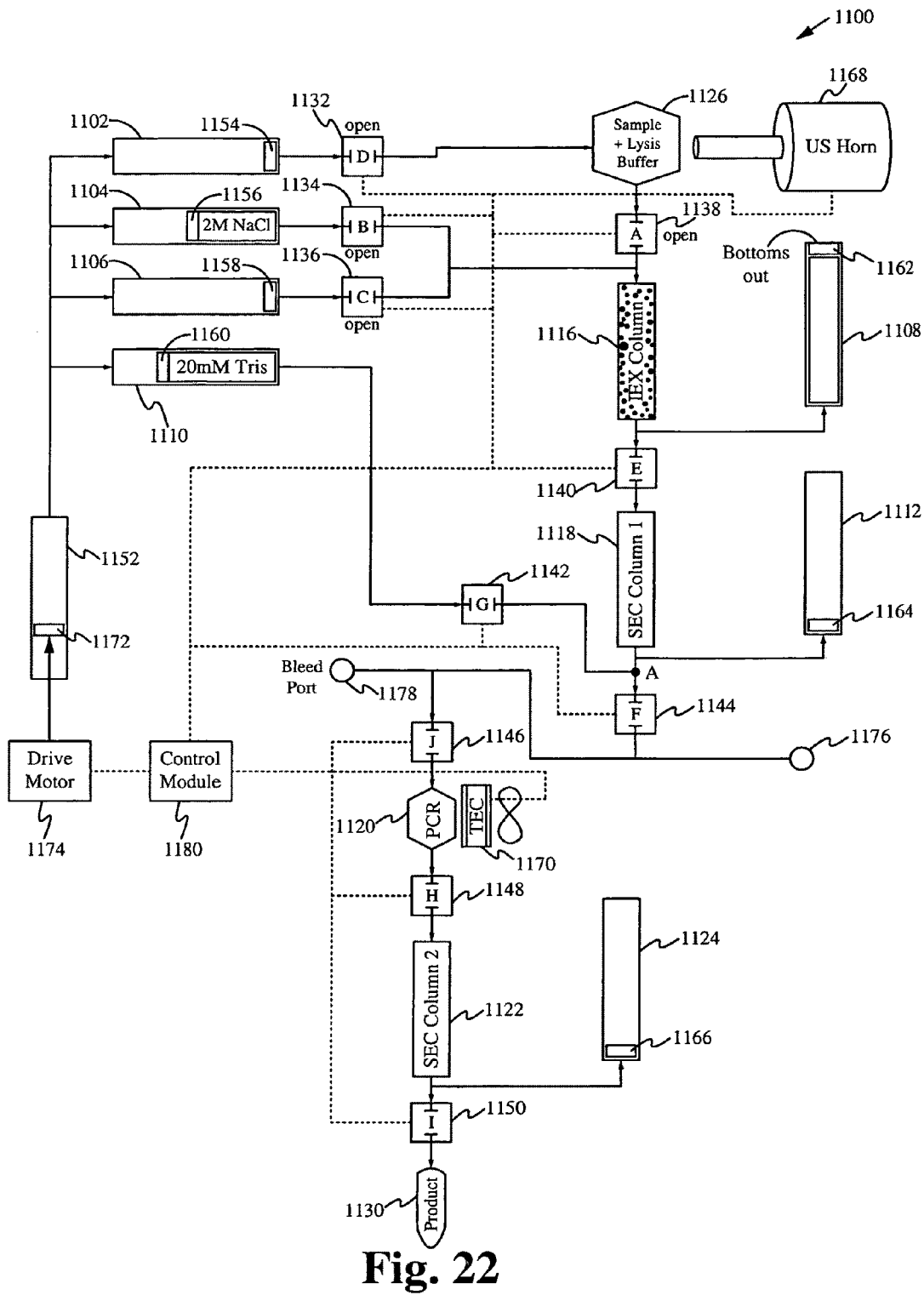

To remove the target analytes captured within the IEC column 1116, the valve 1134 is opened, the drive motor 1174 is again actuated, and a first portion of the second reagent is forced through the IEC column 1116. In some embodiments, the second reagent is a high salt concentration buffer solution, such as a 2M NaCl buffer solution. Actuation of the drive motor 1174 pushes the plunger 1172 up within the driving syringe 1152, thereby forcing fluid against each of the plungers 1154, 1156, 1158, 1160. Since the valve 1142 remains closed, the plunger 1160 can not be pushed forward, and although the valves 1132 and 1136 remain open, the stops in the reagent syringes 1102, 1106 prevent the plungers 1154, 1158 from being forced forward. Only the plunger 1156 is pushed forward, as shown in FIG. 22. During this step, only a first portion of the second reagent is forced out of the reagent syringe 1104.

As the plunger 1156 is pushed forward from the initial position to a first position, as shown in FIG. 22, the first portion of the second reagent is forced out of the reagent syringe 1104, forcing fluid through the open valve 1134, and through the IEC column 1116. The second reagent flows into the IEC column 1116 and not back toward the lysing chamber 1126 or though the valve 1136 due to the drive motor actuating force exerted on the plungers 1154 and 1158.

As the first portion of the second reagent flows through the IEC column 1116, the remaining third reagent is displaced out of the IEC column 116 and into the first waste syringe 1108, forcing the plunger 1162 upward to an end position. The end position corresponds to a stop at the top of the first waste syringe 1108. The first portion of the second reagent is sufficient to force out the entire amount of third reagent remaining in the IEC column 1116 and to fully load the IEC column 1116 with second reagent. None of the second reagent flows into the first waste syringe 1108. The first portion of the second reagent is also sufficient to force enough fluid into the first waste syringe 1108 such that the first waste syringe 1108 is fully loaded and the plunger 1162 is forced against the top, or stop. With the plunger 1162 forced against the stop, no additional fluid can be forced into the first waste syringe 1108. The volume of the first waste syringe 1108 is precisely configured so that the plunger 1162 is forced against the stop before any of the second reagent enters the first waste syringe 1108.

The plunger 1162 moves from an initial position, as shown in FIG. 18, to the end position, as shown in FIG. 22. Similarly to the plungers 1154 and 1158, the movement of the plunger 1162 from the initial position to the end position corresponds to a specific amount of movement of the plunger 1172 in the driving syringe 1152, as driven by the drive motor 1174. In the case where the drive motor 1174 is a stepper motor, the movement of the plunger 1162 from the initial position to the end position corresponds to a specific number of steps of the stepper motor.

In some embodiments, once the specific number of steps corresponding to the movement of the plunger 1162 is reached, a control signal is sent to open the valve 1140. In other embodiments, a sensor (not shown) detects when the plunger 1162 reaches the end position, at which point a control signal is sent to open the valve 1140.

The second reagent, for example the high salt concentration buffer solution, is configured to elute the target analytes captured within the IEC column 1116. To direct this eluted solution to the SEC column 1118, the valve 1140 is opened and the drive motor 1174 is actuated such that a second portion of the second reagent is displaced from the second reagent syringe 1104, as shown in FIG. 23.

Figure 23:
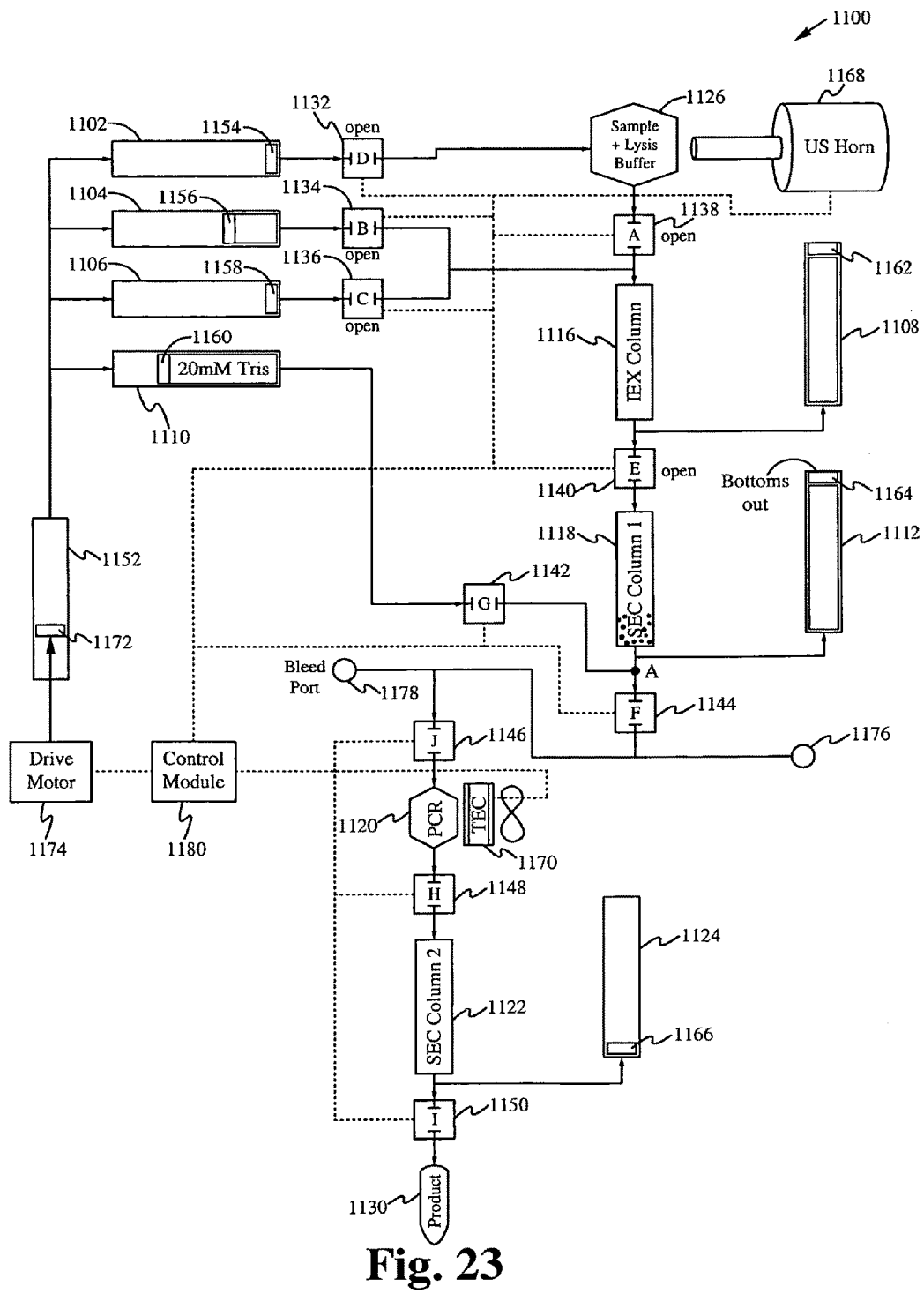

As the plunger 1156 is pushed forward from the first position to a second position, as shown in FIG. 23, the second portion of the second reagent is forced out of the reagent syringe 1104, through the open valve 1134, and through the IEC column 1116. The second reagent flows into the IEC column 1116 and not back toward the lysing chamber 1126 or though the valve 1136 due to the drive motor actuating force exerted on the plungers 1154 and 1158.

As the second portion of the second reagent flows through the IEC column 1116, the first portion of the second reagent already loaded in the IEC column 1116 is displaced out of the IEC column 1116, through the valve 1140 and into the SEC column 1118. The second reagent that flows into the SEC column 118 includes the eluted target analytes from the IEC column 1116. The equilibrated fluid solution initially loaded into the SEC column 118 is displaced out of the SEC column 118 by the in-flow of the second reagent and into the second waste syringe 1112, forcing the plunger 1164 upward to an end position. The end position corresponds to a stop at the top of the second waste syringe 1112. The second portion of the second reagent is sufficient to input the eluted target analytes into a top portion of the SEC column 118, while a bottom portion of the SEC column 1118 remains loaded with equilibrated buffer solution. None of the second reagent flows into the second waste syringe 1112. The second portion of the second reagent is also sufficient to force enough fluid into the second waste syringe 1112 such that the second waste syringe 1112 is fully loaded and the plunger 1164 is forced against the top, or stop. With the plunger 1164 forced against the stop, no additional fluid can be forced into the second waste syringe 1112. The volume of the second waste syringe 1112 is precisely configured so that the plunger 1164 is forced against the stop as a predetermined amount of second reagent including the eluted target analytes is input to the SEC column 1118.

The plunger 1164 moves from an initial position, as shown in FIG. 18, to the end position, as shown in FIG. 23. Similarly to the plungers 1154, 1158, and 1162, the movement of the plunger 1164 from the initial position to the end position corresponds to a specific amount of movement of the plunger 1172 in the driving syringe 1152, as driven by the drive motor 1174. In the case where the drive motor 1174 is a stepper motor, the movement of the plunger 1164 from the initial position to the end position corresponds to a specific number of steps of the stepper motor.

In some embodiments, once the specific number of steps corresponding to the movement of the plunger 1164 is reached, a control signal is sent to open the valve 1144 and the valve 1146. In other embodiments, a sensor (not shown) detects when the plunger 1164 reaches the end position, at which point a control signal is sent to open the valve 1144 and the valve 1146.

Within the SEC column 1118, the target analytes are separated from the second reagent. In this case, the target analytes are output from the SEC column 118 in an earlier fraction than the salt particles of the second reagent. Once the valves 1144 and 1146 are opened, the drive motor 1174 is actuated such that a third portion of the second reagent is displaced from the second reagent syringe 1104, as shown in FIG. 24.

Figure 24:
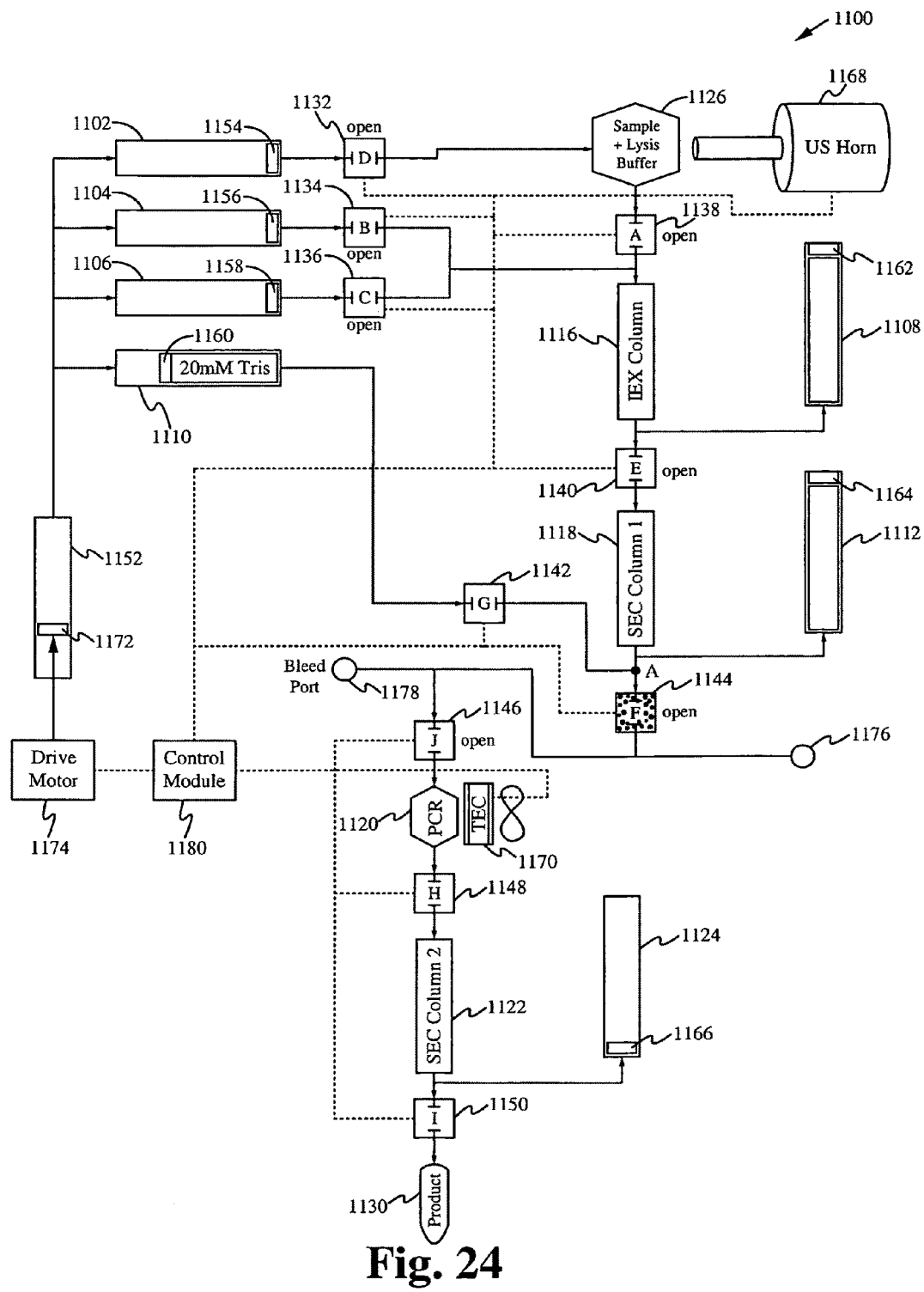

As the plunger 1156 is pushed forward from the second position to an end position, as shown in FIG. 24, the third portion of the second reagent is forced out of the reagent syringe 1104, through the open valve 1134, and through the IEC column 1116. The second reagent flows into the IEC column 1116 and not back toward the lysing chamber 1126 or though the valve 1136 due to the drive motor actuating force exerted on the plungers 1154 and 1158.

As the third portion of the second reagent flows through the IEC column 1116, the second reagent already loaded in the IEC column 1116 and the top portion of the SEC column 1118 is displaced, forcing the fraction including the equilibrated buffer solution and the target analytes at the output of the SEC column 1118 past the microfluidic fluid line that connects to the valve 1142 at point A. The fraction does not flow into the second waste syringe 1112, as the syringe 1112 is full. In some cases, the fraction is forced into or through the valve 1144. In other cases, the fraction or a trailing portion of the fraction falls short of the valve 1144, but is forced far enough along the microfluidic line that connects the SEC column 1118 to the valve 1144 so as to pass the microfluidic line connected to the valve 1142 at point A. The amount of the third portion of the second reagent is sufficient to force the fraction to the aforementioned position past point A, but does not force any of the second reagent past point A. In some embodiments, the amount of the third portion of the second reagent is insufficient to force any of the second reagent out of the SEC column 1118.

As the fraction is forced from the SEC column 1118 toward the thermal cycling chamber 1120, the pre-loaded thermal cycling reagent in the microfluidic lines between the valve 1144 and the valve 1146, and the fluid pre-loaded between the valve 1146 and the thermal cycling chamber 1120 is forced into the thermal cycling chamber 1120.

The plunger 1156 moves from the second position, as shown in FIG. 23, to the end position, as shown in FIG. 24. The movement of the plunger 1156 from the second position to the end position corresponds to a specific amount of movement of the plunger 1172 in the driving syringe 1152, as driven by the drive motor 1174. In the case where the drive motor 1174 is a stepper motor, the movement of the plunger 1156 from the second position to the end position corresponds to a specific number of steps of the stepper motor.

In some embodiments, once the specific number of steps corresponding to the movement of the plunger 1156 from the second position to the end position is reached, a control signal is sent to open the valve 1142. In other embodiments, a sensor (not shown) detects when the plunger 1156 reaches the end position, at which point a control signal is sent to open the valve 1142.

Figure 25:
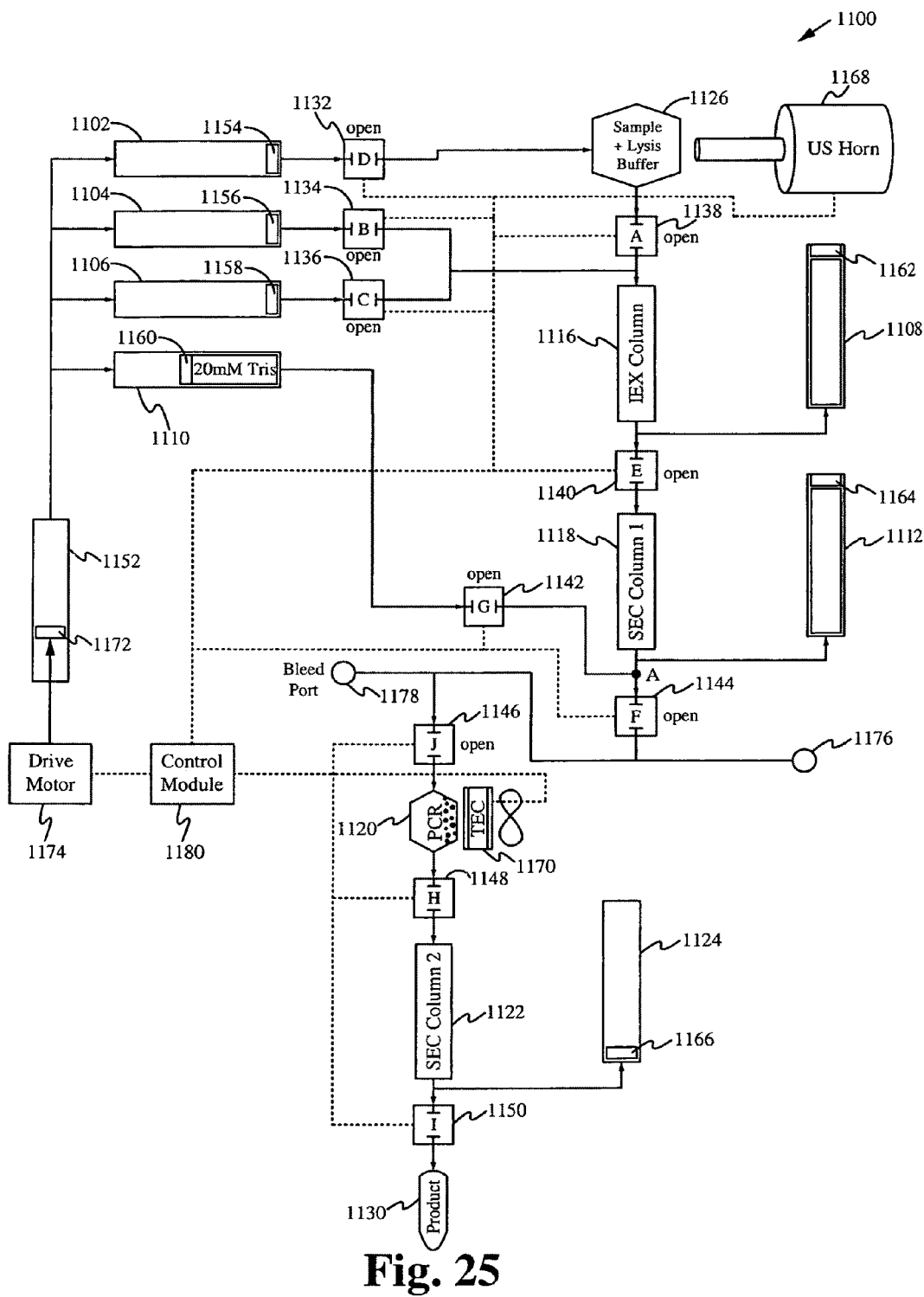

Once the valve 1142 opened, the drive motor 1174 is actuated such that a first portion of the fourth reagent is displaced from the fourth reagent syringe 1110, as shown in FIG. 25. As the plunger 1160 is pushed forward from an initial position, as shown in FIG. 24, to a first position, as shown in FIG. 25, the first portion of the fourth reagent is forced out of the reagent syringe 1110, forcing fluid through the open valve 1142, and through the open valves 1144 and 1146. The fluid flows toward the thermal cycling chamber 1120 and not back toward the SEC column 1118 due to the drive motor actuating force exerted on the plungers 1154, 1156, and 1158.

As the fluid flows through the valves 1144 and 1146, the fraction including the target analytes is forced into the thermal cycling chamber 1120. Since the valve 1148 remains closed, the thermal cycling reagent previously added to the thermal cycling chamber 1120 remains in place. The amount of the first portion of the fourth reagent is sufficient to force the fraction to the thermal cycling chamber 1120 and to fully load the thermal cycling chamber 1120 with fluid.

The movement of the plunger 1160 from the initial position to the first position corresponds to a specific amount of movement of the plunger 1172 in the driving syringe 1152, as driven by the drive motor 1174. In the case where the drive motor 1174 is a stepper motor, the movement of the plunger 1160 from the initial position to the first position corresponds to a specific number of steps of the stepper motor.

In some embodiments, once the specific number of steps corresponding to the movement of the plunger 1160 from the initial position to the first position is reached, a control signal is sent to the thermoelectric cooler (TEC) 1170 to perform a thermal cycling process, such as PCR, in order to amplify the amount of target analytes. The TEC 1170 can be part of the external actuation instrument or can be included as part of the cartridge.

The thermal cycling process is performed for a determined number of cycles, after which a control signal is sent to end the thermal cycling process and to open the valve 1148. In some embodiments, the microfluidic cartridge 1100 includes a detection module (not shown) coupled to the thermal cycling chamber 1120. The detection module is configured to perform a conventional detection process to detect the presence of one or more analytes in the thermal cycling chamber 1120. In an exemplary application, the detection module performs optical detection using an optical source and an optical sensor. In this exemplary configuration, the thermal cycling chamber is optically transparent, or includes an optically transparent portion, to allow optical interrogation of the internal contents.

Figure 26:
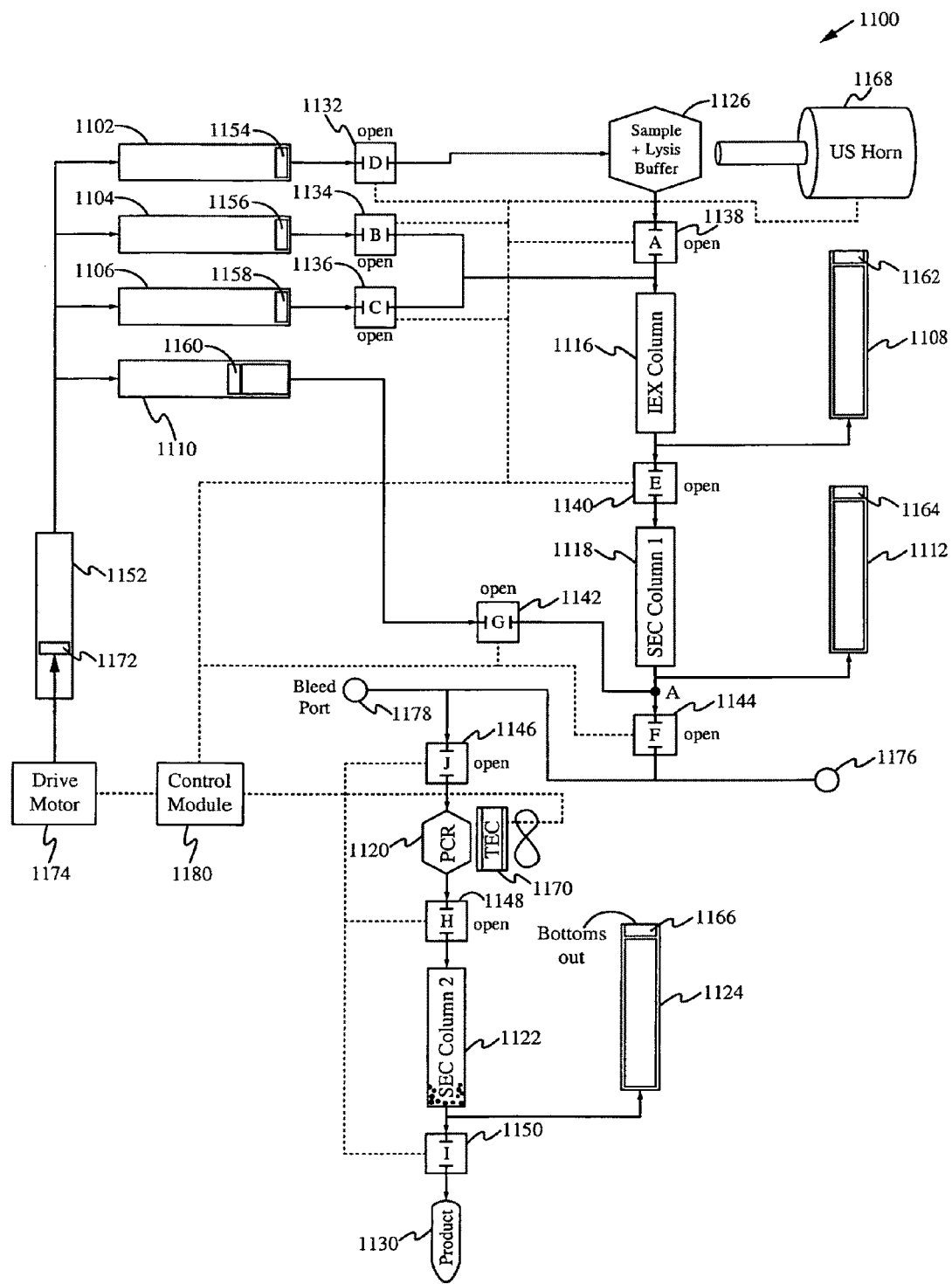

Once the valve 1148 is opened, the drive motor 1174 is actuated such that a second portion of the fourth reagent is displaced from the fourth reagent syringe 1110, as shown in FIG. 26. As the plunger 1160 is pushed forward from the first position, as shown in FIG. 25, to a second position, as shown in FIG. 26, the second portion of the fourth reagent is forced out of the reagent syringe 1110, forcing fluid through the open valve 1142, 1144, and 1146, and into the thermal cycling chamber 1120. The fourth reagent flows toward the thermal cycling chamber 1120 and not back toward the SEC column 1118 due to the drive motor actuating force exerted on the plungers 1154, 1156, and 1158.

As the fluid flows into the thermal cycling chamber 1120, the amplified solution in the thermal cycling chamber 1120, including the amplified target analytes, is forced out of the thermal cycling chamber 1120, through the valve 1148 and into the SEC column 1122.

As the amplified solution flows into the SEC column 1122, the equilibrated buffer solution initially loaded into the SEC column 1122 is displaced out of the SEC column 1122 by the in-flow of the amplified solution. Since the valve 1150 remains closed, the displaced equilibrated buffer solution flows into the third waste syringe 1124, forcing the plunger 1166 upward to an end position. The end position corresponds to a stop at the top of the third waste syringe 1124. The second portion of the fourth reagent is sufficient to input the amplified solution into a top portion of the SEC column 1122, while a bottom portion of the SEC column 1122 remains loaded with equilibrated buffer solution. None of the fourth reagent flows into the third waste syringe 1124. The second portion of the fourth reagent is also sufficient to force enough fluid into the third waste syringe 1124 such that the third waste syringe 1124 is fully loaded and the plunger 1166 is forced against the top, or stop. With the plunger 1166 forced against the stop, no additional fluid can be forced into the third waste syringe 1124. The volume of the third waste syringe 1124 is precisely configured so that the plunger 1166 is forced against the stop as substantially the entire amount of amplified solution, including the amplified target analytes, is input to the SEC column 1122.

The plunger 1166 moves from an initial position, as shown in FIG. 25, to the end position, as shown in FIG. 26. Similarly to the plungers 1162 and 1164, the movement of the plunger 1166 from the initial position to the end position corresponds to a specific amount of movement of the plunger 1172 in the driving syringe 1152, as driven by the drive motor 1174. In the case where the drive motor 1174 is a stepper motor, the movement of the plunger 1166 from the initial position to the end position corresponds to a specific number of steps of the stepper motor. The movement of the plunger 1160 from the first position to the second position also corresponds to this specific number of steps of the stepper motor.

In some embodiments, once the specific number of steps corresponding to the movement of the plunger 1160 from the first position to the second position is reached, a control signal is sent to open the valve 1150. In other embodiments, a sensor (not shown) detects when the plunger 1166 reaches the end position, at which point a control signal is sent to open the valve 1150.

The control signals to open the valves are described above as being generated in response to monitoring the number of steps actuated by the drive motor or by a sensor detecting a position of a particular plunger. It is also contemplated that the control signals can be generated in response to a combination of the two. In an exemplary application, the two mechanisms for generating the control signals function to error check each other and/or to provide redundancy within the system.

Within the SEC column 1122, the amplified target analytes are separated from the thermal cycling reagents. In this case, the target analytes are output from the SEC column 118 in an earlier fraction than the thermal cycling reagents. After the amplified solution is separated into fractions and the valve 1150 is opened, the drive motor 1174 is actuated such that a third portion of the fourth reagent is displaced from the fourth reagent syringe 1110, as shown in FIG. 27.

Figure 27:
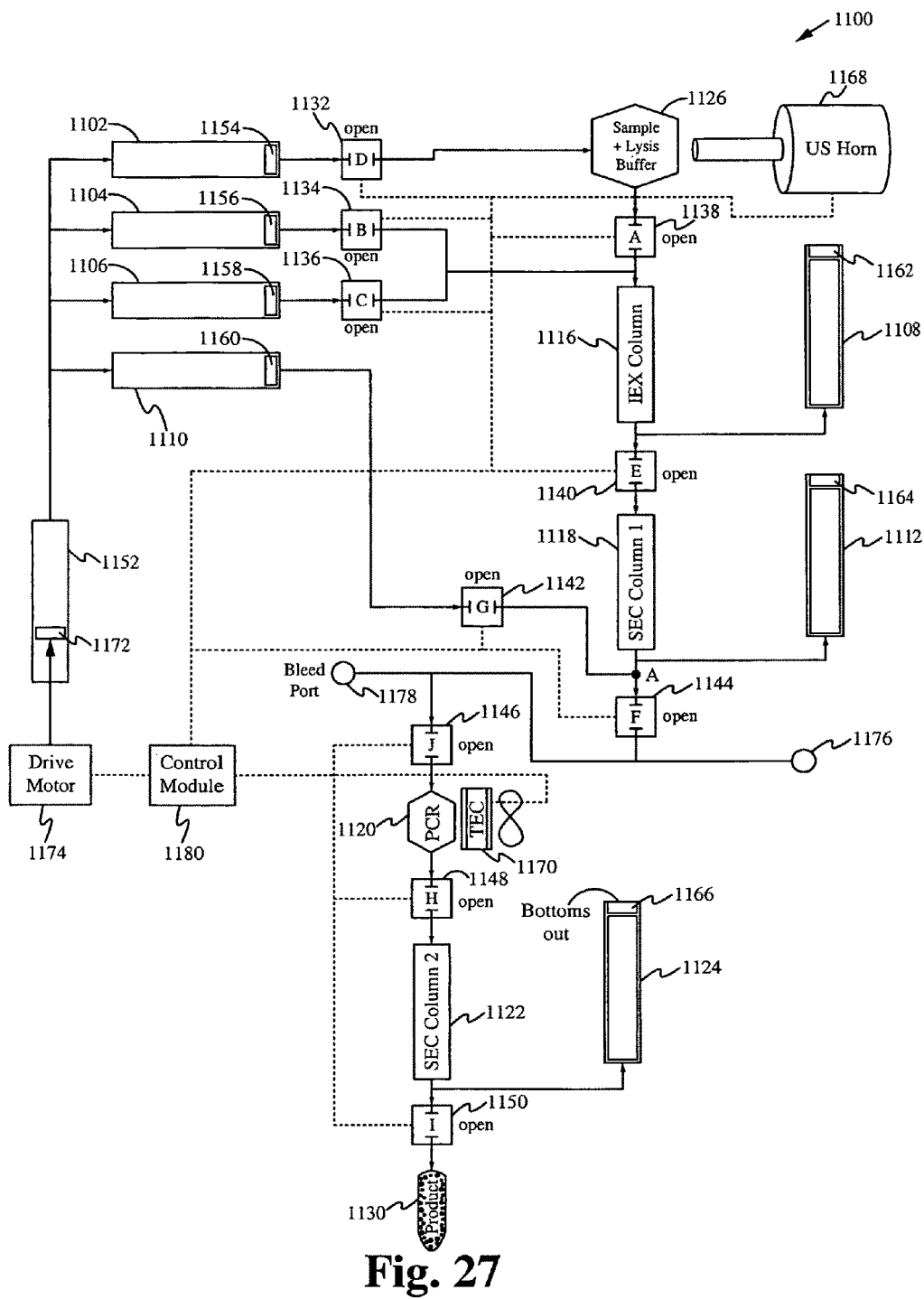
Figure 28:
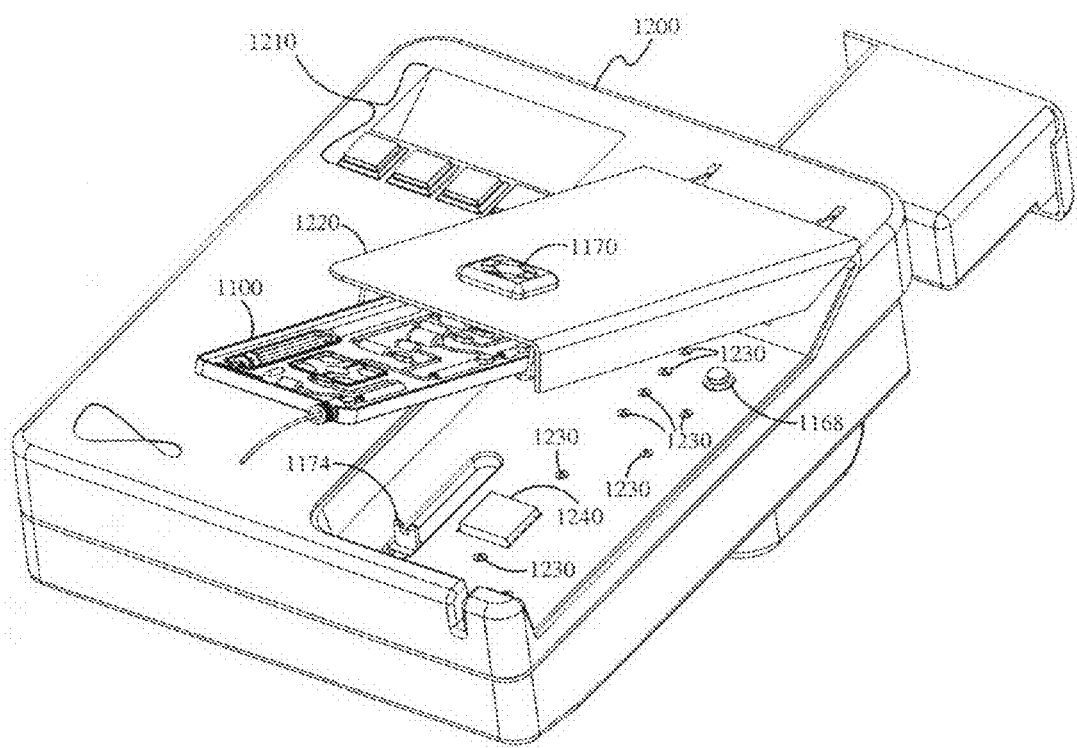
FIG. 28 illustrates the microfluidic cartridge coupled to an exemplary actuation instrument.

As the plunger 1160 is pushed forward from the second position to an end position, as shown in FIG. 27, the third portion of the fourth reagent is forced out of the reagent syringe 1110, thereby forcing fluid through the open valves 1142,1144, 1146, the thermal cycling chamber 1120, the valve 1148, and the SEC column 1122, thereby displacing the fraction including the amplified target analytes through the valve 1150 and into the output port 1130. In some embodiments, a collection vessel is coupled to the output port 1130 to collect the amplified target analytes. In other embodiments, the output port 1130 is coupled to additional microfluidic circuitry or processing apparatus for further sample preparation. The amplified target analyte fraction flows into the output port 1130 and not into the third waste syringe 1124 because the third waste syringe 1124 is full.

At this stage, the sample preparation within the cartridge 1100 is completed. The cartridge can be disengaged from the external actuation mechanism and disposed of. In this manner, the cartridge 1100 is disposable, including the waste product generated as part of the sample preparation process.

In general, operation of the cartridge is described in terms of a series of actuation steps. Once the cartridge is loaded with the fluid sample and the thermal cycling reagent, and then sealed, the sonication horn 1168 is actuated to perform a lysis process within the lysis chamber 1126. The valves 1132 and 1138 are then actuated. Actuation of the valves functions to open the valves, thereby enabling fluid flow there through. The drive motor 1174 is actuated by M steps, which corresponds to moving the plunger 1154 from the initial position to the end position. The valve 1136 is then actuated. The drive motor 1174 is actuated by N steps, which corresponds to moving the plunger 1158 from the initial position to the end position. The valve 1134 is then actuated. The drive motor 1174 is actuated by O steps, which corresponds to moving the plunger 1156 from the initial position to the first position. The valve 1140 is then actuated. The drive motor 1174 is actuated by P steps, which corresponds to moving the plunger 1156 from the first position to the second position. A period of time then elapses to enable the fractions to form via the SEC column 1118. The valves 1144 and 1146 are then actuated. The drive motor 1174 is actuated by Q steps, which corresponds to moving the plunger 1156 from the second position to the end position. The valve 1142 is then actuated. The drive motor 1174 is actuated by R steps, which corresponds to moving the plunger 1160 from the initial position to the first position. The TEC 1170 is then actuated to perform the thermal cycling process within the thermal cycling chamber

1120. The valve 1148 is then actuated. The drive motor 1174 is actuated by S steps, which corresponds to moving the plunger 1160 from the first position to the second position. A period of time then elapses to enable the fractions to form via the SEC column 1122. The valve 1150 is then actuated. The drive motor 1174 is actuated by T steps, which corresponds to moving the plunger 1160 from the second position to the end position, thereby completing the sample preparation process.

In contrast to the capture and purification apparatuses of FIGS. 14 and 15, the capture and purification apparatus of FIG. 17 (cartridge 1100) does not include sensors configured to detect different fluid fronts, such as changes in the salt concentration of the fluid, of the fluid output from IEC and SEC columns. Instead, the cartridge 1100 monitors the fluid volume displacement within the system, such as by monitoring the number of steps performed by the stepper motor, to determine when to actuate specific valves and properly direct fluid flow. Completely loading the cartridge with fluid prior to preparing the fluid sample substantially removes all air within the fluid flow paths, which enables discrete volume-driven control. Since the cartridge is fully loaded with fluid, determining the location of each fluid front is very precise. The movement of the driving syringe, for example the number of steps of the stepper motor, determines the position of each fluid front within the cartridge.

The configuration of the cartridge 110 and the sequence of operation is shown for exemplary purposes only. It is understood that the concepts associated with the description of the cartridge 1100 can be applied to alternative applications and to alternatively configure other cartridges or apparatuses. In general, a volume-driven system applies single-direction valves, a single fluid driving device, and fluid lines to control and discretely direct fluid flow within a full-loaded fluidic system. Such control enables various fluid sample processing techniques to be performed including, but not limited to, lysis, target analyte capture and purification, and/or thermal cycling.

The relative positions of each of the plungers is shown for exemplary purposes and is not intended to indicate the actual amount of movement. Further, the relative volumes of each of the syringes 1102, 1104, 1106, 1108, 1110, 1112, 1124, and 1152 is shown for exemplary purposes only and is not intended to indicate the actual volume of each syringe. Additionally, the plunger 1172 in the driving syringe 1152 is not shown to move in the FIGS. 18-27, but this is not intended to indicate a lack of movement of the plunger 1172. Instead, the plunger 1172 moves as indicated in the accompanying description, in response to actuation of the drive motor 1174, which results in force applied to the plungers 1154, 1156, 1158, and 1160.

It is understood that the microfluidic cartridge is not limited to the components shown in FIGS. 16 and 17. The microfluidic cartridge can be alternatively configured to include other combinations of components included in the various capture and purification apparatus embodiments and the collection and detection system described above. For example, the microfluidic cartridge 1100 shown in FIGS. 17-27 can be configured without the thermal cycling functionality, in which case the thermal cycling chamber 1120, the column 1122, and the TEC 1170 are not included. In this configuration, the valves 1146, 1148, and 1150, and waste syringe 1124 are also not included, unless additional fluid flow and/or waste collection is desired. As another example, the microfluidic cartridge 1100 can also include a second TEC, such as the TEC 1240 in FIG. 28, coupled to an opposite side of the thermal cycling chamber 1120 as the first TEC 1170.

Although the capture and purification apparatus is described above as part of the microfluidic cartridge and/or part of the collection and detection system, it is understood that the capture and purification apparatus can be a stand-alone apparatus, or can be incorporated as part of an alternative system in which capturing and purifying one or more targeted analytes is desired.

The present invention has been described in terms of specific embodiments incorporating details to facilitate the understanding of the principles of construction and operation of the invention. The specific configurations shown and the methodologies described in relation to the various modules and the interconnections therebetween are for exemplary purposes only. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. An apparatus to process an input fluid sample including one or more targeted analytes, the apparatus comprising:
   a. an actuation instrument comprising:
      i. a drive motor configured to provide discrete increments of actuation; and
      ii. a plurality of valve actuation mechanisms;
   b. a cartridge coupled to the actuation instrument, the cartridge comprising:
      i. a driving syringe coupled to the drive motor;
      ii. a plurality of reagent syringes, wherein a fluid input port of each reagent syringe is commonly coupled to the driving syringe, further wherein each reagent syringe is configured to displace a reagent fluid in response to an actuation of the driving syringe, each reagent fluid is used to process the one of more target analytes;
      iii. a plurality of processing vessels, each processing vessel configured to process the one or more target analytes;
      iv. microfluidic circuitry including a plurality of valves and fluid lines configured to couple the driving syringe, the plurality of reagent syringes, and the plurality of processing vessels, wherein each valve is coupled to one valve actuation mechanism and each valve is configured to actuate no more than once; and
   c. a control module coupled to the drive motor and the plurality of valve actuation mechanisms, wherein the control module is configured to provide electrical control signals to the drive motor and the plurality of valve actuation mechanisms to independently actuate the drive motor and each of the plurality of valve actuation mechanisms, further wherein the control module comprises program instructions configured to actuate the drive motor and selective ones of the plurality of valve actuation mechanism such that a position of the one or more target analytes within the cartridge is determined according to a cumulative amount of actuation increments of the drive motor.

2. The apparatus of claim 1 wherein the cartridge is fully loaded with fluid prior to an initial actuation of the drive motor.

3. The apparatus of claim 2 wherein actuation of the drive motor forces fluid flow within the cartridge.

4. The apparatus of claim 3 wherein a position of each reagent fluid within the cartridge is defined according to a fluid front of each reagent fluid, and the position of each fluid front is determined according to the cumulative amount of actuation increments performed by the drive motor.

5. The apparatus of claim 1 wherein each valve is configured to actuate from a closed position to an open position.

6. The apparatus of claim 1 wherein the cartridge further comprises a plurality of waste vessels coupled to the microfluidic circuitry, wherein the plurality of waste vessels are configured to store all waste generated while processing the fluid sample, further wherein the cartridge is disposable.

7. The apparatus of claim 6 wherein each waste vessel includes a plunger and a plunger stop, the plunger configured to be displaced by incoming waste and the plunger stop positioned to regulate a maximum amount of waste to be added to the waste vessel.

8. The apparatus of claim 1 wherein each reagent syringe includes a plunger and a plunger stop, the plunger configured to displace the reagent fluid and the plunger stop positioned to regulate a maximum fluid displaced by the plunger.

9. The apparatus of claim 1 wherein each of the processing vessels comprises one of the group consisting of a lysing chamber, an ion-exchange chromatography column, a size-exclusion chromatography column, and a thermal cycling chamber.

10. The apparatus of claim 9 wherein the actuation instrument further comprises a sonication horn coupled to the lysing chamber.

11. The apparatus of claim 9 wherein the actuation instrument further comprises a thermo-electric cooler coupled to the thermal cycling chamber.

12. The apparatus of claim 1 wherein the drive motor comprises a stepper motor and the cumulative amount of actuation increments is a cumulative number of steps of the drive motor.

13. The apparatus of claim 12 wherein the control module is configured to independently actuate each of the valve mechanisms according to a specific cumulative amount of actuation increments.

14. The apparatus of claim 1 further comprising one or more sensors positioned in each of the reagent syringes, wherein each sensor is configured to detect a position of the plunger in the reagent syringe.

15. The apparatus of claim 14 wherein the control module is configured to independently actuate each of the valve mechanisms according to the detected positions of the plungers.

16. The apparatus of claim 1 wherein each of the valve actuation mechanisms comprises a solenoid.

17. The apparatus of claim 1 wherein the cartridge further comprises a fluid sample input port coupled to one of the processing vessels.

18. The apparatus of claim 1 wherein the control module comprises program instructions configured to actuate the drive motor and selective ones of the plurality of valve actuation mechanism to displace reagent fluid from only one reagent syringe at a time.

19. The apparatus of claim 1 wherein the control module comprises an electrical processing circuit.

* * * * *